US012618114B2

(12) United States Patent
Tripathi

(10) Patent No.: US 12,618,114 B2
(45) Date of Patent: **\*May 5, 2026**

(54) METHOD FOR IDENTIFYING CANCER IN A SUBJECT

(71) Applicant: 23IKIGAI PTE LTD, Singapore (SG)

(72) Inventor: Ashish Tripathi, Prospect Vale (AU)

(73) Assignee: 23IKIGAI PTE LTD, Singapore (SG)

( * ) Notice: Subject to any disclaimer, the term of this patent is extended or adjusted under 35 U.S.C. 154(b) by 85 days.

This patent is subject to a terminal disclaimer.

(21) Appl. No.: 17/314,442

(22) Filed: May 7, 2021

(65) Prior Publication Data

US 2021/0404013 A1     Dec. 30, 2021

Related U.S. Application Data

(60) Provisional application No. 63/109,073, filed on Nov. 3, 2020, provisional application No. 63/077,459, filed on Sep. 11, 2020, provisional application No. 63/041,413, filed on Jun. 19, 2020.

(51) Int. Cl.
*C12Q 1/6886*          (2018.01)

(52) U.S. Cl.
CPC ..... *C12Q 1/6886* (2013.01); *C12Q 2600/106* (2013.01); *C12Q 2600/118* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 11,926,875 B2 * | 3/2024 | Tripathi | ............... C12Q 1/6881 |
| 2009/0155225 A1 | 6/2009 | Ratajczak et al. | |
| 2020/0370134 A1 | 11/2020 | Tripathi et al. | |
| 2023/0212688 A1 | 7/2023 | Tripathi | |

FOREIGN PATENT DOCUMENTS

| | | |
|---|---|---|
| JP | 2010178650 A | 8/2010 |
| WO | WO-2019239431 A1 | 12/2019 |

OTHER PUBLICATIONS

Kuruca et al Stem Cell Reviews and Reports. Jun. 2019. 15: 730-742 (Year: 2019).*
Knopfler, P. "Fact-checking VSEL stem cells & VSEL treatment," The Niche, Trusted stem cell blog & resources, Jun. 7, 2022, available via URL: <pscell.com/2022/06/fact-checking-vsel-stem-cells-supposed-vsel-treatment/,>. (Year: 2022).*
Starzynska et al Gastroenterology 140.5, Suppl. 1: S831. May 2011, abstract Tu1774 and Tu1777, p. S-831 (Year: 2011).*
Ratajczak et al Leukemia. 2014. 28: 473-484 (Year: 2014).*

Tripathi et al. Stem Cell Rev and Rep. May 6, 2021. 17: 1827-1839 (Year: 2021).*
Lucchinetti et al., "Inflammatory Cortical Demyelination in Early Multiple Sclerosis", *N Engl J Med*, vol. 365, No. 23, pp. 2188-2197 (2011).
Ene et al., "Synovial inflammation in patients with different stages of knee osteoarthritis", *Rom J Morphol Embryol*, vol. 56, No. 1, pp. 169-173 (2015).
Asai et al., "Is emphysema a risk factor for pneumothorax in CT-guided lung biopsy?", *SpringerPlus*, pp. 1-6 (2013).
Sherman et al., "Liver Biopsy in Cirrhotic Patients", *Am J Gastroenterol*, vol. 102, No. 4, pp. 789-793 (2007).
Gerlinger et al., "Intratumor Heterogeneity and Branched Evolution Revealed by Multiregion Sequencing", *N Engl J Med*, vol. 366, No. 10, pp. 883-892 (2012).
Bedard et al., "Tumour heterogeneity in the clinic", *Nature*, vol. 501 (7467), pp. 355-364 (2013).
Mlika et al., "Liquid biopsy in lung cancer", *Tunisie Medicale*, vol. 95, No. 11, pp. 965-971 (2017).
Wong et al., "Sequence artefacts in a prospective series of formalin-fixed tumours tested for mutations in hotspot regions by massively parallel sequencing", *BMC Medical Genomics*, vol. 7, No. 23, pp. 1-10 (2013).
Li et al., "OCT4B modulates OCT4A expression as ceRNA in tumor cells", *Oncology Reports*, vol. 33, pp. 2622-2630 (2015).
Diehl et al., "Circulating mutant DNA to assess tumor dynamics", *Nat Med.*, vol. 14, No. 9, pp. 985-990 (2008).
Palmirotta et al., "Liquid biopsy of cancer: a multimodal diagnostic tool in clinical oncology", *Ther Adv Med Oncol*, vol. 10, pp. 1-24 (2018).
Zhou et al., "Application of exosomes as liquid biopsy in clinical diagnosis", *Signal Transduction and Targeted Therapy*, vol. 5, No. 144, pp. 1-12 (2020).
Kowalik et al, "Current approaches for avoiding the limitations of circulating tumor cells detection methods-implications for diagnosis and treatment of patients with solid tumors", *Translational Research*, vol. 185, pp. 58-84 (2017).
Wang et al., "The emerging roles of Oct4 in tumor-initiating cells", *Am J Physiol Cell Physiol*, vol. 309, No. 11, pp. C709-C718 (2015).
Monferrer et al., "High Oct4 expression: implications in the pathogenesis of neuroblastic tumours", *BMC Cancer*, vol. 19, No. 1, pp. 1-8 (2019).

(Continued)

*Primary Examiner* — Carla J Myers
(74) *Attorney, Agent, or Firm* — Wilson Sonsini Goodrich & Rosati

(57) ABSTRACT

The present disclosure discloses an in-vitro and non-invasive method for detecting a medical condition in a subject. The method involves enriching very small embryonic like stem cells from the sample, to obtain a mixture comprising said very small embryonic like stem cells; obtaining nucleic acid from the mixture of step; performing an assay with the nucleic acid for analysing expression level of Oct4A in the very small embryonic like stem cells from the sample; and comparing the expression level of Oct4A in the very small embryonic like stem cells from the sample with an expression level of Oct4A in a control sample. The present disclosure also provides a method for predicting the onset of cancer and for predicting the presence of cancer. A method of treating cancer is also disclosed herein. Moreover, a reagent kit and a detection kit are also disclosed.

16 Claims, 19 Drawing Sheets

Specification includes a Sequence Listing.

(56)          References Cited

OTHER PUBLICATIONS

Sodja et al., "The prognostic value of whole blood SOX2, NANOG and OCT4 mRNA expression in advanced small-cell lung cancer", *Radiol Oncol*, vol. 50, No. 2, pp. 188-196 (2016).

Bray et al., "Global Cancer Statistics 2018: Globocan Estimates of Incidence and Mortality Worldwide for 36 Cancers in 185 Countries", *CA Cancer J Clin*, vol. 68, No. 6, pp. 394-424 (2018).

Chakravarthi et al., "Genomic and Epigenomic Alterations in Cancer", Am J Pathol, vol. 186, No. 7, pp. 1724-1735 (2016).

Hammoudi et al., "Metabolic alterations in cancer cells and therapeutic implications", *Chin J Cancer*, vol. 30, Issue 8, pp. 508-525 (2011).

Riggi et al., "Cancer Metastasis: A Reappraisal of Its Underlying Mechanisms and Their Relevance to Treatment", *Annu. Rev. Pathol. Mech. Dis.*, vol. 13, pp. 117-140 (2018).

Schiffman et al., "Early Detection of Cancer: Past, Present, and Future", Cancer Screening and Surveillance, *ASCO Educational Book*, pp. 57-65 (2015).

Gandhi et al., "Burden of preventable cancers in India: Time to strike the cancer epidemic", *Journal of the Egyptian National Cancer Institute*, vol. 29, pp. 11-18 (2017).

Eskiizmir et al., "Nanomaterials: Promising Structures for the Management of Oral Cancer", Chapter 17 Nanomaterials, pp. 511-544 (2017).

Temilola et al., "The Prospect and Challenges to the Flow of Liquid Biopsy in Africa", *Cells*, vol. 8, 862, pp. 1-27 (2019).

Ilic et al., "Prostate cancer screening with prostate-specific antigen (PSA) test: a systematic review and meta-analysis", *BMJ*, vol. 362, pp. 1-28 (2018).

Miller, A. B., Book Review Fulfilling the Potential of Cancer Prevention and Early Detection Edited by Susan J. Curry, Tim Byers, and Maria Hewitt. 542, *New England Journal of Medicine*, vol. 349, No. 18, pp. 1781-1782 (2003).

International Search Report and Written Opinion for Application No. PCT/IN2019/050453, dated Sep. 13, 2019.

Mansoori et al., "Circulating cancer stem sell markers in breast carcinomas: a systematic review protocol", Systematic Reviews, Biomed Central Ltd., 22:1444-1452 (2015).

Mirzaei et al., "Upregulation of circulating cancer stem cell marker, DCLK1 but not Lgr5, in chemoradiotherapy-treated colorectal cancer patients", Tumor Biology. 36:4801-4810 (2015).

Rhee et al., "Simultaneous detection of mRNA and protein stem cell markers in live cells", BMC Biotechnology, Biomed Central Ltd. 9:30 (2009).

Hong et al., "Increased Expression of Circulating Cancer Step Cell Markers During the Perioperative Period Predicts Early Recurrence After Curative Resection of Hepatocellular Carcinoma", Annals of Surgical Oncology. 22:1444-1452 (2015).

Scatena et al., "Circulating tumour cells and cancer stem cells: A role for proteomics in defining the interrelationships between function, phenotype and differentiation with potential clinical applications", BBA—Reviews on Cancer. 1834:129-143 (2013).

Di et al., "The stem cell markers Oct4A, Nanog and c-Myc are expressed in ascites cells and tumor tissue of ovarian cancer patients", Cell Oncology 36, p. 363-374 (2013).

Pierini et al., "Efficient isolation and enrichment of mesenchymal stem cells from bone marrow", Cytotherapy 14, pp. 686-693 (2012).

Density Gradient Centrifugation Protocol, "Isolation and Cryopreservation of PBMCs—Ficoll Method without plasma collection", p. 1-11, 2007, https://www.innnnunetolerance.org/sites/default/files/Separation% 20of%2Onnononuclear%2Ocells%20fronn%20whole%20blood% 20using%20Ficoll%20gradients.pdf, accessed May 27, 2021.

Sampson et al., "Clinical Aspects of Regenerative Medicine: Tendon, Ligament, and Joint", Translational Regenerative Medicine, Academic Press, 2015, pp. 293-311 (2015).

Piao et al., "Theoretical prediction and validation of cell recovery rates in preparing platelet-rich plasma through a centrifugation", PLoS ONE 12(11): e0187509 (2017).

Vissers et al., "Rapid purification of human peripheral blood monocytes by centrifugation through Ficoll-Hypaque and Sepracell-MN", Journal of Immunological Methods, vol. 110, pp. 203-207 (1988).

Gigante et al., Negative and Positive Separation Techniques for the Isolation of Antigen-Specific CD8$^+$ T Cells from Blood and Tumor Tissue, Cytotoxic T-Cells: Methods and Protocols, Methods in Molecular Biology, vol. 1186, 2014.

Bhartiya et al., "Very Small Embryonic-Like Stem Cells with Maximum Regenerative Potential Get Discarded During Cord Blood Banking and Bone Marrow Processing for Autologous Stem Cell Therapy", Stem Cells and Development, vol. 21, No. 1, pp. 1-6 (2012).

Tripathi et al., "Quest for Pan-Cancer Diagnosis/Prognosis Ends with HrC Test Measuring Oct4A in Peripheral Blood", Stem Cell Reviews and Reports, vol. 17, pp. 1827-1839 (2021).

Zhang et al., "Peripheral Blood Stem Cells: Phenotypic Diversity and Potential Clinical Applications", Stem Cell Rev and Rep, vol. 8, pp. 917-925 (2012).

Ratajczak et al., "Very Small Embryonic/Epiblast-Like Stem Cells", The American Journal of Pathology, vol. 174, No. 6, pp. 1985-1992 (2009).

Sovalat et al., "Human Very Small Embryonic-Like Stem Cells Are Present in Normal Peripheral Blood of Young, Middle-Aged, and Aged Subjects", Stem Cells International, vol. 2016, pp. 1-8.

Abbott, "Doubt cast over tiny stem cells", Nature, vol. 499 pp. 390 (2013).

Tripathi et al., "Stem Cells and Progenitors in Human Peripheral Blood Get Activated by Extremely Active Resveratrol (XARTM)", Stem Cell Reviews and Reports, vol. 14, pp. 213-222 (2018).

Brooks et al., "Next-generation sequencing facilitates quantitative analysis of wild-type and Nrl retinal transcriptomes", Molecular Vision, vol. 17, pp. 3034-3054 (2011).

Soh et al., "RNA Flow Cytometry using the Branched DNA Technique", Methods Mol Biol., pp. 49-77 (2018).

Bgee: Gene Expression Data in Animals. 3 pages, May 29, 2020. Available at: https://web.archive.org/web/20200529121916/https:// bgee.org/.

Bowcock, Anne, et al., The Genetics of Psoriasis, Psoriatic Arthritis and Atopic Dermatitis. Human Molecular Genetics 13: R43-R55 (2004).

Chakraborty, Sajib, et al., The difficulties in cancer treatment. Ecancermedicalscience 6:1-5 (2012).

Chakravarthi, Balabhadrapatruni, et al., Genomic and Epigenomic Alterations in Cancer. The American Journal of Pathology 186(7):1724-1735 (2016).

Chaudhary, Shahid, et al., Cell-free Chromatin: A Newly Described Mediator of Systemic Inflammation. Journal of Biosciences 44(2):1-6 (2019).

Chess 2.2 data 2 pages. Feb. 3, 2020. Available at: https://web. archive.org/web/20200203042334/ http://ccb.jhu.edu/chess.

Cleary, Sean, et al., Identification of Driver Genes in Hepatocellular Carcinoma by Exome Sequencing. Hepatology 58(5):1693-1702 (2013).

Cowling, Tara, et al., An Overview of Liquid Biopsy for Screening and Early Detection of Cancer. CADTH Issues in Emerging Health Technologies. 179:1-13 (2019).

Dhingra, Ravi, et al., Biomarkers in Cardiovascular Disease: Statistical Assessment and Section on Key Novel Heart Failure Biomarkers. Trends in Cardiovascular Medicine 27(2):123-133 (2017).

DISGENET—Data for tomorrow's health. 2 pages, archived Jul. 16, 2024. Available at: https://web.archive.org/web/20240716020459/ https://www.disgenet.com/.

E!Ensembl: Ensembl genome browser for vertebrate genomes. 2 pages, May 27, 2020. Available at: https://web.archive.org/web/ 20200527171514/https://asia.ensembl.org/index.html, only provided cover page for Ensemble browser.

Francis, Rohin, et al., Myocardial Biopsy: Techniques and Indications. Heart 104(11):950-958 (2018).

Fulfilling the Potential for Cancer Prevention and Early Detection (Ed. Curry, Susan J. et al.), National Cancer Policy Board: Institute of Medicine National Research Council of the National Academies. 565 pages, (2003).

(56) References Cited

OTHER PUBLICATIONS

GeneCards®: The Human Gene Database. 2 pages, Jun. 15, 2020. Available at: https://web.archive.org/web/20200615134200/https://www.genecards.org/.

GTEx Portal: Explore the Adult GTEx data, 4 pages (2024). Retreived from the internet: https://gtexportal.org/home/.

Hannivoort, Rebekka, et al., Genomics and Proteomics in Liver Fibrosis and Cirrhosis. Fibrogenesis and Tissue Repair 5(1):1-14 (2012).

Harvey, Nathan, et al., Skin Biopsy in the Diagnosis of Neoplastic Skin Disease. Australian Family Physician 46(5):289-294 (2017).

Hendrickx, Debbie A. E, et al., Gene Expression Profiling of Multiple Sclerosis Pathology Identifies Early Patterns of Demyelination Surrounding Chronic Active Lesions. Frontiers in Immunology 8:1-15 (2017).

Hogan, Jonathan, et al., The Native Kidney Biopsy: Update and Evidence for Best Practice. Clinical Journal of the American Society of Nephrology 11(2):354-362 (2016).

Hu, Cheng, et al., PPARG, KCNJ11, CDKAL1, CDKN2A-CDKN2B, IDE-KIF11-HHEX, IGF2BP2 and SLC30A8 are Associated with Type 2 Diabetes in a Chinese Population. PLoS ONE 4(10):1-6 (2009).

Ju, Wenjun, et al., Genomic Biomarkers for Chronic Kidney Disease. Translational Research 159(4):290-302 (2012).

Killock, David., Diagnosis: CancerSEEK and destroy—a blood test for early cancer detection. Nature reviews Clinical oncology 15(3):133 (2018).

Kim, Woo Jin, et al., Candidate Genes for COPD: Current Evidence and Research. International Journal of Chronic Obstructive Pulmonary Disease 10(1):2249-2255 (2015).

Koyuncu, Emre, et al., Sirtuins Are Evolutionarily Conserved Viral Restriction Factors. mBio 5(6):e02249-14 (2014).

Kuster, Gabriela, et al., SARS-CoV2: should inhibitors of the renin-angiotensin system be withdrawn in patients with COVID-19?. European Heart Journal, 1-3 (2020).

Lewis, John. et al. Images presented in Montreal, Canada at the International Cell Senescence Association Conference, Jul. 8-11, 2018, entitled: "Selective Ablation of Senescent and Malignant Cells Using Apoptotic Gene Therapy." (pp. 1-28).

NCBI phenotype-genotype integrator. 2 pages, Mar. 22, 2020. Available at: https://web.archive.org/web/20200321235515/https://www.ncbi.nlm.nih.gov/gap/phegeni.

NCBI SNP database. Available at: https://web.archive.org/web/20200531112350/https://www.ncbi.nlm.nih.gov/snp/.

Pertea, Mihaela et al., CHESS: a new human gene catalog curated from thousands of large-scale RNA sequencing experiments reveals extensive transcriptional noise. Genome Biology. 19(1):208, pp. 1-14 (2018).

Shaw, Paul, et al., Cancer of unknown primary. Practical Clinical Oncology: 442-448 (2008).

Shen, Zheyu, et al., Current Detection Technologies of Circulating Tumor Cells. Chemical Society Reviews 46(8): 2038-2056 (2017).

Tissues: Tissue expression database. 1 page. Apr. 23, 2020. Available at: https://web.archive.org/web/20200423123156/https://tissues.jensenlab.org/Search, Only a cover page for searching gene name provided.

Vaduganathan, Muthiah, et al., Renin-Angiotensin-Aldosterone System Inhibitors in Patients with Covid-19. New England Journal of Medicine. 382(17):1653-1659 (2020).

Varadhachary, Gauri R. Carcinoma of unknown primary origin. Gastrointest Cancer Res. Nov. 2007;1(6):229-235.

Wang, Xia, et al., Concise Review: Isoforms of Oct4 Contribute to the Confusing Diversity in Stem Cell Biology. Stem Cells 28(5):885-893 (2010).

Westcott, Peter, et al., The Genetics and Biology of KRAS in Lung Cancer. Chinese Journal of Cancer 32(2):63-70 (2013).

Zhong, Leilei, et al., Correlation Between Gene Expression and Osteoarthritis Progression in Human. International Journal of Molecular Sciences 17(7):1-14 (2016).

* cited by examiner

| | |
|---|---|
| Non-Cancer | 0-2 |
| Organ Inflammation | 2-6 |
| High Risk | 6-10 |
| Stage I Cancer | 10-20 |
| Stage II Cancer | 20-30 |
| Stage III Cancer | 30-40 |
| Stage IV Cancer | 40-50 |

FIG. 1

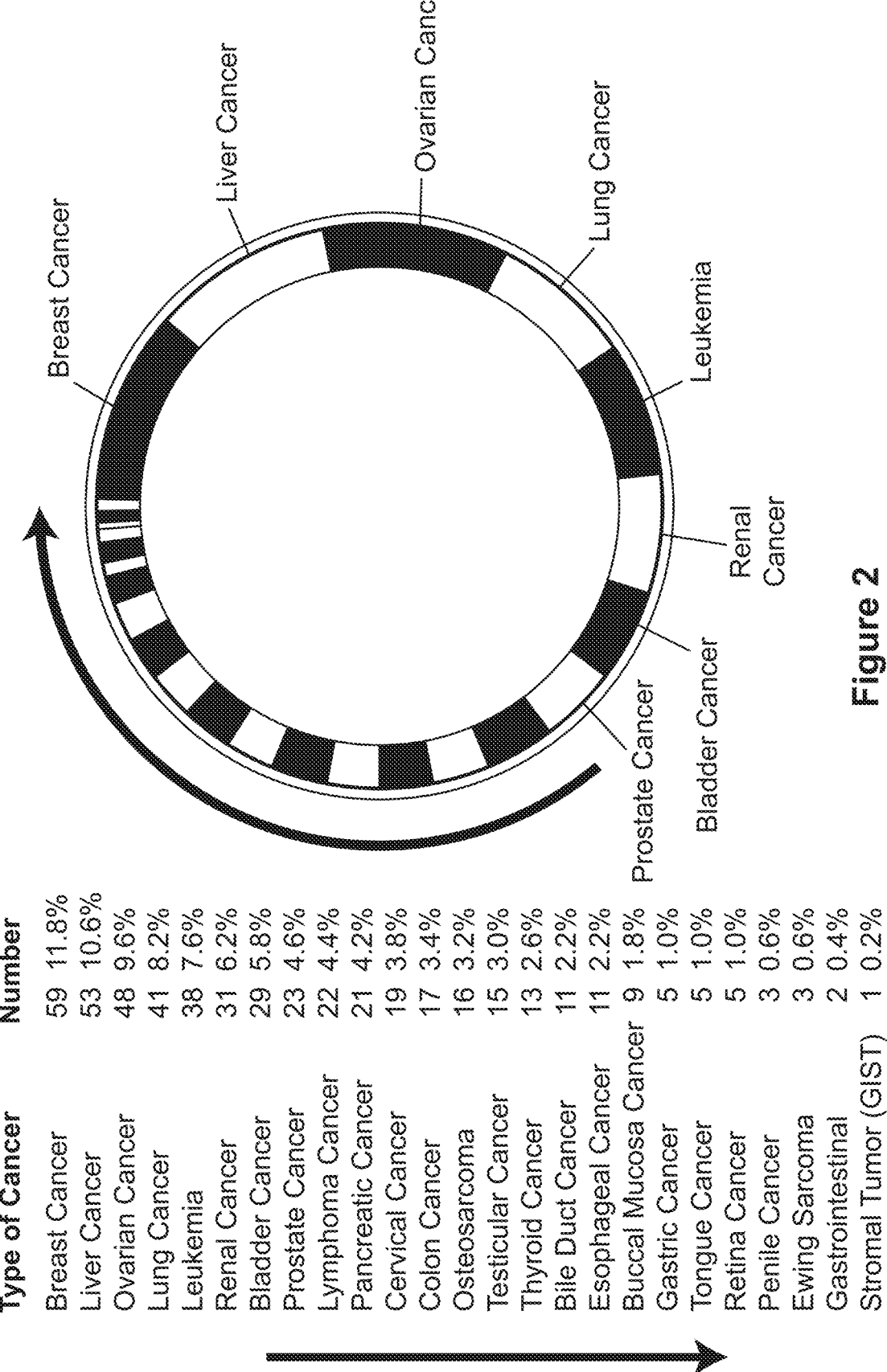

Figure 2

| Type of Cancer | Number | |
|---|---|---|
| Breast Cancer | 59 | 11.8% |
| Liver Cancer | 53 | 10.6% |
| Ovarian Cancer | 48 | 9.6% |
| Lung Cancer | 41 | 8.2% |
| Leukemia | 38 | 7.6% |
| Renal Cancer | 31 | 6.2% |
| Bladder Cancer | 29 | 5.8% |
| Prostate Cancer | 23 | 4.6% |
| Lymphoma Cancer | 22 | 4.4% |
| Pancreatic Cancer | 21 | 4.2% |
| Cervical Cancer | 19 | 3.8% |
| Colon Cancer | 17 | 3.4% |
| Osteosarcoma | 16 | 3.2% |
| Testicular Cancer | 15 | 3.0% |
| Thyroid Cancer | 13 | 2.6% |
| Bile Duct Cancer | 11 | 2.2% |
| Esophageal Cancer | 11 | 2.2% |
| Buccal Mucosa Cancer | 9 | 1.8% |
| Gastric Cancer | 5 | 1.0% |
| Tongue Cancer | 5 | 1.0% |
| Retina Cancer | 5 | 1.0% |
| Penile Cancer | 3 | 0.6% |
| Ewing Sarcoma | 3 | 0.6% |
| Gastrointestinal | 2 | 0.4% |
| Stromal Tumor (GIST) | 1 | 0.2% |

Distribution of types of cancer
patients enrolled in the study

| | | |
|---|---|---|
| Non-cancer | 498 | 49.8% |
| High-risk | 7 | 0.7% |
| Stage I | 11 | 1.1% |
| Stage II | 94 | 9.4% |
| Stage III | 133 | 13.3% |
| Stage IV | 257 | 25.7% |
| Total | 1000 | |

A) Box plot showing distribution of subjects identified as non-cancer and top 10 cancer sub-types in our study on basis of their HrC values.

B) Dot plot showing distribution of subjects identified as non-cancer and cancer sub-types on basis of HrC values.

C) Dot plot showing subject classification into various stages based on HrC values

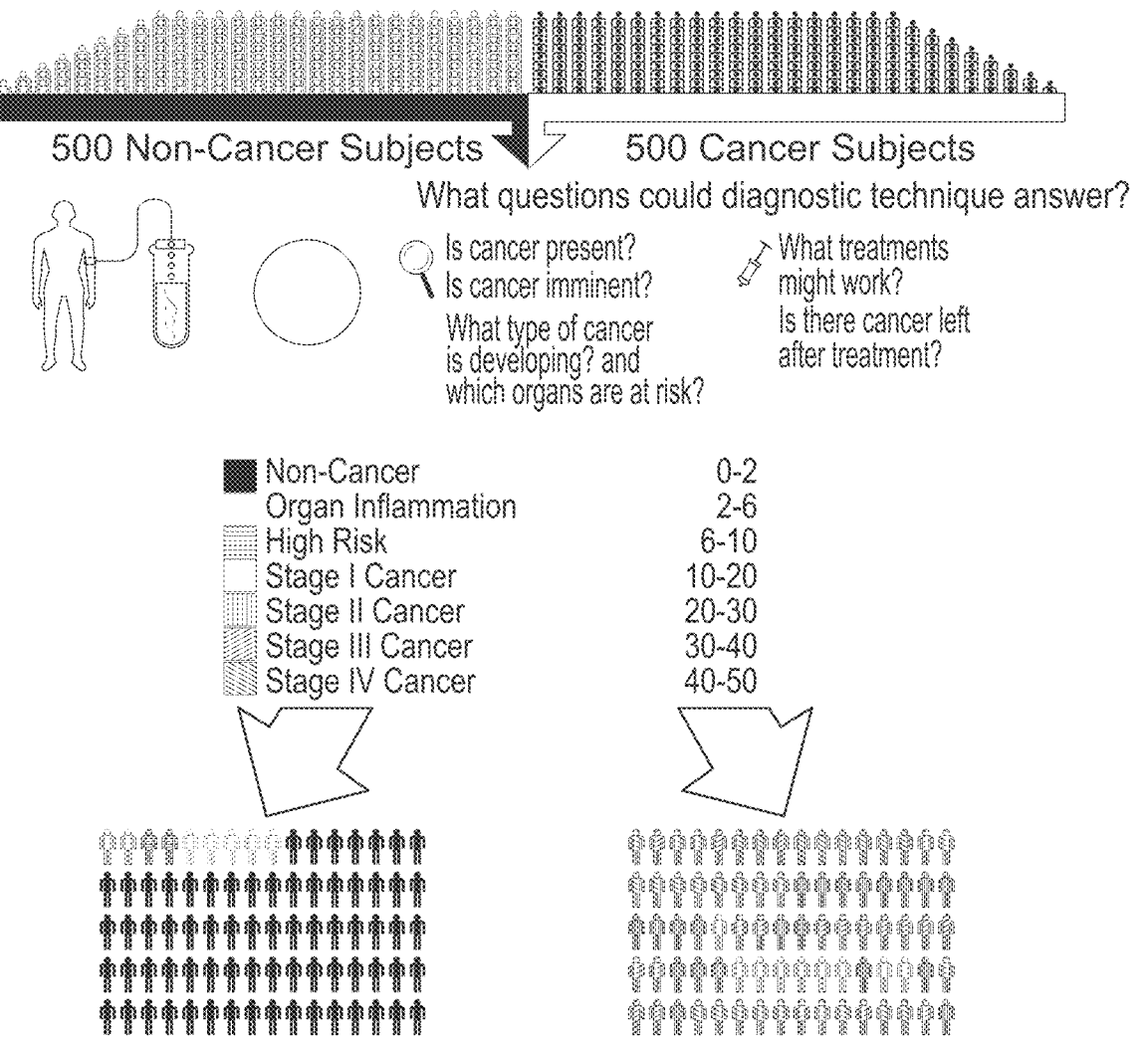

500 Non-Cancer Subjects  500 Cancer Subjects

What questions could diagnostic technique answer?

Is cancer present?  What treatments
Is cancer imminent?  might work?
 Is there cancer left
What type of cancer  after treatment?
is developing? and
which organs are at risk?

| Non-Cancer | 0-2 |
| Organ Inflammation | 2-6 |
| High Risk | 6-10 |
| Stage I Cancer | 10-20 |
| Stage II Cancer | 20-30 |
| Stage III Cancer | 30-40 |
| Stage IV Cancer | 40-50 |

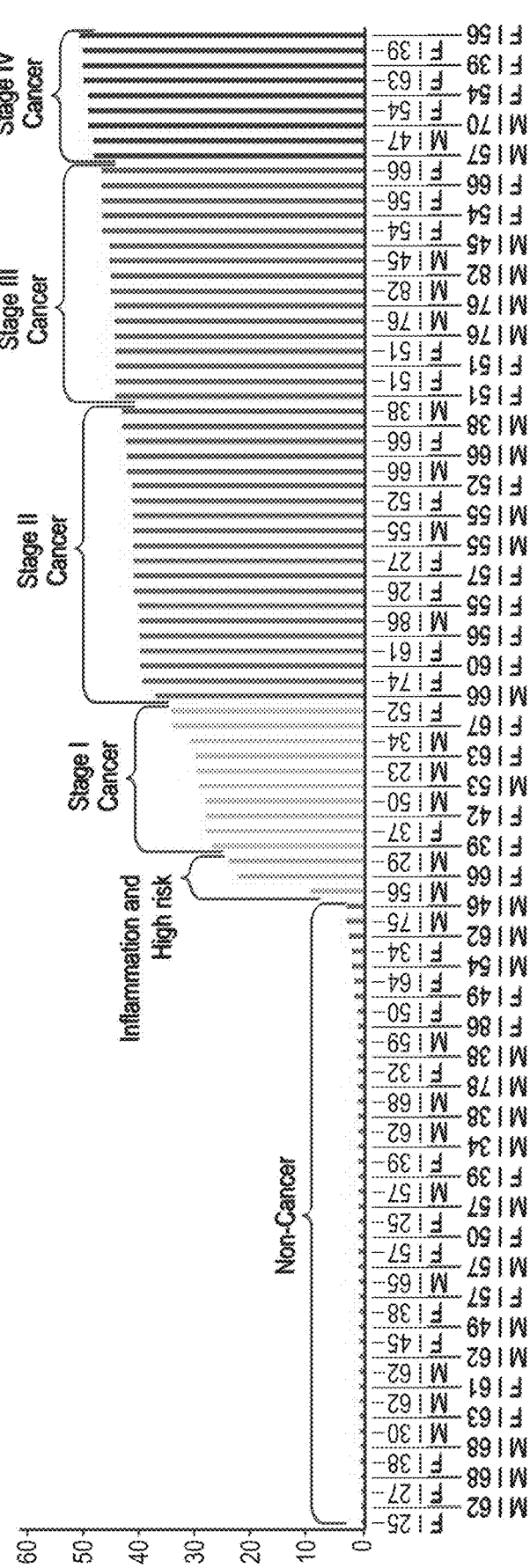
Figure 5 (continued)

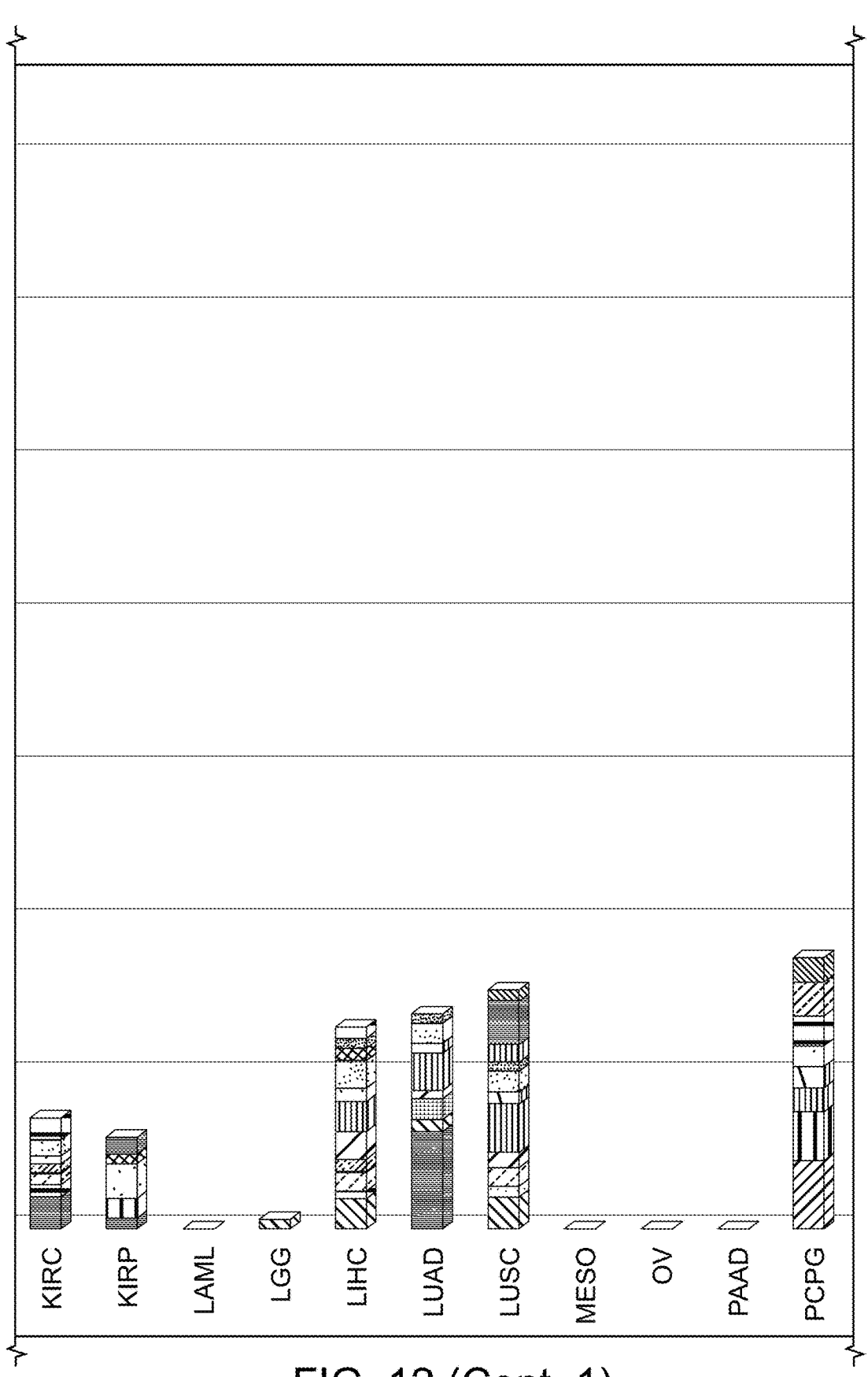
FIG. 12 (Cont. 1)

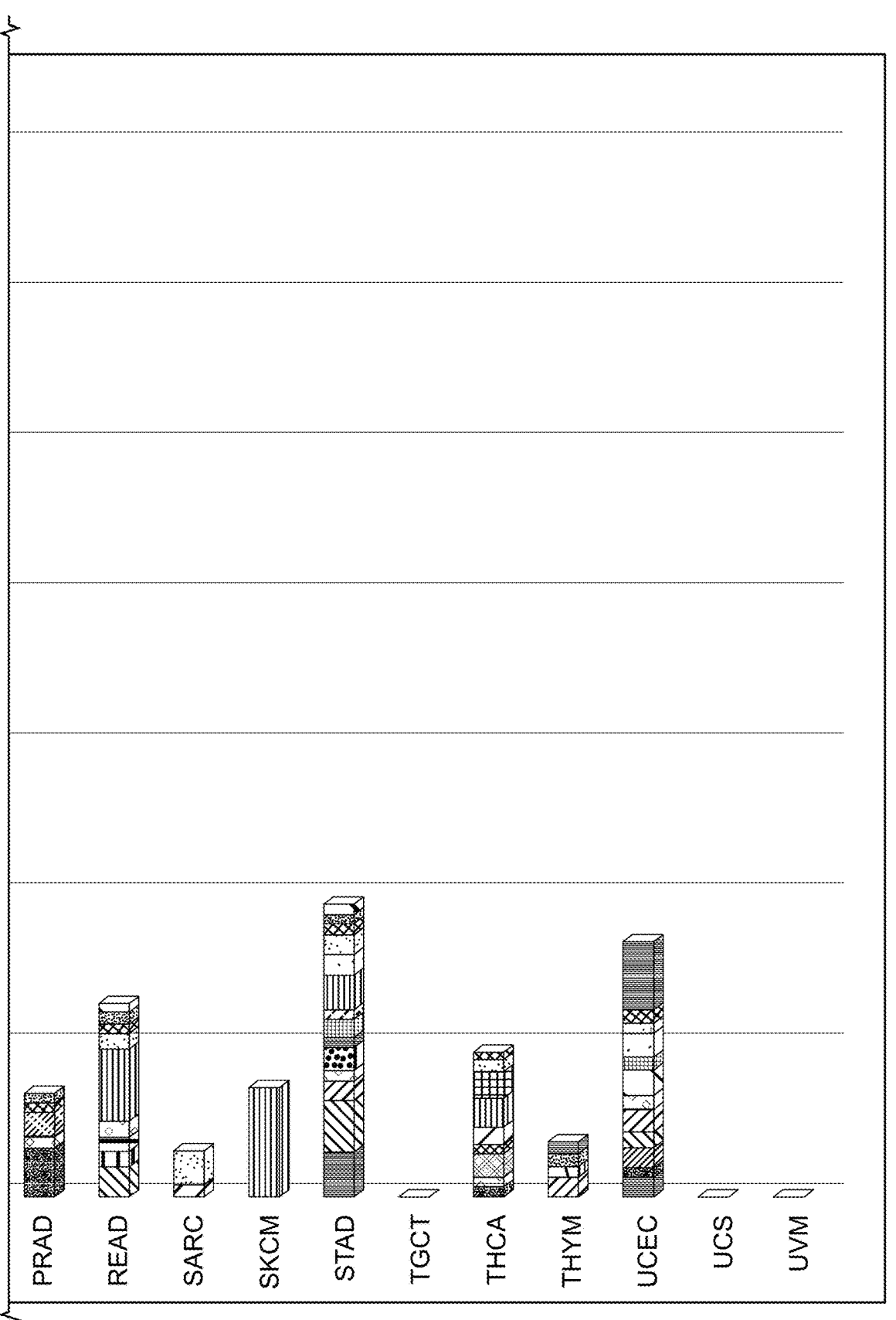
FIG. 12 (Cont. 2)

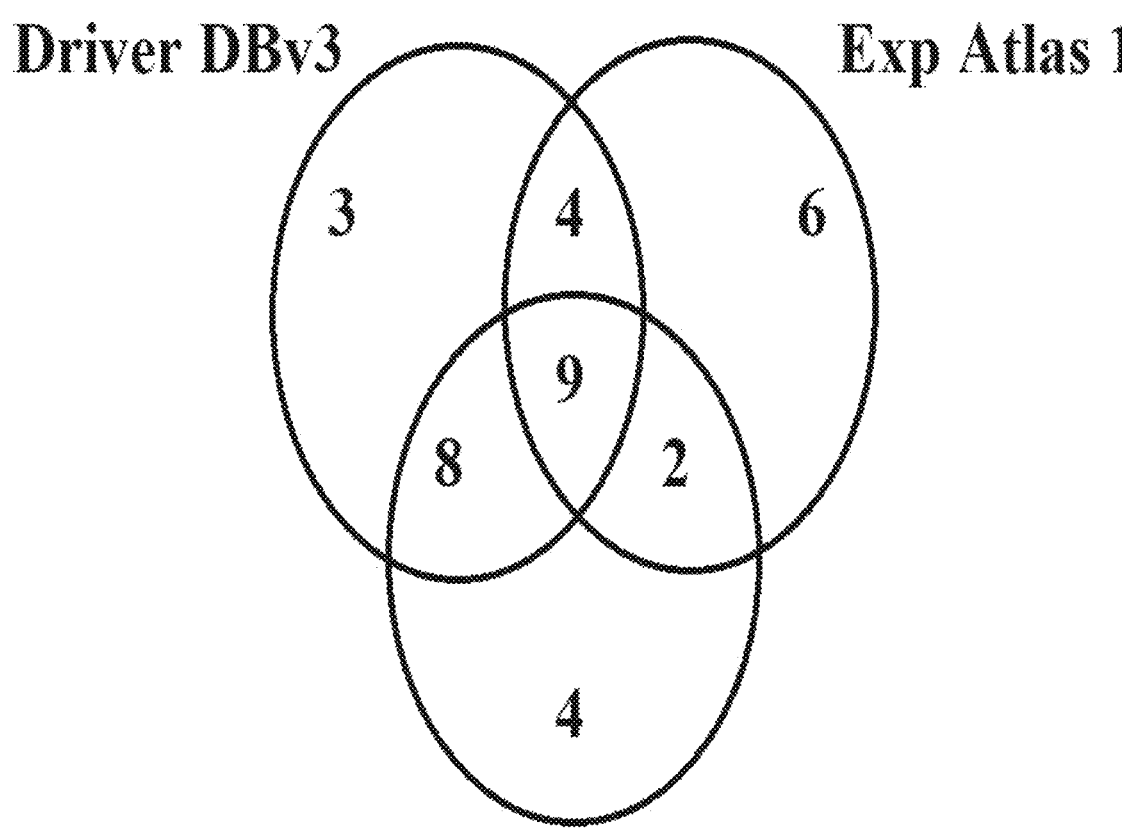
Driver DBv3
Exp Atlas 1
Exp Atlas 2
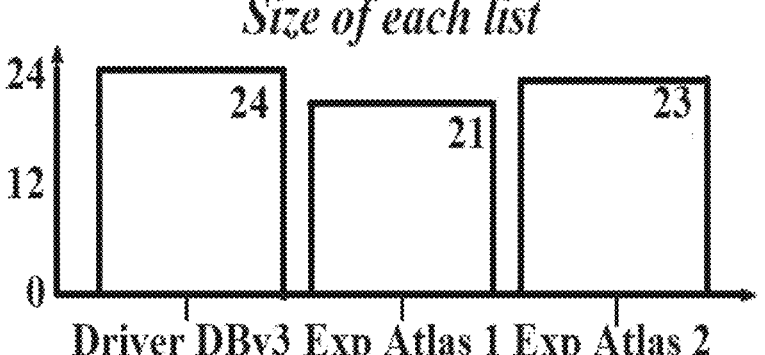
*Size of each list*
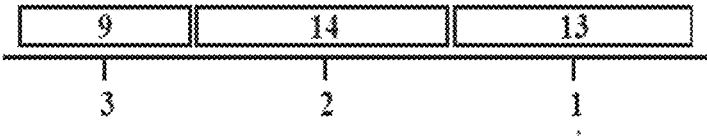
*Number of elements: specific (1) or shared by 2,3,...lists*
Figure 13

METHOD FOR IDENTIFYING CANCER IN A SUBJECT

CROSS-REFERENCE

This application claims the benefit of U.S. Provisional Application No. 63/041,413, filed Jun. 19, 2020, U.S. Provisional Application No. 63/109,073, filed Nov. 3, 2020, each of which is incorporated herein by reference in their entireties.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "56773_Seqlisting.txt", which was created on May 6, 2021 and is 2,336 bytes in size. The subject matter of the Sequence Listing is incorporated herein in its entirety by reference.

FIELD OF THE INVENTION

The present disclosure broadly relates to the field health-care technologies, and particularly provides a simplified method for detecting the presence or absence of a medical condition in a human subject. The method as disclosed herein also detects for the presence or absence of an inflammatory condition in the human subject from the blood sample. Further, the method as described in the present disclosure, also detects the presence, or absence, or imminent presence of cancer in a subject. The method as described herein is an in-vitro method which involves analysing the sample obtained from a human subject.

BACKGROUND OF INVENTION

Research on the genetic causes of disease has accelerated as a result of both the completion of the human genome and the development of the Next Generation Sequencing techniques, which has opened the promise of translating the alterations in individuals' genomes in clinically relevant information to assist disease diagnostics and therapeutic, clinical decision-making strategies. These efforts have generated a large volume of potentially useful information in form of enormous amounts of data that has boosted biomedical research. Application and interpretation of this information, however, is still cumbersome and time-consuming for researchers, because the clinically relevant molecular fingerprint of the mutation profiles is derived out of tissues extracted from biopsy procedures.

Biopsy is a well-known technique which involves removal of tissue under examination for disease diagnosis and further treatment approaches. Usually, a biopsy is invasive, and involves complex, surgical procedures for removal of tissue from their native environment. Tissue biopsy is the "gold standard" for cancer, but interestingly, a number of non-cancerous tissues (i.e. diseased tissues) are also excised in order to detect the origin, transmission, progression of disease etc. that dilutes the original disease data and leads to false positives including misdiagnosis. Almost all tissues can be studied through biopsy including muscle, thyroid, bladder, heart, prostate, skin, lung, lymph node, liver, kidney, nerves etc. Some diseases for which biopsies are included in the scientific literature are cortical demyelination in brain white matter lesions for early detection of multiple sclerosis (Lucchinetti et. al. 2011), percutaneous renal biopsy for kidney diseases, cirrhotic liver disease, hepatitis C-associated glomerulonephritis and cryoglobulinemic vasculitis, monoclonal gammopathy etc. (Hogan, Mocanu, and Berns 2016), synovial biopsy for detection of mononuclear infiltrates, fibrosis, angiogenesis, macrophage infiltration and lining layer thickening in tissues of osteoarthritis patients (Ene et al. 2015), shave, punch or incisional biopsy for inflammatory skin disorders (Harvey, Chan, and Wood 2017), computer-tomography guided lung biopsy for evaluation of COPD (Asai et al. 2013), myocardial biopsy (Francis and Lewis 2018), liver biopsy for cirrhotic patients (Sherman et al. 2007) etc. However, most tissue biopsies result in surgical complications, bleeding, and adverse side-effects etc. and hence are not recommended as opposed to biofluid tests such as of blood, urine, saliva etc. Tissue biopsies are difficult to perform, resulting in painful, often discomfort procedures that may not identify the exact anatomical location of the tumor or may further cause metastasis-promoting complications due to surgical excision of angiogenesis-rich areas. Owing to the complexities of the tissue biopsy procedure and mixed results obtained, and the lack of clarity associated with such studies with respect to the tissue to be studied vis-à-vis the condition of a subject, there is a knowledge gap which exists in this area of work.

Stem cells, particularly of embryonic origin, possess pluripotency markers viz. Oct4, Nanog, Sox2 and their isoforms are indicative of varied differentiation potentials into multiple tissues forming organs in development, homeostasis and aging. Since stem cells contribute to tissue development, they act as molecular biosensors implicative of tissue damage and injury, a hallmark of medical conditions. Thus, stem cell markers are prominent biomarkers for determining severity of medical conditions and identification of embryonic-like stem cell markers in body fluids can detect medical condition non-invasively.

Thus, there is a dire need in the art to deploy a method for determining severity of medical conditions and identification of embryonic-like stem cell markers in body fluids to detect medical condition non-invasively.

SUMMARY OF INVENTION

In an aspect of the present disclosure, there is provided an in-vitro method for detecting a medical condition in a subject, said method comprising: (a) obtaining a sample; (b) enriching very small embryonic like stem cells from the sample, to obtain a mixture comprising said very small embryonic like stem cells; (c) obtaining nucleic acid from the mixture of step (b); (d) performing an assay with the nucleic acid for analysing expression level of Oct4A in the very small embryonic like stem cells from the sample; and (e) comparing the expression level of Oct4A in the very small embryonic like stem cells from the sample with an expression level of Oct4A in a control sample, wherein an increase in the range of 1.1-3 folds in the expression level of Oct4A in the very small embryonic like stem cells from the sample as compared to the expression level of Oct4A in the control sample detects the presence of a medical condition in the subject.

In another aspect of the present disclosure, there is provided an in-vitro method for predicting onset of cancer in a subject, said method comprising: (a) obtaining a sample; (b) enriching very small embryonic like stem cells from the sample, to obtain a mixture comprising said very small embryonic like stem cells; (c) obtaining nucleic acid from the mixture of step (b); (d) performing an assay with the nucleic acid for analysing expression level of Oct4A in the very small embryonic like stem cells; and (e) comparing the expression level of Oct4A in the very small embryonic like stem cells from the sample with an expression level of Oct4A in a control sample, wherein an increase in the range of 3-5 folds in the expression level of Oct4A in the very small embryonic like stem cells from the sample as compared to the expression level of Oct4A in the control sample predicts the onset of cancer in the subject.

In another aspect of the present disclosure, there is provided an in-vitro method for detecting the presence of cancer in a subject, said method comprising: (a) obtaining a sample; (b) enriching very small embryonic like stem cells from the sample, to obtain a mixture comprising said very small embryonic like stem cells; (c) obtaining nucleic acid from the mixture of step (b); (d) performing an assay with the nucleic acid for analysing expression level of Oct4A in the very small embryonic like stem cells; and (e) comparing the expression level of Oct4A in the very small embryonic like stem cells from the sample with an expression level of Oct4A in a control sample, wherein an increase of at least 5 folds in the expression level of Oct4A in the very small embryonic like stem cells from the sample as compared to the expression level of Oct4A in the control sample detects the presence of cancer in the subject.

In another aspect of the present disclosure, there is provided an in-vitro method for monitoring response to anti-cancer therapy, said method comprising: (a) obtaining a sample at one time point during an anti-cancer therapy; (b) enriching very small embryonic like stem cells from the sample to obtain a mixture comprising said very small embryonic like stem cells; (c) obtaining nucleic acid from the mixture of step (b); (d) performing an assay with the nucleic acid for analysing expression level of Oct4A in the very small embryonic like stem cells from the sample; and (e) comparing the expression level of Oct4A in the very small embryonic like stem cells from the sample with an expression level of Oct4A in very small embryonic like stem cells in a reference that monitors the response to anti-cancer therapy.

In another aspect of the present disclosure, there is provided an in-vitro method for detecting a positive response to anti-cancer therapy, said method comprising: (a) obtaining a sample-I before administration of an anti-cancer therapy; (b) obtaining a sample-II after administration of the anti-cancer therapy; (c) enriching very small embryonic like stem cells from the sample-I to obtain a mixture-I comprising said very small embryonic like stem cells; (d) enriching very small embryonic like stem cells from the sample-II to obtain a mixture-II comprising said very small embryonic like stem cells; (e) obtaining nucleic acid-I from the mixture-I; (f) obtaining nucleic acid-II from the mixture-II; (g) independently performing an assay with the nucleic acid-I and the nucleic acid-II for analysing expression level of Oct4A; and (h) comparing the expression levels of Oct4A from the nucleic acid-II with the expression level of Oct4A from the nucleic acid-I, wherein a decrease in the expression level of Oct4A from the nucleic acid-II as compared to the expression level of Oct4A from the nucleic acid-I detects a positive response to the cancer treatment.

In another aspect of the present disclosure, there is provided an in-vitro method for detecting cancer, said method comprising: (a) obtaining a sample; (b) enriching very small embryonic like stem cells from the sample, to obtain a mixture comprising said very small embryonic like stem cells; (c) obtaining nucleic acid from the mixture of step (b); (d) performing an assay with the nucleic acid for analysing expression level of Oct4A in very small embryonic like stem cells; (e) comparing the expression level of Oct4A in very small embryonic like stem cells in the sample with an expression level of Oct4A in very small embryonic like stem cells in a control sample, wherein an increase in the expression level of Oct4A in very small embryonic like stem cells in the sample by >5 fold as compared to the expression level of Oct4A in very small embryonic like stem cells in the control sample indicates presence of cancer; and (f) performing sequence-based assays on the nucleic acid and analysing for mutation in at least one cancer-related marker, wherein presence of mutation in the at least one cancer-related marker indicates presence of a specific type of cancer based on the cancer-related marker analysed.

In another aspect of the present disclosure, there is provided a method for treating cancer, said method comprising: (a) obtaining a sample from a subject; (b) enriching very small embryonic like stem cells from the sample, to obtain a mixture comprising said very small embryonic like stem cells; (c) obtaining nucleic acid from the mixture of step (b); (d) performing an assay with the nucleic acid for analysing expression level of Oct4A in very small embryonic like stem cells; (e) comparing the expression level of Oct4A in very small embryonic like stem cells in the sample with an expression level of Oct4A in a control sample, wherein an increase in the expression level of Oct4A in very small embryonic like stem cells in the sample >5 fold as compared to the expression level of Oct4A in the control sample detects cancer; and (f) administering anti-cancer therapy to the subject for treating cancer.

In another aspect of the present disclosure, there is provided an in-vitro method for grading cancer in a subject, said method comprising: (a) obtaining a sample; (b) enriching very small embryonic like stem cells from the sample, to obtain a mixture comprising said very small embryonic like stem cells; (c) obtaining nucleic acid from the mixture of step (b); (d) performing an assay with the nucleic acid for analysing expression level of Oct4A in the very small embryonic like stem cells; and (e) comparing the expression level of Oct4A in the very small embryonic like stem cells from the sample with an expression level of Oct4A in a control sample, wherein an increase in the range of 5-10 folds in the expression level of Oct4A in the very small embryonic like stem cells from the sample as compared to the expression level of Oct4A in the control sample is indicative of stage I cancer in the subject.

In another aspect of the present disclosure, there is provided an in-vitro method for grading cancer in a subject, said method comprising: (a) obtaining a sample; (b) enriching very small embryonic like stem cells from the sample, to obtain a mixture comprising said very small embryonic like stem cells; (c) obtaining nucleic acid from the mixture of step (b); (d) performing an assay with the nucleic acid for analysing expression level of Oct4A in the very small embryonic like stem cells; and (e) comparing the expression level of Oct4A in the very small embryonic like stem cells from the sample with an expression level of Oct4A in a control sample, wherein an increase in the range of 10-15 folds in the expression level of Oct4A in the very small embryonic like stem cells from the sample as compared to the expression level of Oct4A in the control sample is indicative of stage II cancer in the subject.

In another aspect of the present disclosure, there is provided an in-vitro method for grading cancer in a subject, said method comprising: (a) obtaining a sample; (b) enriching very small embryonic like stem cells from the sample, to obtain a mixture comprising said very small embryonic like stem cells; (c) obtaining nucleic acid from the mixture of step (b); (d) performing an assay with the nucleic acid for analysing expression level of Oct4A in the very small embryonic like stem cells; and (e) comparing the expression level of Oct4A in the very small embryonic like stem cells from the sample with an expression level of Oct4A in a control sample, wherein an increase in the range of 15-20 folds in the expression level of Oct4A in the very small embryonic like stem cells from the sample as compared to the expression level of Oct4A in the control sample is indicative of stage III cancer in the subject.

In another aspect of the present disclosure, there is provided an in-vitro method for grading cancer in a subject, said method comprising: (a) obtaining a sample; (b) enriching very small embryonic like stem cells from the sample, to obtain a mixture comprising said very small embryonic like stem cells; (c) obtaining nucleic acid from the mixture of step (b); (d) performing an assay with the nucleic acid for analysing expression level of Oct4A in the very small embryonic like stem cells; and (e) comparing the expression level of Oct4A in the very small embryonic like stem cells from the sample with an expression level of Oct4A in a control sample, wherein an increase in the range of 20 to higher folds in the expression level of Oct4A in the very small embryonic like stem cells from the sample as compared to the expression level of Oct4A in the control sample is indicative of stage IV cancer in the subject.

In an aspect of the present disclosure, there is provided an in-vitro method for detecting a medical condition in a subject, said method comprising: (a) obtaining a blood sample; (b) enriching very small embryonic-like stem cells from the sample, to obtain a mixture comprising said cells; (c) obtaining nucleic acid from the mixture of step (b); (d) performing an assay with the nucleic acid for analysing methylation level of Oct4A in the cells; and (e) comparing the methylation level of Oct4A in the cells from the sample with the methylation level of Oct4A in a control sample, wherein a modulation in the methylation level of Oct4A in the cells from the sample as compared to the methylation level of Oct4A in the control sample is indicative of a medical condition in the subject.

In an aspect of the present disclosure, there is provided an in-vitro method for detecting cancer in a subject, said method comprising: (a) obtaining a blood sample; (b) enriching cells from the sample, to obtain a mixture comprising said cells; (c) obtaining nucleic acid from the mixture of step (b); (d) performing an assay with the nucleic acid for analysing methylation level of Oct4A in the cells; and (e) comparing the methylation level of Oct4A in the cells from the sample with the methylation level of Oct4A in a control sample, wherein a modulation in the methylation level of Oct4A in the cells from the sample as compared to the methylation level of Oct4A in the control sample is indicative of cancer in the subject.

In another aspect of the present disclosure, there is provided an in-vitro method for detecting cancer, said method comprising: (a) obtaining a blood sample; (b) enriching very small embryonic-like stem cells from the sample, to obtain a mixture comprising said cells; (c) isolating mitochondria from the cells; (d) obtaining nucleic acid from the mixture of step (c); and (e) performing sequence-based assays on the nucleic acid and analysing for mutation in at least one cancer-related marker, wherein presence of mutation in the at least one cancer-related marker that may or may not modulate nuclear Oct4A levels indicates presence of a specific type of cancer based on the cancer-related marker analysed.

In another aspect of the present disclosure, there is provided a method for detecting presence of cancer in a subject, said method comprising: (a) obtaining a blood sample from a subject; (b) enumerating the number of very small embryonic like stem cells in the blood sample; and (c) comparing the number of very small embryonic like stem cells in the blood sample with the number of very small embryonic like stem cells in a control blood sample, wherein an increase in the number of very small embryonic like stem cells in the blood sample as compared to the number of very small embryonic like stem cells in a control blood sample detects the presence of cancer in the subject.

In another aspect of the present disclosure, there is provided a method for predicting the onset of cancer in a subject, said method comprising: (a) obtaining a blood sample from a subject; (b) enumerating the number of very small embryonic like stem cells in the blood sample; and (c) comparing the number of very small embryonic like stem cells in the blood sample with the number of very small embryonic like stem cells in a control blood sample, wherein an increase in the number of very small embryonic like stem cells in the blood sample as compared to the number of very small embryonic like stem cells in a control blood sample predicts the onset of cancer in the subject.

In another aspect of the present disclosure, there is provided a method for detecting the presence of a medical condition in a subject, said method comprising: (a) obtaining a blood sample from a subject; (b) enumerating the number of very small embryonic like stem cells in the blood sample; and (c) comparing the number of very small embryonic like stem cells in the blood sample with the number of very small embryonic like stem cells in a control blood sample, wherein an increase in the number of very small embryonic like stem cells in the blood sample as compared to the number of very small embryonic like stem cells in a control blood sample detects the presence of a medical condition in the subject.

In another aspect of the present disclosure, there is provided a method for detecting presence of cancer in a subject, said method comprising: (a) enumerating in-vivo the number of very small embryonic like stem cells in the blood of a subject; and (b) comparing the number of very small embryonic like stem cells in the subject with the number of very small embryonic like stem cells in a control, wherein an increase in the number of very small embryonic like stem cells in the subject as compared to the number of very small embryonic like stem cells in a control detects the presence of cancer in the subject.

In another aspect of the present disclosure, there is provided a method for predicting the onset of cancer in a subject, said method comprising: (a) enumerating in-vivo the number of very small embryonic like stem cells in the blood of a subject; and (b) comparing the number of very small embryonic like stem cells in the subject with the number of very small embryonic like stem cells in a control, wherein an increase in the number of very small embryonic like stem cells in the subject as compared to the number of very small embryonic like stem cells in a control predicts the onset of cancer in the subject.

In another aspect of the present disclosure, there is provided a method for detecting presence of a medical condition in a subject, said method comprising: (a) enumerating in-vivo the number of very small embryonic like stem cells in the blood of a subject; and (b) comparing the number of very small embryonic like stem cells in the subject with the number of very small embryonic like stem cells in a control, wherein an increase in the number of very small embryonic like stem cells in the subject as compared to the number of very small embryonic like stem cells in a control detects the presence of medical condition in the subject.

In another aspect of the present disclosure, there is provided a detection kit comprising: (a) primer set for analysing expression level of at least one biomarker selected from the group consisting of Oct4A, Stella, and Fragilis in a mixture comprising very small embryonic-like stem cell; (b) reagents for performing quantitative PCR assay; (c) reagents for performing whole genome or exome or transcriptome sequencing; and (d) at least one tissue-specific array for analysing a sequence profile.

These and other features, aspects, and advantages of the present subject matter will be better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter.

BRIEF DESCRIPTION OF ACCOMPANYING DRAWINGS

The following drawings form a part of the present specification and are included to further illustrate aspects of the present disclosure. The disclosure may be better understood by reference to the drawings in combination with the detailed description of the specific embodiments presented herein.

FIG. 1 depicts the HrC scale (scale correlating the expression of Oct4A from VSELs to the medical condition) showing different ranges which were found to correlate with different stages of cancer, in accordance with an implementation of the present disclosure.

FIG. 2 depicts the distribution of types of cancer patients enrolled in the study, in accordance with an implementation of the present disclosure.

Figure 4A:
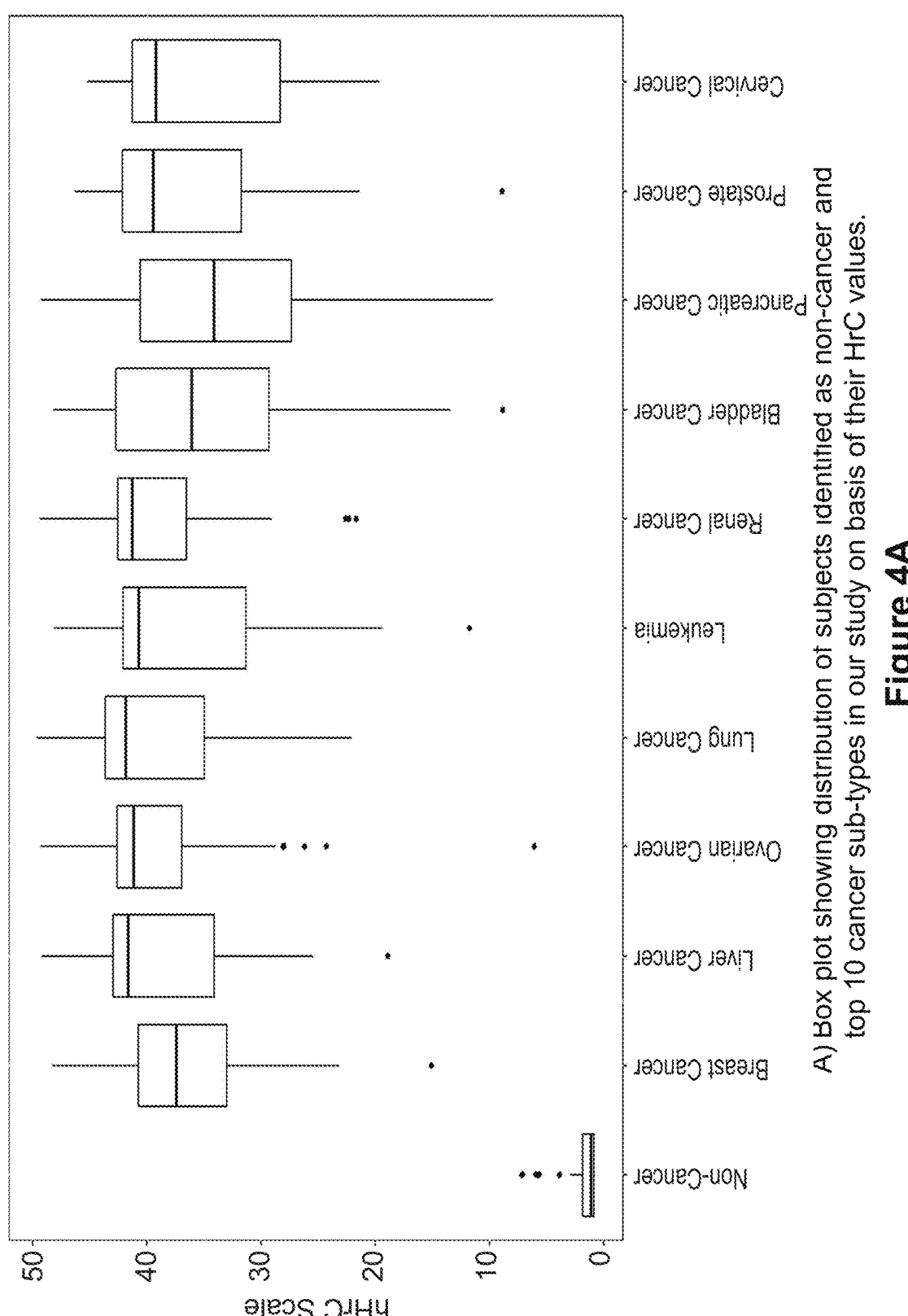
Figure 4B:
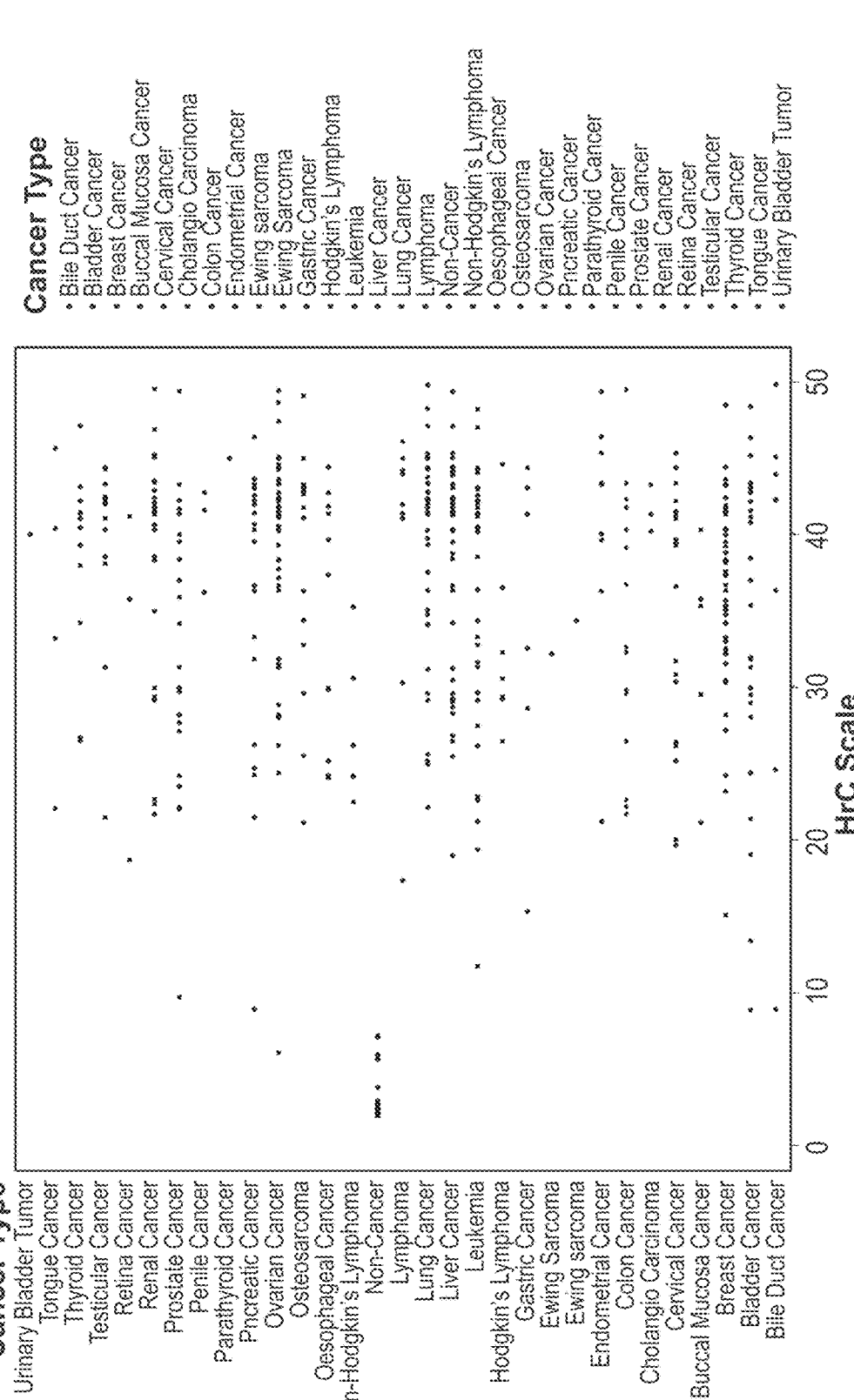
Figure 4C:
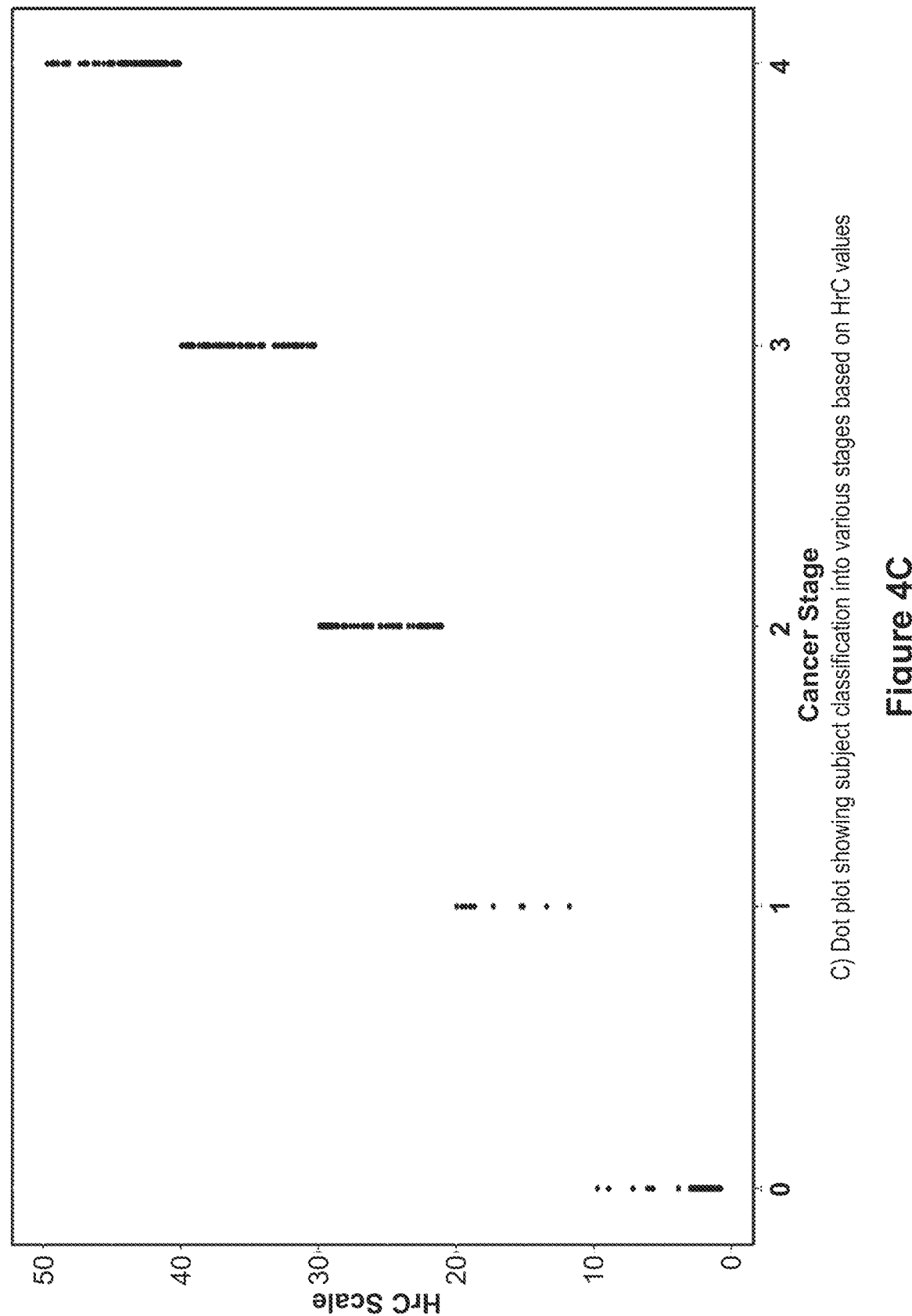

FIG. 4A depicted a Box plot showing a distribution of subjects identified as non-cancer and top 10 cancer subtypes on the basis of HrC values. FIG. 4B depicts a Dot plot showing a distribution of subjects identified as non-cancer and cancer subtypes on the basis of HrC values. FIG. 4C plot depicts a Dot plot showing a subject classification into various stages based on HrC values.

FIG. 5 depicts the representative infographic image summarizes the process of clinical study screening, recruitment, distribution, analysis, and interpretation. Representative data obtained in the study by studying the study subjects and classifying based on the HrC values. Graph represents the distribution of subjects aligned on the basis of their HrC values in ascending order. They were identified as non-cancer, inflammation & high risk, Stage I cancer, stage II cancer, stage III cancer and stage IV cancer, in accordance with an implementation of the present disclosure.

Figure 6:
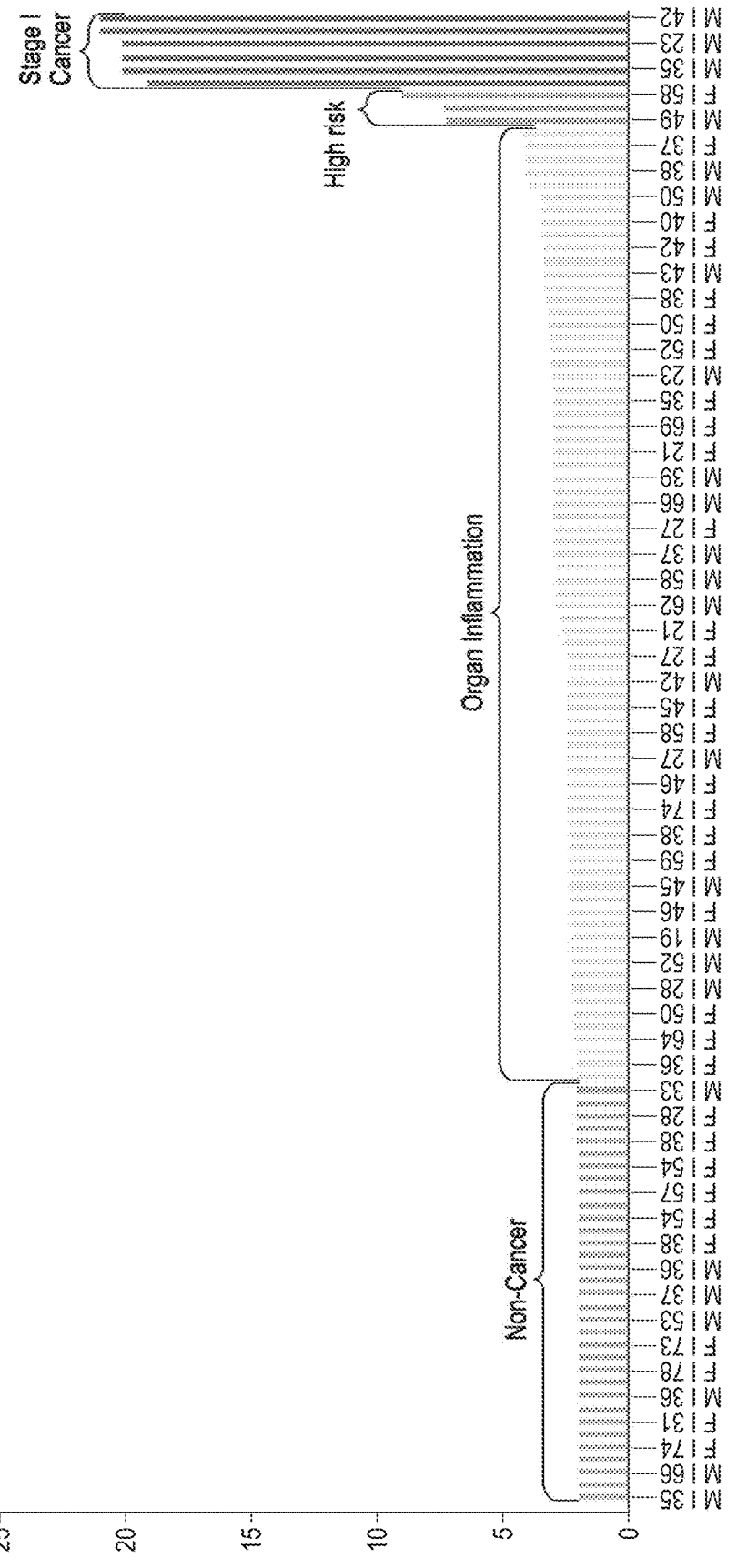

FIG. 6 depicts the distribution of subjects aligned on the basis of their HrC values arranged in ascending order and identified as non-cancer, Inflammation, high risk and Stage I cancer, in accordance with an implementation of the present disclosure.

Figure 7:
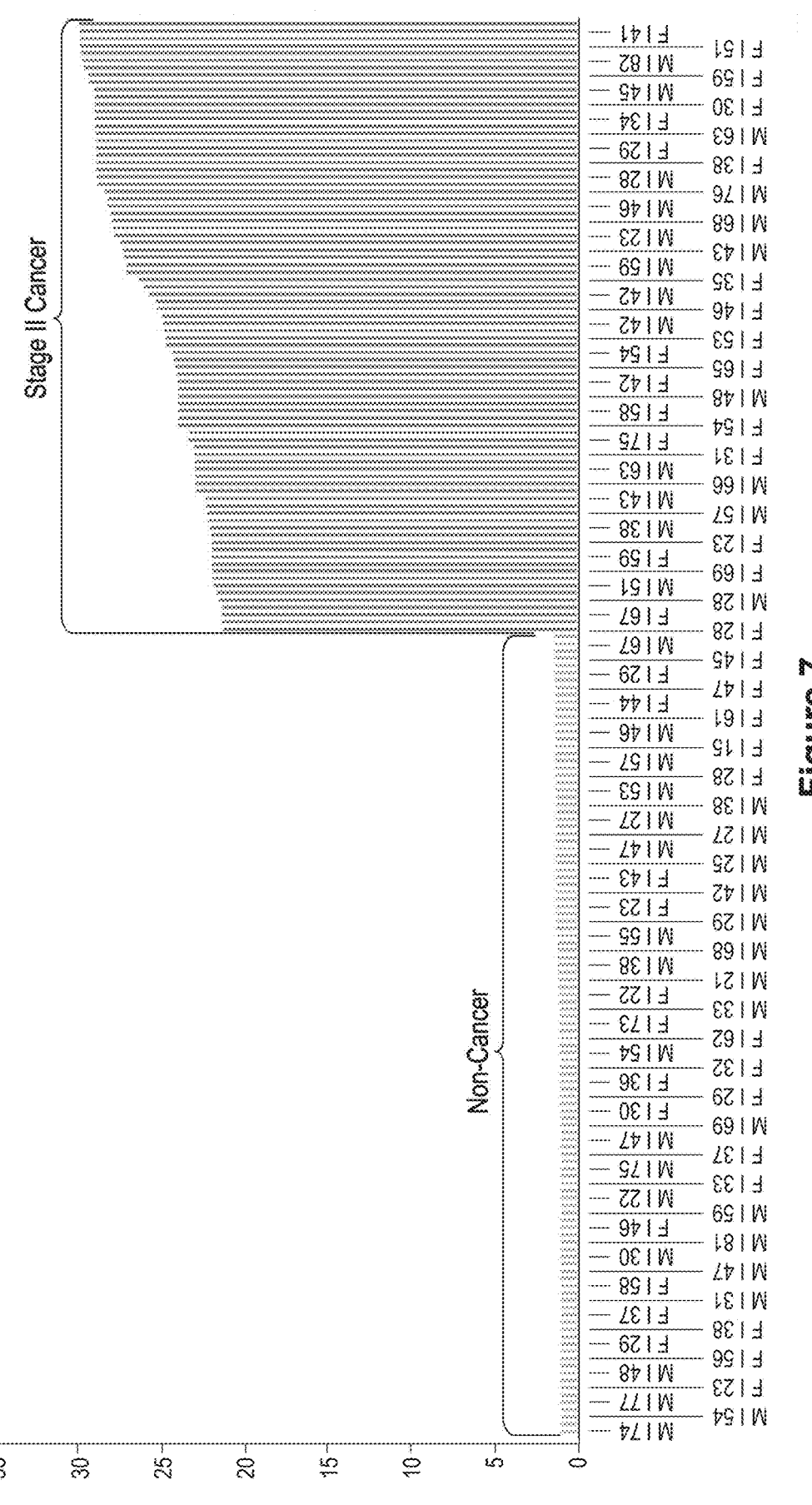

FIG. 7 depicts the distribution of subjects aligned on the basis of their HrC values arranged in ascending order and identified as non-cancer and stage II cancer, in accordance with an implementation of the present disclosure.

Figure 8:
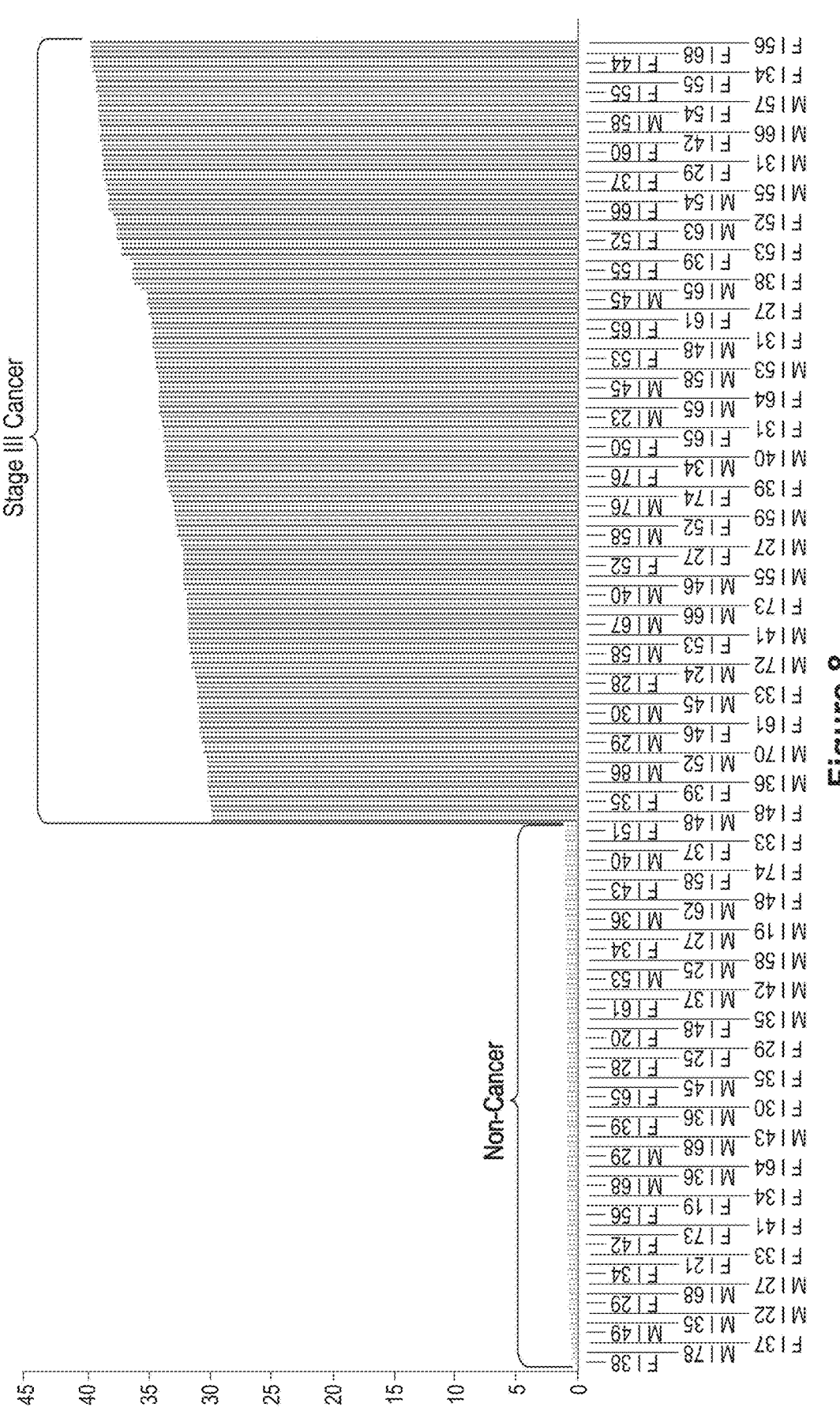

FIG. 8 depicts the distribution of subjects aligned on the basis of their HrC values arranged in ascending order and identified as non-cancer and stage III cancer, in accordance with an implementation of the present disclosure.

Figure 9:
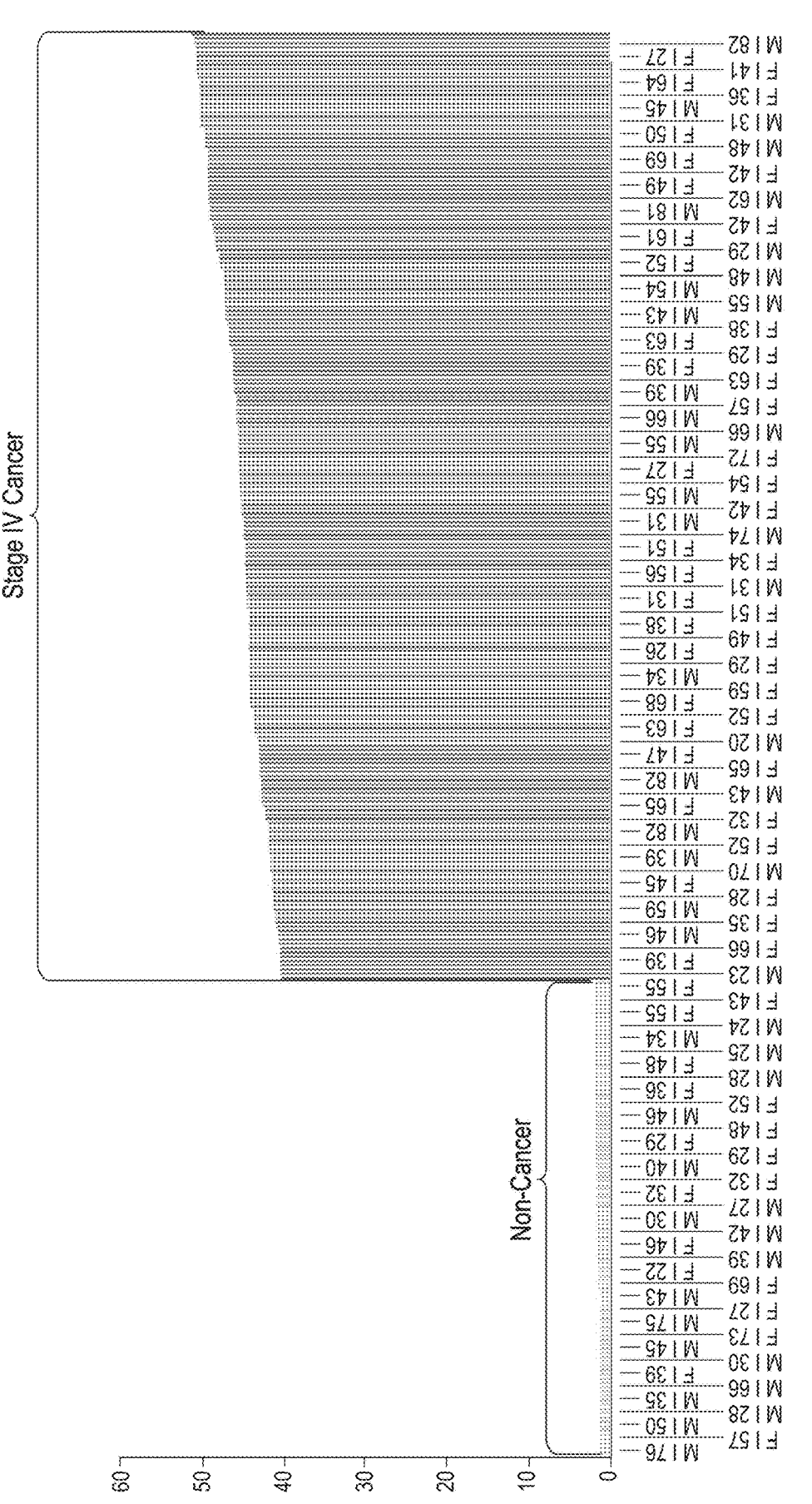

FIG. 9 depicts the distribution of subjects aligned on the basis of their HrC values arranged in ascending order and identified as non-cancer and stage IV cancer, in accordance with an implementation of the present disclosure.

Figure 10:
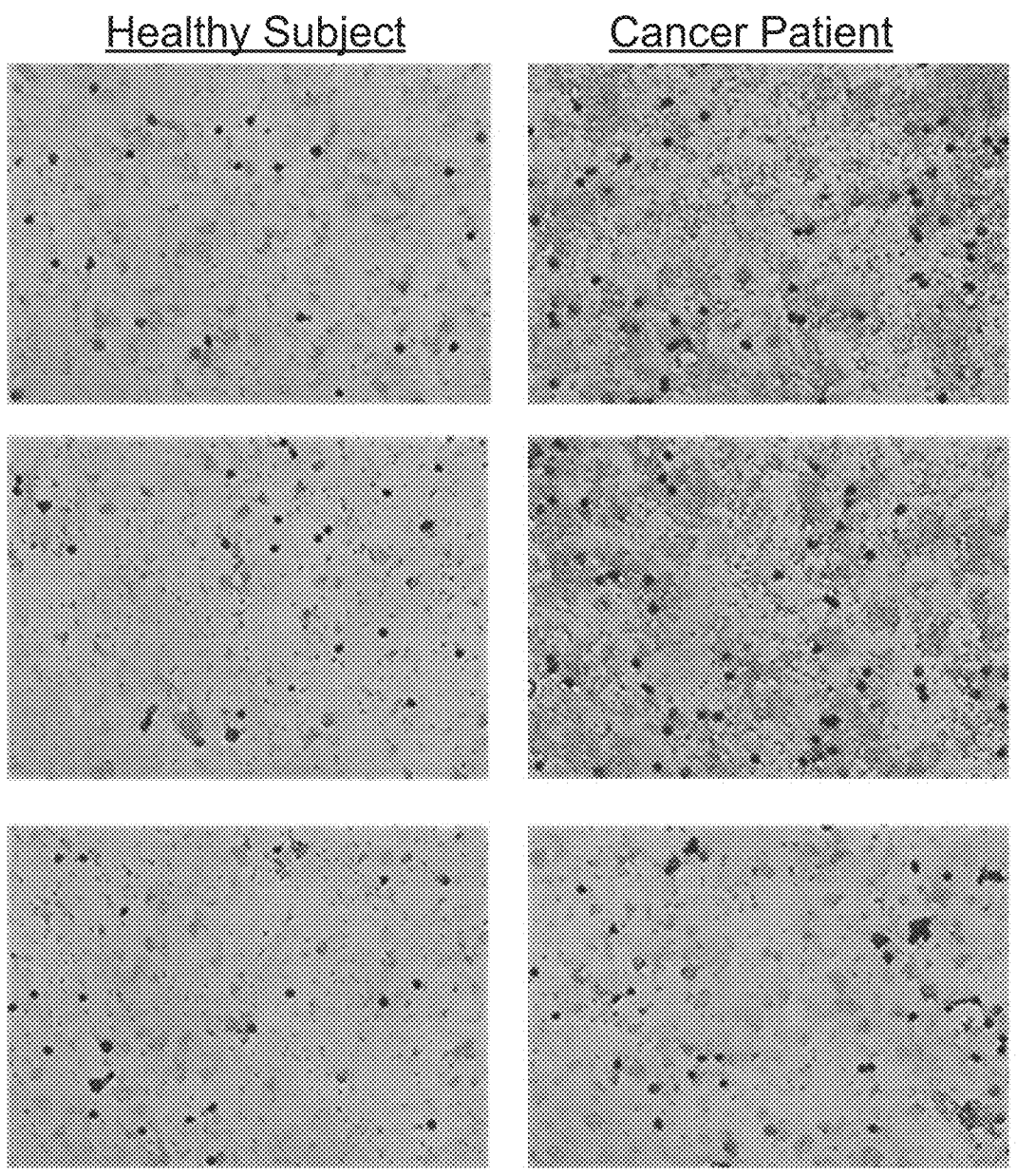

FIG. 10 depicts the comparative analysis of the number of very embryonic like stem cells (VSELs) obtained from the blood a healthy subject and a cancer patient, in accordance with an implementation of the present disclosure.

Figure 11:
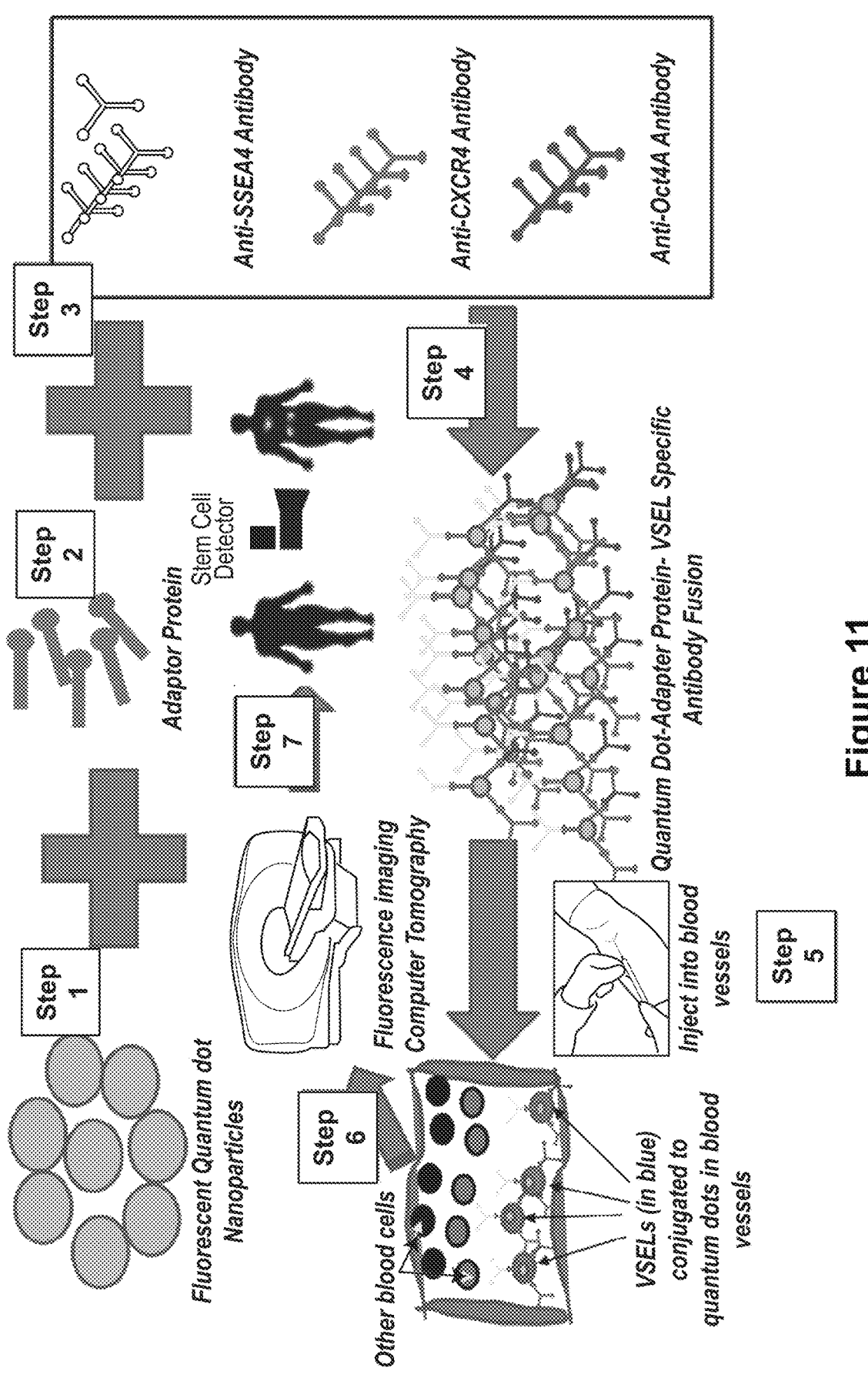

FIG. 11 depicts the modalities for quantifying the VSELs in a subject in-vivo for correlating it with a medical condition of the subject, in accordance with an implementation of the present disclosure.

Figure 12:
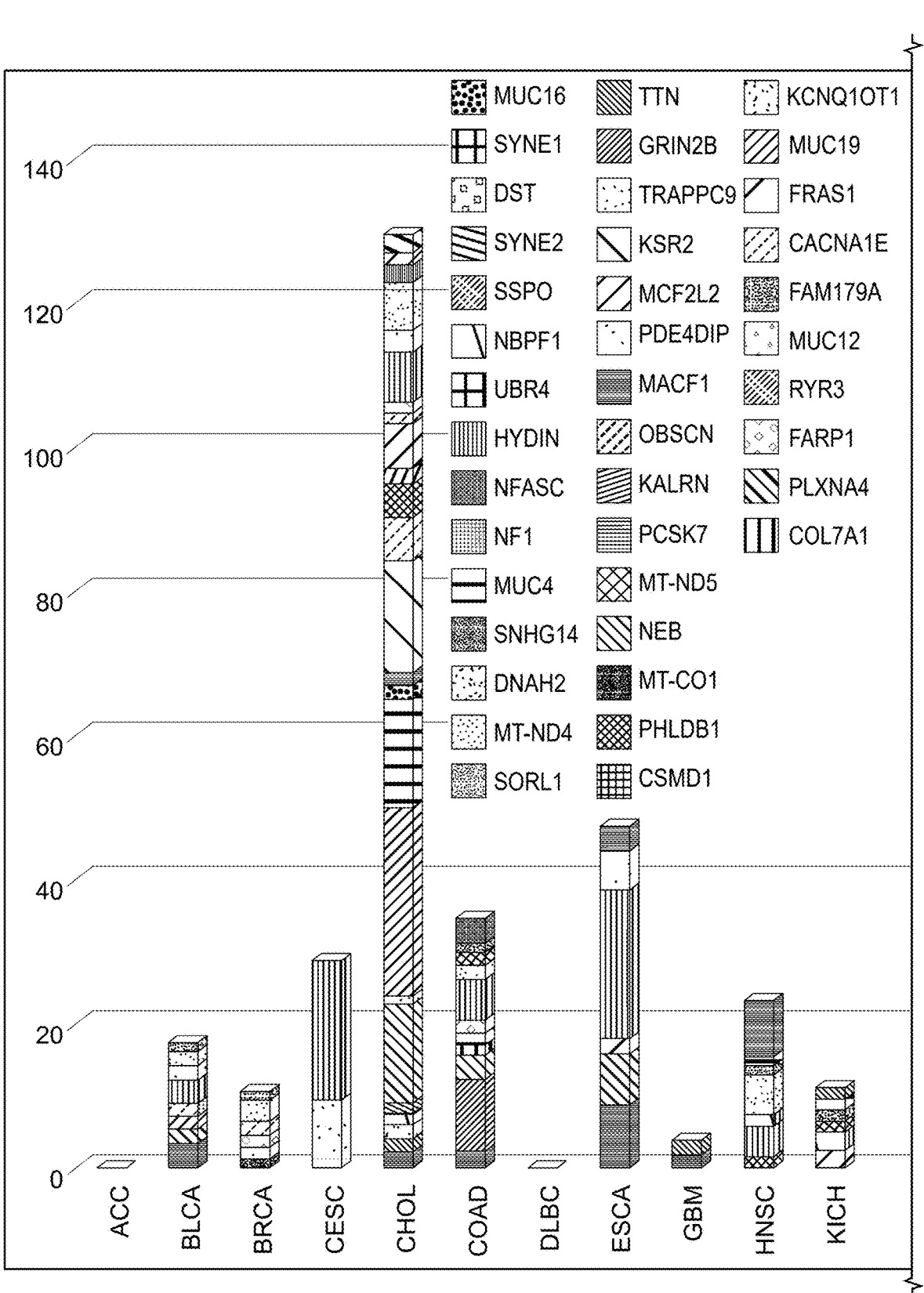

FIG. 12 depicts the expression profiles of top 56 genes (obtained as per blood-based genetic test) across 33 cancer types based on TCGA data using DriverDBv3 database, in accordance with an implementation of the present disclosure, in accordance with an implementation of the present disclosure.

FIG. 13 depicts the expression profiles of top 56 genes (obtained as per blood-based genetic test) across 33 cancer types based on 3 cancer genomic databases. Data was plotted using jvenn, in accordance with an implementation of the present disclosure.

Figure 14:
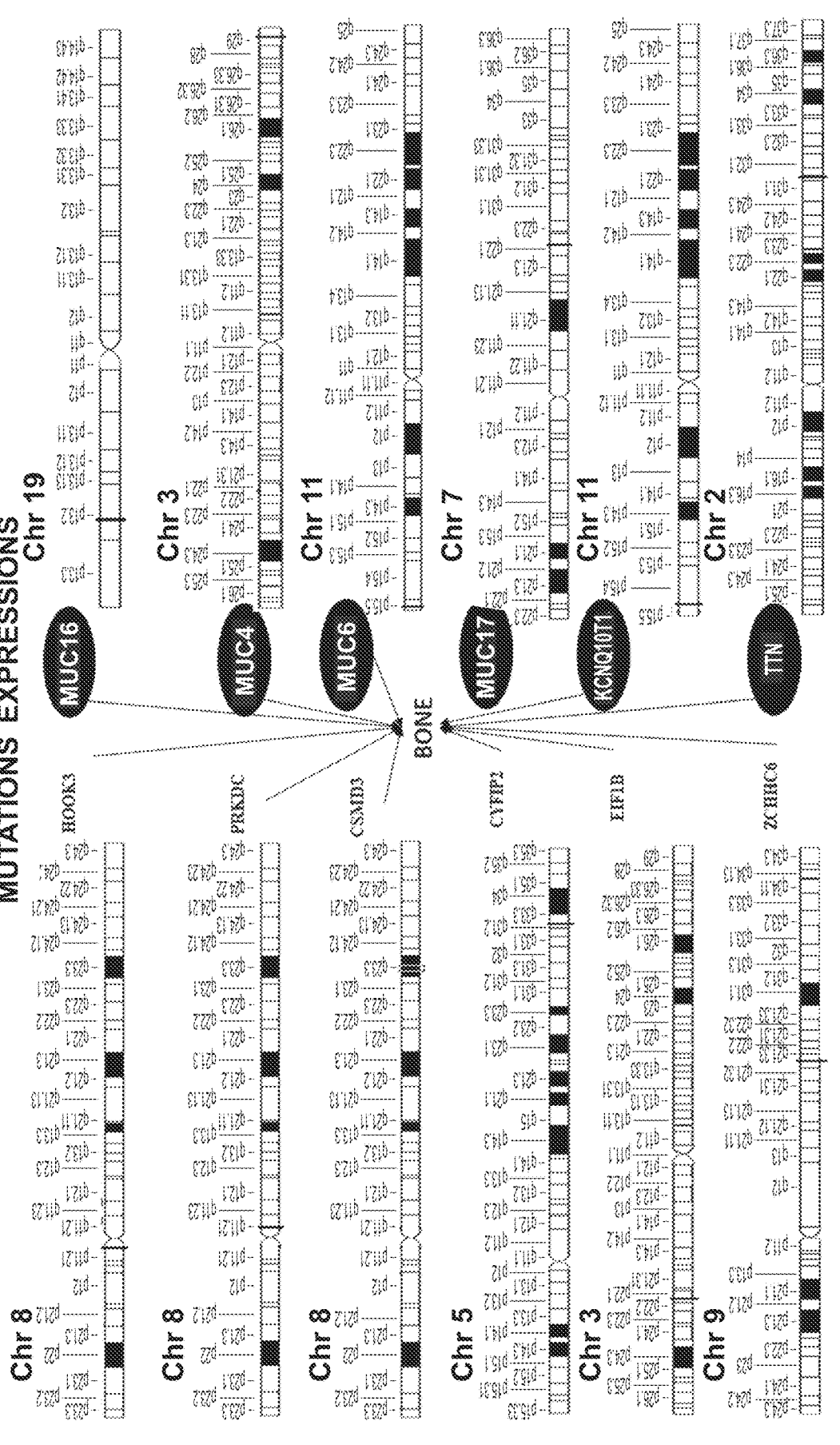

FIG. 14 depicts expression profiles of top mucin genes and mutations (obtained as per blood-based genetic test) across biopsies of osteosarcoma patients, in accordance with an implementation of the present disclosure.

DETAILED DESCRIPTION OF THE INVENTION

Those skilled in the art will be aware that the present disclosure is subject to variations and modifications other than those specifically described. It is to be understood that the present disclosure includes all such variations and modifications. The disclosure also includes all such steps, features, compositions, and compounds referred to or indicated in this specification, individually or collectively, and any and all combinations of any or more of such steps or features.

Definitions

For convenience, before further description of the present disclosure, certain terms employed in the specification, and examples are delineated here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only".

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

The term "control sample" refers to a sample from a healthy subject. The sample is to be a blood sample or a urine sample or a tissue sample or a sputum sample.

The control sample is to refer to VSELs obtained from the respective sample in order to enable the comparison of Oct4A expression level of VSELs obtained from a sample with the VSELs obtained from a control sample. Alternatively, the "control sample" refers to expression of housekeeping gene (for instance 18S rRNA) in VSELs of concerned subject of interest. However, it can be contemplated that a person skilled in the art can involve any housekeeping genes selected from 18S rRNA, ACTB, ATP5B, CyC1, EIF4A2, GAPDH, RPL13A, SDHA, TOP1, UBC, YWHAZ, PGK1, PPIA, RPLP0, ARBP, B2M, TFRC, GUSB, HMBS, HPRT1, TBP as a control.

The term "medical condition" includes all disorders, lesions, diseases, injury, genetic or congenital, or a biological or psychological condition that lies outside the range of normal, age-appropriate human variation.

The term "cancer" refers to the physiological condition in mammals that is characterized by unregulated cell growth. The term "cancer" as used in the present disclosure is intended to include benign, malignant cancers, dormant tumors, or micrometastasis. The types of cancer include, but are not limited to, carcinoma, lymphoma, blastoma (including medulloblastoma and retinoblastoma), sarcoma (including liposarcoma and synovial cell sarcoma), neuroendocrine tumors (including carcinoid tumors, gastrinoma, and Islet cell cancer), mesothelioma, schwannoma (including acoustic neuroma), meningioma, adenocarcinoma, melanoma, and leukemia or lymphoid malignancies. More particular examples of cancers include breast cancer, liver cancer, ovarian cancer, lung cancer, leukemia, prostate cancer, lymphoma, pancreatic cancer, cervical cancer, colon cancer, osteosarcoma, testicular cancer, thyroid cancer, gastric cancer, Ewing sarcoma, bladder cancer, gastrointestinal stromal tumor (GIST), kidney cancer (e.g., renal cell carcinoma), squamous cell cancer (e.g. epithelial squamous cell cancer), lung cancer (including small-cell lung cancer (SCLC), non-small cell lung cancer (NSCLC), adenocarcinoma of the lung, and squamous carcinoma of the lung), cancer of the peritoneum, hepatocellular cancer, gastric or stomach cancer including gastrointestinal cancer, pancreatic cancer, glioblastoma, cervical cancer, ovarian cancer, liver cancer, hepatoma, breast cancer (including metastatic breast cancer), bladder cancer, colon cancer, rectal cancer, colorectal cancer, endometrial or uterine carcinoma, salivary gland carcinoma, prostate cancer, vulval cancer, thyroid cancer, hepatic carcinoma, anal carcinoma, penile carcinoma, Merkel cell cancer, mycoses fungoids, testicular cancer, esophageal cancer, tumors of the biliary tract, head and neck cancer, as well as B-cell lymphoma (including low grade/follicular non-Hodgkin's lymphoma (NHL); small lymphocytic (SL) NHL; intermediate grade/follicular NHL; inter mediate grade diffuse NHL; high grade immunoblastic NHL; high grade lymphoblastic NHL; high grade small non-cleaved cell NHL; bulky disease NHL, mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

The term "detects" or "detection" refers to a detection which has been performed outside of a living patient using a sample from the patient.

The term "predicts" or "prediction" refers to an action of knowing something that will happen in future or in due course of time.

The term "blood sample" refers to the whole blood sample that is obtained from a subject. The scope of the method as disclosed herein begins from the stage of having obtained the blood sample, the method does not involve any invasive techniques, neither does it involve operating upon a subject. The term "blood sample" encompasses to include any form of processed blood sample also. By processing, the present disclosure intends to cover any method for enriching a specific population of cells or a mere processing so as to enable the blood sample to be used for testing by "in-vitro" methods.

The term "in-vitro" refers to a task or method or experiment being performed or taking place in a test tube, culture dish, or elsewhere outside a living organism.

The term "very small embryonic-like stem cell" or "VSELs" refers to a cell which is a type of pluripotent stem cell that is well-known in the art. The VSELs as per the present disclosure, are lesser than 7 microns in size.

The term "cell-free normal or tumor DNA" or "cfDNA" refers to type of nucleic acid circulating in the blood obtained from non-pluripotent or pluripotent cells that is well-known in the art.

The term "circulating tumor DNA" or "ctDNA" refers to type of nucleic acid of tumor cells circulating in the blood obtained from non-pluripotent/pluripotent cells that is well-known in the art.

The term "cell-free normal or tumor RNA" or "cfRNA" refers to type of nucleic acid circulating in the blood obtained from non-pluripotent/pluripotent cells that is well-known in the art.

The term "circulating tumor cells" or "CTC" refers to type of tumor cells of non-pluripotent/pluripotent nature in the blood that is well-known in the art.

The term "cancer stem cell" or "CSC" refers to type of primitive non-pluripotent/pluripotent cancer cells in the blood that is well-known in the art.

The term "biomarker" refers to a biomolecule that is a nucleic acid and is used to characterize a particular cell population. The term is intended to cover both DNA and RNA forms of nucleic acid. The term "biomarker of very small embryonic-like stem cell" refers to any biomarker which can be used to characterize a population of VSELs.

The term "subject" refers to any mammal whose blood or tissue sample has been taken for analysis using the in-vitro method of the present disclosure. The exemplification is based on humans used as subjects.

The term "image analysis" refers to any imaging technology, both invasive and non-invasive, utilized to enumerate the number of VSELs population in blood or tissue samples of subjects to detect presence or absence of cancer and stage of cancer. The image analysis may also assist in identifying the presence or absence of a medical condition in a subject.

The term "invasive" refers to any technique that involves entry into the living body as by way of incision or by way of insertion of an instrument.

The term "body fluid" refers to any fluid secretion from a human body. It refers to blood, or sputum, or urine, or any other types of fluid from the human body.

The term "mitochondria" refers to organelle that comprises of DNA/RNA for sequencing, transcriptomic analysis to determine the medical condition in a subject.

Cancer-related marker comprises all the well-known cancer-related markers in the field of cancer study as per the scientific literature. A non-limiting list of cancer-related marker is mentioned herewith, ABL1, EVI1, MYC, APC, IL2, TNFAIP3, ABL2, EWSR1, MYCL1, ARHGEF12, JAK2, TP53, AKT1, FEV, MYCN, ATM, MAP2K4, TSC1, AKT2, FGFR1, NCOA4, BCL11B, MDM4, TSC2, ATF1, FGFR1OP, NFKB2, BLM, MEN1, VHL, BCL11A, FGFR2, NRAS, BMPR1A, MLH1, WRN, BCL2, FUS, NTRK1, BRCA1, MSH2, WT1, BCL3, GOLGA5, NUP214, BRCA2, NF1, BCL6, GOPC, PAX8, CARS, NF2, BCR, HMGA1, PDGFB, CBFA2T3, NOTCH1, BRAF, HMGA2, PIK3CA, CDH1, NPM1, CARD11, HRAS, PIM1, CDH11, NR4A3, CBLB, IRF4, miR145, PLAG1, CDK6, NUP98, CBLC, JUN, PPARG, CDKN2C, PALB2, CCND1, KIT, PTPN11, CEBPA, PML, CCND2, KRAS, RAF1, CHEK2, PTEN, CCND3, LCK, REL, CREB1, RB1, CDX2, LMO2, RET, CREBBP, RUNX1, CTNNB1, MAF, ROS1, CYLD, SDHB, DDB2, MAFB, SMO, DDX5, SDHD, DDIT3, MAML2, SS18, EXT1, SMARCA4, DDX6, MDM2, TCL1A, EXT2, SMARCB1, DEK, MET, TET2, FBXW7, SOCS1, EGFR, MITF, TFG, FH, STK11, ELK4, MLL, TLX1, FLT3, SUFU, ERBB2, MPL, TPR, FOXP1, SUZ12, ETV4, MYB, USP6, GPC3, SYK, ETV6, IDH1, TCF3, and combinations thereof. Similarly, a list of non-limiting genes comprises all the medical-condition related markers in the field of the disease study as per the scientific literature.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods, and materials are now described. All publications mentioned herein are incorporated herein by reference.

The present disclosure is not to be limited in scope by the specific implementations described herein, which are intended for the purposes of exemplification only. Functionally-equivalent products, compositions, and methods are clearly within the scope of the disclosure, as described herein. Cancer is only one aspect of the medical condition as per the present disclosure since as an example it is widely studied, but the invention pertains to all medical conditions.

Cancer is associated with mutated genes, and analysis of tumour-linked genetic alterations is increasingly used for diagnostic, prognostic, and treatment purposes. In the past decade, 'personalized' or 'stratified' management based on the molecular features of tumours of patients has entered routine clinical practice. The genetic profile of solid tumours is currently obtained from surgical or biopsy specimens; however, the procedure cannot always be performed routinely owing to its invasive nature. First, a comprehensive characterization of multiple tumor specimens obtained from the same patient has illustrated that intratumor heterogeneity exists between different regions in the same tumor (spatial heterogeneity), as well as between the primary tumor and local or distant recurrences in the same patient (temporal heterogeneity) (Gerlinger et al. 2012). Moreover, recent studies have characterized the dynamic changes of tumor features over time with the emergence of treatment-resistant subclones that were present at a minor frequency in the primary tumor (Bedard et al. 2013). Thus, inter- and intra-tumor heterogeneity poses a pivotal challenge to guide clinical decision-making in oncology as biopsies may be inaccurate in capturing the complete genomic landscape of a patient's tumour (Bedard et al. 2013). Second, the complete 'picture' of the tumor is often limited by the tumor accessibility because of the increased rate of clinical complications associated with the invasive procedures necessary to obtain tissue at the time of initial diagnosis as well as throughout the course of disease treatment (Mlika et al. 2016). The poor performance status of many advanced cancer patients may also limit the role of uncomfortable interventional biopsy procedures (Mlika et al. 2016). Moreover, a significant barrier to biomarker testing is the availability of an adequate amount of tissue (e.g., tumor cellularity and size of the specimen) due to increasing diagnostic demands and declining amounts of tissue delivered per patient. Up to 80% of cancer patients with advanced disease will only have tissue from small biopsies or cytology, limiting the ability to perform additional tests, and as many as 31% of patients do not have accessible tissue (Wong et al. 2014). Even when tissue can be collected, preservation methods such as formalin fixation can display high levels ofC>T/G>A transitions in the 1-25% allele frequency range, potentially leading to false-positive results for molecular assays (Wong et al. 2014). Finally, tissue biopsies also increase the cost of patient care, and the turnaround time for getting results can sometimes be longer than those expected by the physician for patient treatment. In light of these limitations on the use of tissue biopsies, new ways to observe tumor genetics and tumor dynamics is the need of the hour.

More recently, DNA methylation-based detection of CpG residues in circulating free DNA has been identified as universal biomarkers of common cancers as well as other diseases such as neurodegeneration and psychiatric disorders. However, some disadvantages of DNA methylation-based detection techniques are (1) time consuming and lengthy procedure, (2) relatively expensive technique, (3) detection highly dependent on assay conditions and presence of CpG residues at specific DNA restriction sites, (4) requires large amounts of DNA which is virtually absent at earlier stages of disease and (5) early-screening sensitivity is very low especially at stage I of detection which is a critical stage for prevention of cancer progression.

Very small embryonic like stem cells (VSELs), are primitive stem cells found in numerous tissues and possess pluripotent properties i.e. ability to differentiate into multiple cell types/tissues. VSELs, are quiescent in nature, but, under oncogenic stress, are activated and have the ability to differentiate into cancer stem cells or tumor initiating cells. These cells subsequently lead to cancer initiation, progression and metastasis. Among embryonic stem cell markers, indicative of pluripotency, Oct4 and its isoforms (Oct4A, Oct4b, Oct4b1) (Wang and Dai, 2010) are implicated in cancer progression, disease stage and disease survival. Oct4A is the master regulator of pluripotency, that undergoes methylation in early stage embryogenesis to switch off gene expression. Thus, adult somatic cells do not express Oct4A, however, there have been reports of Oct4A expression by umbilical cord blood mesenchymal stem cells and bone marrow derived stromal cells. More importantly, Oct4A is expressed at low levels in cancer cell lines and cancer tissues (Li et al., 2015), thus, implying a pluripotent status of some cancer cells, possibly attributed to cancer stem cells origin. In fact, various cancer stem cells have also been shown to express Oct4A, thus, implying that tumor-initiating cells express this gene. During early stages of cancer, tumor-initiating cells shed into the blood circulation and are indicative of disease initiation prior to metastasis and invasion. These cells as well as cell free DNA that circulate in the blood stream might lead to Oct4A expression, a pluripotency marker, that enable early detection of various types of cancer with reasonable accuracy (i.e., high sensitivity and specificity) along with grading of cancer. Also, various cancerous tissues and tumor cells (before they circulate or shed into blood circulation), resident cancer stem cells and some normal tissues such as dental pulp stem cells from adult teeth, benign prostate glands etc. express Oct4A. Moreover, fibroblasts on exposure to microenvironmental changes such as hypoxia (2% oxygen and FGF2), are known to induce Oct4A. This might imply that in response to tissue damage, injury or diseased conditions, Oct4A is highly expressed in tissue of interest with corresponding expression in blood samples also. Since both cancer cells and VSELs possess Oct4A as a common marker, and the overexpression of this marker is associated with metastasis and invasiveness, therefore, the present disclosure discloses an in-vitro method to detect a medical condition in a subject. The method of the present disclosure is based on the detection of Oct4A biomarker in any cell type in the peripheral, circulating blood, including but not limited to normal/ tumor cell free DNA, normal/tumor cell free RNA, cancer stem cells, circulating tumor cells etc. of non-pluripotent origin, particularly very small embryonic-like stem cells. As per the present disclosure, the method not only detects medical condition like cancer, but also detects its stage, patient survival status, effect of oncotherapy etc. without involving any invasive technique.

Thus, the present disclosure discloses Oct4A from VSELs as a marker for early detection (or absence of cancer) as well as grading of cancer and as per stages (I, II, III, IV) of cancer. The present disclosure discloses a mathematical scale, termed as HrC scale, that is proportional numerically to the different stages of cancer as per range of values indicated herein.

The method as per the present disclosure comprises isolating VSELs from blood, tissue and utilizing the isolated VSELs/enriched VSELs as a diagnostic tool for detecting cancer or detecting any medical condition. Based on Oct4A levels in VSELs isolated from blood/tissue, the method is able to correlate the expression of Oct4A with not only the presence or absence of cancer but also the stage of cancer in a large variety of cancers including solid tumors, haematological malignancies and sarcomas that led to development of a mathematical scale termed as HrC. The HrC scale links VSEL Oct4A expression with cancer based on scoring of 0-2: indicative of absence of cancer/inflammation, 2-6 (refers to 1.1-3 fold change in the expression level of Oct4A): inflammatory status indicative of medical conditions such as diabetes, tuberculosis, Alzheimer's disease, dementia, cardiovascular disease, arthritis, etc., 6-10 (refers to 3-5 fold change in the expression level of Oct4A): category includes subjects which are at imminent threat of developing cancer, 10-20 (refers to 5-10 fold change in the expression level of Oct4A): stage I cancer, 20-30 (refers to 10-15 fold change in the expression level of Oct4A): stage II cancer, 30-40 (refers to 15-20 fold change in the expression level of Oct4A): stage III cancer and >40 (refers to more than 20 fold change in the expression level of Oct4A): stage IV cancer. Therefore, the method as per the present disclosure comprises isolating VSELs from blood/tissue and correlating its Oct4A expression with staging of cancer leading to the development of a powerful diagnostic and prognostic tool. Also, Oct4A mea-surement from VSELs has been shown to effectively diagnose the effect of oncotherapy, disease-free survival and recurrence rate with 100% specificity and sensitivity.

The present disclosure provides the significant advantages over tumor cell-mediated cancer detection systems as follows: (1) current "liquid biopsy" diagnostic tools are limited by their sensitivity and specificity, possibly because they are derived from circulating tumor cells, cell free DNA, adult stem cells etc. and a diverse set of biomarkers or DNA methylation profiles are investigated rather than pluripotent stem cells and their markers, (2) rather than known therapeutic utilization of VSELs for regenerative medicine, diagnostic use of VSELs can be made based on blood using a validated HrC scaling system, (3) VSELs can be isolated from 1 ml of blood and hence it has superior advantage as opposed to circulating tumor cells, cell free DNA etc. that require larger volumes for detection, (4) Oct4A measurement is exclusive to enriched VSELs from 1 ml of blood, (5) VSELs based Oct4A measurement is from normal cells indicative of cancer (due to its pluripotency and oncogenic properties) as compared to circulating tumor cells (that may not be prevalent in all tumor types) and cell free DNA (that may not be tumor derived and heterogeneous in nature) and (6) VSELs Oct4A measurement is clinically useful not only to detect presence of a significant variety of cancers (solid tumors, hematologic malignancies and sarcomas), but also imminent cancer before tumor formation, stages of cancer, benign vs. malignant phenotype, inflammatory state, effect of oncotherapy, relapse rate etc. Specifically, the presence of a particular stage of cancer (I, II, III or IV) can assist doctors in decision making for stage-specific therapeutic treatment modalities and non-invasive detection of cancer and its progression. Similarly, imminent cancer detection can lead to preventative strategies while HrC scale testing after oncotherapy can help determine disease survival rate, effect of treatment and probability of recurrence. Thus, Oct4A, an oncogene, is described as the first pluripotent marker that can detect cancer and its stages with 100% sensitivity and specificity as per a trial of 500 non-cancer and 500 cancer patients. Mechanistically, this is primarily due to its constitutive activation in VSELs, defining its pluripotency, and hence the clinical manifestations of a) VSELs initiating cancer endogenously, b) VSELs transformation to cancer stem cells by yet unknown mechanisms, c) cancer stem cells as major drivers of malignancy, as well as invasiveness, migration and motility, d) detection of enriched VSELs in blood and e) Oct4A overexpression as an exclusive marker of primitive and malignant cell phenotype.

Overall, in order to overcome the problems associated with known techniques, the present disclosure discloses a simple and non-invasive technique for identifying a medical condition and inflammatory status in a human subject, particularly presence or absence of cancer and its stages. As per the method, a blood or a urine sample is preferably sufficient enough to obtain details equivalent to those obtained after performing an invasive traditional biopsy technique. Further, the method of the present disclosure would be able to clearly pin-point the medical condition, which has not even shown any symptoms in a human subject, thus, allowing sufficient time for a medical practitioner to treat the human subject. The method of the present disclosure involves enriching very small embryonic-like stem cells (VSELs) from a sample (blood or urine), and further isolating nucleic acid from the enriched very small embryonic-like stem cells. Such nucleic acid can represent the whole genome and/or transcriptome and/or exome of the human subject. The nucleic acid thus obtained is subjected to the sequence analysis by using Next Generation Sequencing or similar techniques to obtain a sequence profile. The profile is compared with a reference sequence to check for the presence of any mutation in at least one marker, wherein the presence of the mutation identifies the presence of a medical condition in the subject. The VSELs as per the present disclosure is positive for certain biomarkers of VSELs as described herein. The markers can be well-known markers specific for any tissue for which the medical condition has to be identified. Biopsies can give vast variance in expressions and mutations depending on which spot the biopsy is done in a tissue. However, the method as disclosed herein, applies at the point of mutation formation, tissue-specific gene expression, and hence removes heterogeneity. Since VSELs may initiate cancer via transformation to cancer stem cells in tissues, tissue-specific VSELs are clearly indicative of representing tumor genotype and phenotype. As per the present method, the genome and transcriptome data received from the sample of a human subject comprising of 50,000-100,000 expression profiles is fed to an algorithm, which in turn gives us RNA information at a tissue level of organs in the body from a blood or a urine or tissue sample. The mutation and expression data will be cross-referenced with the scientific literature and human transcriptome/gene expression databases to identify a set of genes associated with a medical condition. The algorithm can connect transcriptome and whole-genome data to generate readings for tissue-level transcriptome data. Furthermore, based on the data, the organ parameters such as its functional activity, indicators of inflammation, oxidative stress, biological pathways, molecular mechanisms, etc. would also be identified. Based on the identification of primary and secondary organs associated with the transcriptome and mutation data using the algorithm, delineating the susceptibility to a variety of human diseases would also be possible. Further, the method described in the present disclosure also enables testing for rare diseases such as and not limiting to spinal muscular dystrophy, Ehlers-Danlos syndrome, *Proteus* syndrome, sickle cell anemia, Hutchinson-Gilford progeria, etc. that are the end result of genetic mutations. The method as described in the present disclosure, is capable of enriching VSELs in peripheral blood/urine samples, that can be characterized by the presence of Oct4A, Fragilis, and Stella biomarkers. Once the identity of the VSELs is established, the expression levels of the biomarkers such as Oct4A, Fragilis, and Stella is compared to the expression in a control sample, wherein an increase in the expression level of the VSELs biomarkers as compared to the control indicates presence or absence of medical condition and the presence of an inflammatory condition in the human subject. Further, performing the sequencing of the nucleic acid obtained from VSELs is capable of providing deep insights into molecular mechanisms and biological pathways that corroborate the detection. Also, presence or absence of mutation in specific markers identifies the underlying medical condition in the subject. As an alternate implementation of the present disclosure, the protein levels in the enriched VSELs can also be measured to analyse the protein levels of Oct4A in the VSELs obtained from the sample of a human subject. The increase in folds of Oct4A protein can be correlated to the presence or absence of cancer. The protein levels can also be correlated to the staging of cancer. Further, the protein levels can also be correlated to the presence or absence of a medical condition in the subject. As per one of the implementation of the present disclosure, the blood from a subject is to be obtained by a pin-prick (1 ml, or 2 ml, or 5 ml, or 10 ml or 20 ml blood). Following the blood collection, the protein level of Oct4A is to be estimated by using automated ELISA kit, automated immunofluorescence assay kits within minutes to hours in a high-throughput manner. The level of Oct4A in a sample is to be correlated with the level of Oct4A in a control sample (healthy subject), wherein an increase in the protein level of Oct4A is indicative of presence of a medical condition, or prediction of imminent cancer, or presence of cancer. The comparison of the protein levels of Oct4A can further indicate the stage/grade of cancer.

In order to summarise, the method of the present disclosure is able to provide the genetic blueprint of the human subject by analysing the nucleic acid obtained from VSELs isolated from a blood/tissue sample of the human subject. The increase in the expression of Oct4A, or Stella, or Fragilis in the blood/tissue sample of the human subject as compared to a control sample indicates an underlying medical condition and also indicates the inflammatory status in the human subject. The underlying medical condition is accurately pin-pointed by analysing the nucleic acid obtained from VSELs for the presence or absence of mutation in the specific markers. Thus, effectively, providing data equivalent to that of a biopsy, merely from a blood/tissue sample.

As per the present disclosure, any known marker can be analysed from the sequence profile obtained as per the method of the present disclosure. The present disclosure only provides a non-limiting list of such markers. Similarly, as per the method disclosed in the present disclosure, the increased expression of the biomarker of VSELs such as Oct4A, Stella, and Fragilis is an indicative of an underlying medical condition or that of an inflammation present in the human subject. Therefore, it can be contemplated that the absence of any such increase is indicative of a healthy individual. The present disclosure only provides a non-limiting list of diseases that can be detected, however, depending on the type of markers used, any disease can be detected. Further, it is understood that once the entire sequence and transcriptomic profile is obtained from a simple blood sample, the information of the genetic profile can be used to provide complete information on the genetic, or transcriptomic level of a human subject.

An algorithm is defined as wherein the mutation, and expression data of very small embryonic-like stem cells will be cross-referenced with the scientific literature and human transcriptome/gene expression databases to identify a set of genes associated with a medical condition. The algorithm can connect transcriptome and whole-genome data to generate readings for tissue-level transcriptome data. Furthermore, based on the data, the organ parameters such as its functional activity, indicators of inflammation, oxidative stress, biological pathways, molecular mechanisms etc. would also be identified. Based on the identification of primary and secondary organs associated with the transcriptome and mutation data using the algorithm, delineating the susceptibility to a variety of medical conditions would also be possible. Further, the described invention will also enable testing for rare diseases such as and not limiting to spinal muscular dystrophy, Ehlers-Danlos syndrome, *Proteus* syndrome, sickle cell anemia, Hutchinson-Gilford progeria, etc. that are the end result of specific genetic mutations.

The method as per the present disclosure involves a process wherein very small embryonic-like stem cells are to be subjected to proteome, metabolomics, methylation, analysis, and the data acquired will be connected through pathway analysis using various pathway databases to gene expression levels. The genetic analysis of VSELs along with pathway analysis leads to identification of disease treatment modalities (oncotherapy or disease specific interventions) for aiding clinicians and doctors. Further, the cDNAs obtained from VSELs are to be used to further detect the presence of a diseased condition and/or also to provide treatment modalities for treating the diseased condition. Furthermore, transcriptomic analysis of VSELs can be used to detect diseased condition and provide treatment modalities. As an alternative, exome analysis can also be performed on VSELs to detect diseased condition and provide treatment modalities for treating the diseased condition.

In an implementation of the present disclosure, there is provided an in-vitro method for detecting a medical condition in a subject, said method comprising: (a) obtaining a sample; (b) enriching very small embryonic like stem cells from the sample, to obtain a mixture comprising said very small embryonic like stem cells; (c) obtaining nucleic acid from the mixture of step (b); (d) performing an assay with the nucleic acid for analysing expression level of Oct4A in the very small embryonic like stem cells from the sample; and (e) comparing the expression level of Oct4A in the very small embryonic like stem cells from the sample with an expression level of Oct4A in a control sample, wherein an increase in the range of 1.1-3 folds in the expression level of Oct4A in the very small embryonic like stem cells from the sample as compared to the expression level of Oct4A in the control sample detects the presence of a medical condition in the subject. In another implementation of the present disclosure, an increase in the range of 1-2.9, or 1-2.5, or 1-2 folds in the expression level of Oct4A in the very small embryonic like stem cells from the sample as compared to the expression level of Oct4A in the control sample detects the presence of a medical condition in the subject.

In an implementation of the present disclosure, there is provided an in-vitro method for predicting onset of cancer in a subject, said method comprising: (a) obtaining a sample; (b) enriching very small embryonic like stem cells from the sample, to obtain a mixture comprising said very small embryonic like stem cells; (c) obtaining nucleic acid from the mixture of step (b); (d) performing an assay with the nucleic acid for analysing expression level of Oct4A in the very small embryonic like stem cells; and (e) comparing the expression level of Oct4A in the very small embryonic like stem cells from the sample with an expression level of Oct4A in a control sample, wherein an increase in the range of 3-5 folds in the expression level of Oct4A in the very small embryonic like stem cells from the sample as compared to the expression level of Oct4a in the control sample predicts the onset of cancer in the subject. In another implementation of the present disclosure, an increase in the range of 3.2-4.8, or 3.5-4.5, or 3.6-4.2, or 3.8-4 folds in the expression level of Oct4A in the very small embryonic like stem cells from the sample as compared to the expression level of Oct4a in the control sample predicts the onset of cancer in the subject.

In an implementation of the present disclosure, there is provided an in-vitro method for detecting the presence of cancer in a subject, said method comprising: (a) obtaining a sample; (b) enriching very small embryonic like stem cells from the sample, to obtain a mixture comprising said very small embryonic like stem cells; (c) obtaining nucleic acid from the mixture of step (b); (d) performing an assay with the nucleic acid for analysing expression level of Oct4A in the very small embryonic like stem cells; and (e) comparing the expression level of Oct4A in the very small embryonic like stem cells from the sample with an expression level of Oct4A in a control sample, wherein an increase of at least 5 folds in the expression level of Oct4A in the very small embryonic like stem cells from the sample as compared to the expression level of Oct4A in the control sample detects the presence of cancer in the subject. In another implementation of the present disclosure, the increase in the expression level of Oct4A in the very small embryonic like stem cells from the sample is in the range of 5-10, or 10-15, or 15-20, or 20-25 folds as compared to the expression level of Oct4A in the control.

In an implementation of the present disclosure, there is provided an in-vitro method as described herein, wherein the method further comprises analysing the nucleic acid by performing sequence-based assays. In an example of the present disclosure, analysing the nucleic acid by performing sequence-based assays detects the type of cancer.

In an implementation of the present disclosure, there is provided an in-vitro method for monitoring response to anti-cancer therapy, said method comprising: (a) obtaining a sample at one time point during an anti-cancer therapy; (b) enriching very small embryonic like stem cells from the sample to obtain a mixture comprising said very small embryonic like stem cells; (c) obtaining nucleic acid from the mixture of step (b); (d) performing an assay with the nucleic acid for analysing expression level of Oct4A in the very small embryonic like stem cells from the sample; and (e) comparing the expression level of Oct4A in the very small embryonic like stem cells from the sample with an expression level of Oct4A in very small embryonic like stem cells in a reference that monitors the response to anti-cancer therapy. The decrease in the expression level of Oct4A in very small embryonic like stem cells in the sample as compared to the expression level in the reference indicates a positive response to the anti-cancer therapy, wherein the reference is at least one selected from a group consisting of: (i) a sample obtained prior to administration of anti-cancer therapy; (ii) a sample obtained at a previous time point as compared to the time point mentioned in step (a) of the method as described herein; (iii) a sample obtained at a subsequent time point as compared to the time point mentioned in step (a) of the method as described herein; and (d) a sample obtained from a cancer-free subject.

In an implementation of the present disclosure, there is provided an in-vitro method for detecting a positive response to anti-cancer therapy, said method comprising: (a) obtaining a sample-I before administration of an anti-cancer therapy; (b) obtaining a sample-II after administration of the anti-cancer therapy; (c) enriching very small embryonic like stem cells from the sample-I to obtain a mixture-I comprising said very small embryonic like stem cells; (d) enriching very small embryonic like stem cells from the sample-II to obtain a mixture-II comprising said very small embryonic like stem cells; (e) obtaining nucleic acid-I from the mixture-I; (f) obtaining nucleic acid-II from the mixture-II; (g) independently performing an assay with the nucleic acid-I and the nucleic acid-II for analysing expression level of Oct4A; and (h) comparing the expression levels of Oct4A from the nucleic acid-II with the expression level of Oct4A from the nucleic acid-I, wherein a decrease in the expression level of Oct4A from the nucleic acid-II as compared to the expression level of Oct4A from the nucleic acid-I detects a positive response to the cancer treatment.

In an implementation of the present disclosure, there is provided an in-vitro method for detecting cancer, said method comprising: (a) obtaining a sample; (b) enriching very small embryonic like stem cells from the sample, to obtain a mixture comprising said very small embryonic like stem cells; (c) obtaining nucleic acid from the mixture of step (b); (d) performing an assay with the nucleic acid for analysing expression level of Oct4A in very small embryonic like stem cells; (e) comparing the expression level of Oct4A in very small embryonic like stem cells in the sample with an expression level of Oct4A in very small embryonic like stem cells in a control sample, wherein an increase in the expression level of Oct4A in very small embryonic like stem cells in the sample as compared to the expression level of Oct4A in very small embryonic like stem cells in the control sample indicates presence of cancer; and (f) performing sequence-based assays on the nucleic acid and analysing for mutation in at least one cancer-related marker, wherein presence of mutation in the at least one cancer-related marker indicates presence of a specific type of cancer based on the cancer-related marker analysed. In another implementation of the present disclosure, comparing the expression level of the biomarker of very small embryonic-like stem cell in the sample with an expression level of the at least one biomarker in a control sample and co-relating the sequence profile with a reference sequence profile to identify the presence or absence of a mutation in at least one marker are done by an algorithm.

In an implementation of the present disclosure, there is provided an in-vitro method for detecting cancer as described herein, wherein the method further comprises analysing the expression level of the cancer-related marker in the nucleic acid obtained in step (c), and wherein the expression level of the marker is analysed by using quantitative PCR techniques.

In an implementation of the present disclosure, there is provided an in-vitro method as described herein, wherein the nucleic acid is obtained from the mixture by any one method selected from the group consisting of: (a) guanidinium thiocyanate-phenol-chloroform nucleic acid extraction; (b) cesium chloride gradient centrifugation method; (c) cetylt-rimethylammonium bromide nucleic acid extraction; (d) alkaline extraction; (e) resin-based extraction; and (f) solid phase nucleic acid extraction.

In an implementation of the present disclosure, there is provided an in-vitro method as described herein, wherein performing an assay with the nucleic acid for analysing expression level of Oct4A in very small embryonic like stem cells is done by a technique selected from a group consisting of quantitative PCR, flow cytometry, and Next Generation Sequencing (NGS).

In an implementation of the present disclosure, there is provided an in-vitro method as described herein, wherein the control is the expression level of Oct4A in very small embryonic like stem cells obtained from a cancer-free subject. In another implementation of the present disclosure, the control is the expression level of housekeeping gene, wherein the housekeeping gene includes, but not limited to, 18S rRNA, ACTB, ATP5B, CyC1, EIF4A2, GAPDH, RPL13A, SDHA, TOP1, UBC, YWHAZ, PGK1, PPIA, RPLP0, ARBP, B2M, TFRC, GUSB, HMBS, HPRT1, TBP. In an example of the present disclosure, the housekeeping gene is 18 S rRNA.

In an implementation of the present disclosure, there is provided an in-vitro method as described herein, wherein an enriching of the very small embryonic like stem cells from a blood sample comprises: (a) contacting the blood sample with a neutral buffer in a ratio range of 1:1 to 1:20, to obtain a first mixture; (b) contacting at least one salt solution to the first mixture in a ratio range of 1:2 to 1:10, to obtain a second mixture; and (c) processing the second mixture to obtain enriched very small embryonic like stem cells. The processing of the second mixture comprises, at least one method selected from a group consisting of: (a) extraction process; (b) washing process; (c) centrifugation process, and combinations thereof. In another implementation of the present disclosure, contacting the blood sample with a neutral buffer in a ratio range of 1:2 to 1:18, or 1:3 to 1:15, or 1:5 to 1:12, to obtain a first mixture, and wherein contacting the at least one salt solution to the first mixture in a ratio range of 1:3 to 1:9, or 1:4 to 1:8, or 1:4 to 1:7, to obtain a second mixture.

In an implementation of the present disclosure, there is provided an in-vitro method as described herein, wherein the cancer-related marker is selected from a group consisting of well-known markers established to be related to cancer. Further, the method of the present disclosure is independent of invasive techniques. In another implementation of the present disclosure, the cancer-related marker is selected from the group consisting of mir145, OLR1, CD68, MSR1, CXCL16, NCAN, TKTL1, ANO4, CHIT1, GPNMB, CCL18, TGFbeta1, FSP1, S100A6, SLC13A3, BGN, NCF2, 6Ckine, MMP-9, MMP-3, MMP-7, Integrin-$\beta$4, Pleiotrophin, urokinase R, HLA-C, SLC9A3R1, NAT9, RAPTOR and SLC12A8, SPINK5, FcepsilonRI-beta, PHF11, IGFBP1, FACL4, IL1R, TGFbeta, CHRNA3/5, IREB2, HHIP, FAM13A, AGER, Troponin T&I, HSP60, BNP, GDF-15, MMP2, MMP3, MMP9, IL6, TNFalpha, CRP, SOX9, ACAN, COL2A1, DKK1, FRZB, RUNX2, COL10A1, IGH, IGHM, IGHG1, Sirtuins, ACE2, IFI27, IFIT1, IFITM1, DPP4, KRAS, BRCA1 and 2, TP53, HLA-DQA1, HLA-DQB1, HLA-DRB1 (Type I), PPARG, KCNJ11, CDKAL1, CDKN2A-CDKN2B, IDE-KIF11-HHEX, IGF2BP2 and SLC30A8 (Type II), and combinations thereof.

In an implementation of the present disclosure, there is provided in-vitro method for detecting a medical condition in a subject, wherein the medical condition identified is selected from the group consisting of multiple sclerosis, kidney disorders, skin disease, liver disease, lung disease, cardiovascular diseases, osteoarthritis, viral disease, cancer, and diabetes. In an example of the present disclosure, the medical condition is cancer.

In an implementation of the present disclosure, there is provided a method for treating cancer, said method comprising: (a) obtaining a sample from a subject; (b) enriching very small embryonic like stem cells from the sample, to obtain a mixture comprising said very small embryonic like stem cells; (c) obtaining nucleic acid from the mixture of step (b); (d) performing an assay with the nucleic acid for analysing expression level of Oct4A in very small embryonic like stem cells; (e) comparing the expression level of Oct4A in very small embryonic like stem cells in the sample with an expression level of Oct4A in a control sample, wherein an increase in the expression level of Oct4A in very small embryonic like stem cells in the sample as compared to the expression level of Oct4A in the control sample detects cancer; and (f) administering anti-cancer therapy to the subject for treating cancer.

In an implementation of the present disclosure, there is provided an in-vitro method for grading cancer in a subject, said method comprising: (a) obtaining a sample; (b) enriching very small embryonic like stem cells from the sample, to obtain a mixture comprising said very small embryonic like stem cells; (c) obtaining nucleic acid from the mixture of step (b); (d) performing an assay with the nucleic acid for analysing expression level of Oct4A in the very small embryonic like stem cells; and (e) comparing the expression level of Oct4A in the very small embryonic like stem cells from the sample with an expression level of Oct4A in a control sample, wherein an increase in the range of 5-10 folds in the expression level of Oct4A in the very small embryonic like stem cells from the sample as compared to the expression level of Oct4A in the control sample is indicative of stage I cancer in the subject.

In an implementation of the present disclosure, there is provided an in-vitro method for grading cancer in a subject, said method comprising: (a) obtaining a sample; (b) enriching very small embryonic like stem cells from the sample, to obtain a mixture comprising said very small embryonic like stem cells; (c) obtaining nucleic acid from the mixture of step (b); (d) performing an assay with the nucleic acid for analysing expression level of Oct4A in the very small embryonic like stem cells; and (e) comparing the expression level of Oct4A in the very small embryonic like stem cells from the sample with an expression level of Oct4A in a control sample, wherein an increase in the range of 10-15 folds in the expression level of Oct4A in the very small embryonic like stem cells from the sample as compared to the expression level of Oct4A in the control sample is indicative of stage II cancer in the subject.

In an implementation of the present disclosure, there is provided an in-vitro method for grading cancer in a subject, said method comprising: (a) obtaining a sample; (b) enriching very small embryonic like stem cells from the sample, to obtain a mixture comprising said very small embryonic like stem cells; (c) obtaining nucleic acid from the mixture of step (b); (d) performing an assay with the nucleic acid for analysing expression level of Oct4A in the very small embryonic like stem cells; and (e) comparing the expression level of Oct4A in the very small embryonic like stem cells from the sample with an expression level of Oct4A in a control sample, wherein an increase in the range of 15-20 folds in the expression level of Oct4A in the very small embryonic like stem cells from the sample as compared to the expression level of Oct4A in the control sample is indicative of stage III cancer in the subject.

In an implementation of the present disclosure, there is provided an in-vitro method as described herein, wherein the nucleic acid is either DNA or RNA. In another implementation of the present disclosure, the nucleic acid is selected from the group consisting of normal RNA, normal DNA, tumor RNA, or tumor DNA from the sample.

In an implementation of the present disclosure, there is provided an in-vitro method as described herein, wherein enriching of the very small embryonic-like stem cells from the sample is by any method selected from the group consisting of flow cytometry, magnetic bead-based separation, filtration, microfluidic-based cell sorting, aptamer-based cell isolation, and buoyancy activated cell sorting.

In an implementation of the present disclosure, there is provided an in-vitro method as described herein, wherein the nucleic acid represent a genome, or a transcriptome, or an exome, cDNA.

In an implementation of the present disclosure, there is provided an in-vitro method as described herein, wherein the sample is selected from the group consisting of blood, tissue, urine, and sputum. In another implementation of the present disclosure, the sample is at least one cell type in the blood, and wherein the at least one cell type is selected from the group consisting of cancer stem cell, and circulating tumor cells.

In an implementation of the present disclosure, there is provided a reagent kit comprising reagents for enriching very small embryonic-like stem cell from a blood sample.

In an implementation of the present disclosure, there is provided a detection kit comprising: (a) primer set for analysing expression level of at least one biomarker selected from the group consisting of Oct4A, Stella, and Fragilis in a mixture comprising very small embryonic-like stem cell; (b) reagents for performing quantitative PCR assay; (c) reagents for performing whole genome or exome or transcriptome sequencing; and (d) at least one tissue-specific array for analysing a sequence profile.

In an implementation of the present disclosure, there is provided an in-vitro method for grading cancer in a subject, said method comprising: (a) obtaining a sample; (b) enriching very small embryonic like stem cells from the sample, to obtain a mixture comprising said very small embryonic like stem cells; (c) obtaining nucleic acid from the mixture of step (b); (d) performing an assay with the nucleic acid for analysing expression level of Oct4A in the very small embryonic like stem cells; and (e) comparing the expression level of Oct4A in the very small embryonic like stem cells from the sample with an expression level of Oct4A in a control sample, wherein an increase in the range of 20 to higher folds in the expression level of Oct4A in the very small embryonic like stem cells from the sample as compared to the expression level of Oct4A in the control sample is indicative of stage IV cancer in the subject.

In an implementation of the present disclosure, there is provided a method for detecting presence of cancer in a subject, said method comprising: (a) obtaining a sample from a subject; (b) enumerating the number of very small embryonic like stem cells in the blood sample; and (c) comparing the number of very small embryonic like stem cells in the blood sample with the number of very small embryonic like stem cells in a control blood sample, wherein an increase in the number of very small embryonic like stem cells in the blood sample as compared to the number of very small embryonic like stem cells in a control blood sample detects the presence of cancer in the subject.

In an implementation of the present disclosure, there is provided a method for predicting the onset of cancer in a subject, said method comprising: (a) obtaining a sample from a subject; (b) enumerating the number of very small embryonic like stem cells in the blood sample; and (c) comparing the number of very small embryonic like stem cells in the blood sample with the number of very small embryonic like stem cells in a control blood sample, wherein an increase in the number of very small embryonic like stem cells in the blood sample as compared to the number of very small embryonic like stem cells in a control blood sample predicts the onset of cancer in the subject.

In an implementation of the present disclosure, there is provided a method for detecting the presence of a medical condition in a subject, said method comprising: (a) obtaining a sample from a subject; (b) enumerating the number of very small embryonic like stem cells in the blood sample; and (c) comparing the number of very small embryonic like stem cells in the blood sample with the number of very small embryonic like stem cells in a control blood sample, wherein an increase in the number of very small embryonic like stem cells in the blood sample as compared to the number of very small embryonic like stem cells in a control blood sample detects the presence of a medical condition in the subject.

In an implementation of the present disclosure, there is provided a method for detecting presence of cancer in a subject, said method comprising: (a) enumerating in-vivo the number of very small embryonic like stem cells in the blood/tissue of a subject; and (b) comparing the number of very small embryonic like stem cells in the subject with the number of very small embryonic like stem cells in a control, wherein an increase in the number of very small embryonic like stem cells in the subject as compared to the number of very small embryonic like stem cells in a control detects the presence of cancer in the subject.

In an implementation of the present disclosure, there is provided a method for predicting the onset of cancer in a subject, said method comprising: (a) enumerating in-vivo the number of very small embryonic like stem cells in the blood/tissue of a subject; and (b) comparing the number of very small embryonic like stem cells in the subject with the number of very small embryonic like stem cells in a control, wherein an increase in the number of very small embryonic like stem cells in the subject as compared to the number of very small embryonic like stem cells in a control predicts the onset of cancer in the subject.

In an implementation of the present disclosure, there is provided a method for detecting presence of a medical condition in a subject, said method comprising: (a) enumerating in-vivo the number of very small embryonic like stem cells in the blood/tissue of a subject; and (b) comparing the number of very small embryonic like stem cells in the subject with the number of very small embryonic like stem cells in a control, wherein an increase in the number of very small embryonic like stem cells in the subject as compared to the number of very small embryonic like stem cells in a control detects the presence of medical condition in the subject.

In an implementation of the present disclosure, there is provided a method for identifying a medical condition in a human subject as described herein, wherein the very small embryonic-like stem cell have a size lesser than 7 microns in diameter. In another implementation of the present disclosure, the very small embryonic-like stem cell has a size in the range of 1-7 microns in diameter. In an alternate implementation of the present disclosure, the very small embryonic-like stem cell has a size in the range of 2-6 microns in diameter.

In an implementation of the present disclosure, there is provided a method as described herein, wherein the control sample is the expression level of a housekeeping gene from the subject. In another implementation, the housekeeping gene is 18s rRNA.

In an implementation of the present disclosure, there is provided a method for identifying a medical condition in a human subject as described herein, wherein the biomarker of very small embryonic-like stem cell is selected from the group of pseudogenes of Oct4, and wherein the pseudogenes of Oct4 is selected from the group consisting of Oct4pg1, Oct4pg2, Oct4pg3, Oct4pg4, Oct4pg5, Oct4pg6, and Oct4pg7.

In an implementation of the present disclosure, the VSELs isolated from the blood of a healthy individual is to be used for therapeutic applications. The VSELs are to be enriched in-vitro by promoting cell expansion and is to be edited using CRISPR-Cas9 technology for therapeutic applications. Alternatively, the VSELs are to be differentiated into tissue-specific cell types under suitable conditions and used for appropriate therapeutic application. As per another implementation, the VSELS are to be de-differentiated into induced pluripotent stem cells (iPSCs). The iPSCs can be further differentiated into tissue-specific cells which can be injected into the site of injury for therapeutic application. In an alternate implementation, there is provided a kit comprising reagents for enriching VSELs from a blood sample.

In an implementation of the present disclosure, there is provided a method as described herein, wherein Oct4A expression is to be analysed along with other genes modulated in the subject.

In an implementation of the present disclosure, there is provided a method as described herein, wherein an increase in the expression level of Oct4A from very small embryonic-like stem cell from the sample as compared to the expression level of Oct4A in the control sample differentiates malignant from benign conditions.

In an implementation of the present disclosure, there is provided a method as described herein, wherein an increase in the expression level of Oct4A from very small embryonic-like stem cell from the sample as compared to the expression level of Oct4A in the control sample indicates mitochondrial alterations.

In an implementation of the present disclosure, there is provided an in-vitro as described herein, wherein the method is based on HrC scaling test, and wherein, the HrC scale refers to a numerical scaling factor that indicates a value of twice the Oct4A fold change observed to detect above absence, presence of cancer or its stages.

In an implementation of the present disclosure, there is provided a method as described herein, wherein the blood sample from a subject is obtained and from the said sample, cell of interests are isolated automatically using centrifugation in a BioSafety Level II cabinet with further automated DNA/RNA isolation, and an automated RT-PCR based gene expression of Oct4A, thus, enabling automatic HrC score determination.

In an implementation of the present disclosure, there is provided a method as described herein, wherein the method analyses any gene listed in the NCBI gene list database (ncbi.nlm.nih.gov/gene/) in VSELs, extracted from the blood/tissue, that when modulated as compared to control subjects, which is measured by expression analysis and mutation analysis of transcriptome and/or mutational analysis of exome and genome, indicates a medical condition with tissue-specific localization.

Although the subject matter has been described with reference to specific implementations, this description is not meant to be construed in a limiting sense. Various modifications of the disclosed implementations, as well as alternate implementations of the subject matter, will become apparent to persons skilled in the art upon reference to the description of the subject matter. It is therefore contemplated that such modifications can be made without departing from the spirit or scope of the present subject matter as defined.

EXAMPLES

The disclosure will now be illustrated with a working example, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein. It is to be understood that this disclosure is not limited to particular methods, and experimental conditions described, as such methods and conditions may vary.

Materials and Methods

Clinical Study Design

The study as per the present disclosure was conducted after taking ethics approval from Ethics Committee of Maharashtra Technical Education Society at Sanjeevan Hospital, Pune, India and was registered with Clinical Trial Registry India (CTRI/2019/01/017166).

Initially 180 samples were collected along with patient history and all the related information. Oct-4A mRNA expression was studied in the VSELs enriched from the peripheral blood and helped arrive at a scale (HrC scale) wherein cancer stage was correlated to fold change in OCT-4A expression. Once the scale was obtained, its validation was done in a total of 1000 subjects which were recruited from seven different sites across India for the study out of which 500 were non-cancer and 500 were cancer patients (Table 1). The samples were blinded by National Facility for biopharmaceuticals. The patients with histologically or cytologically proven malignancy either solid tumors or haematological malignancy were included in the cancer group. Informed consent form was obtained from every subject. Circulating tumor cells (CTCs) were studied randomly in few cases on interest.

Blood Sample Processing

Blood samples (approximately 10 ml) were collected from the subjects and processed to enrich VSELs as described below. Briefly, the samples were layered over Ficoll-Hypaque and subjected to density gradient centrifugation at 1200 rpm for 15 min. Post centrifugation, cells in the RBC fraction were subjected to RBCs lysis and then centrifuged at 3000 rpm (1000 g) to pellet down VSELs.

RNA Isolation and cDNA Synthesis

Total RNA was extracted from the VSEL pellet using RNAplus (MP Biomedicals, Irvine, USA) according to manufacturer's instructions. After RNA extraction, first-strand cDNA was synthesized using the Revert Aid First strand cDNA synthesis kit (Thermo scientific, UK) according to the manufacturer's instructions. Briefly, 1 μg of total RNA was incubated with 5× Reaction Buffer and reverse transcriptase mix. The reaction was carried out in Applied Biosystems GeneAmp® thermal cycler 9700 (Applied Biosystems, USA) as per manufacturer's instructions.

qRT-PCR Studies

The expression level of Oct4A gene transcript was estimated by real-time PCR system-ABI 7500 (Applied Biosystems, USA) using Thermo Scientific Maxima SYBR Green/ROX qPCR Master Mix kit (Thermo scientific, UK) and gene specific primer sequences, namely, Oct4A: Forward AGCCCTCATTTCACCAGGCC (SEQ ID NO: 1), and Reverse TGGGACTCCTCCGGGTTTTG (SEQ ID NO: 2). The 18s rRNA gene was used as housekeeping gene. The amplification conditions were: initial denaturation at 94° C. for 3 min followed by 45 cycles comprising of denaturation at 94° C. for 30 s, primer annealing at 62° C. for 30 s, and extension at 72° C. for 30 s followed by melt curve analysis step from 55° C. to 95° C. The fluorescence emitted was collected during the extension step of each cycle. The homogeneity of the PCR amplicons was verified by studying the melt curve. $C_t$ values generated in each experiment using the 7500 Manager software (Applied Bio-systems, UK) were used to calculate the mRNA expression levels.

Circulating Tumor Cells (CTCs)

CTCs were studied as described earlier (Diehl et al 2018). CTCs are found in patients with solid tumors and function as a seed for metastasis (Palmirotta et al 2018). They are considered as clinical biomarker and therapeutic target and are considered as a component of liquid biopsy. The peripheral blood was drawn into EDTA tubes. Within one hour, the tubes were subjected to centrifugation at 820 g for 10 min. Approx. 1-ml aliquots of the plasma was transferred to 1.5-ml tubes and centrifuged at 16,000 g for 10 min to pellet any remaining cellular debris. The supernatant was transferred to fresh tubes and stored at −80° C. Total genomic DNA was purified from 2 ml of the plasma aliquots using the QIAamp MinElute kit (Qiagen) according to the manufacturer's instructions. The amount of total DNA isolated from plasma was quantified with a modified version of a human LINE-1 quantitative real-time PCR assay, as described previously (Diehl et al 2008). The amount of total DNA isolated from plasma samples was quantified. Three primer sets were used to amplify differently sized regions within the most abundant consensus region of the human LINE-1 family (79 bp for: 5'-agggacatggatgaaattgg-3' (SEQ ID NO: 3). 79 bp rev: 5'-tgagaatatgcggtgtttgg-3' (SEQ ID NO: 4); 97 bp for: 5'-tggcacatatacaccatggaa-3' (SEQ ID NO: 5), 97 bp rev: 5'-tgagaatgatggtttccaatttc-3' (SEQ ID NO: 6); 127 bp for: 5'-acttggaaccaacccaaatg-3' (SEQ ID NO: 7), 127 bp rev: 5'-tcatccatgtccctacaaagg-3' (SEQ ID NO: 8)). PCR was performed in a 25 μl reaction volume consisting of template DNA equal to 2 μl of plasma, 0.5 U of Taq DNA Polymerase, lx PCR buffer, 6% (v/v) DMSO, 1 mM of each dNTP, 5 μl of SYBR Green and 0.2 μM of each primer. Amplification was carried out in Cycler using the following cycling conditions: 94° C. for 1 min; 2 cycles of 94° C. for 10 s, 67° C. for 15 s, 70° C. for 15 s; 2 cycles of 94° C. for 10 s, 64° C. for 15 s, 70° C. for 15 s, 2 cycles of 94° C. for 10 s, 61° C. for 15 s, 70° C. for 15 s; 35 cycles of 94° C. for 10 s, 59° C. for 15 s, 70° C. for 15 s.

Procedure to be Followed as Per the Present Disclosure

The blood sample obtained from a human subject was processed for enriching very small embryonic-like stem cells. As per one aspect of the present disclosure, blood samples (test samples) were obtained as a part of the study. The blood sample was contacted with a neutral buffer in a ratio range of 1:1 (blood sample:neutral buffer) to 1:20, to obtain a first mixture. At least one salt solution was contacted with the first mixture in a ratio range of 1:2 (salt solution:first mixture) to 1:10, to obtain a second mixture. The second mixture was processed to obtain a processed second mixture comprising very small embryonic-like stem cells. Nucleic acid was obtained from the very small embryonic-like stem cells by a method well known in the art.

Results

Initially a HrC scale was developed based on Oct-4A expression in 120 samples. The Oct4A expression in peripheral blood was correlated with the medical history (PET scan and biopsy reports). It was observed that Oct4A was manifold upregulated in peripheral blood of cancer patients compared to non-cancer subjects. Within cancer patients, the expression of OCT4A was highest for stage 4 cancer and lowest for stage 1. On the basis of fold increase, an HrC scale was developed using which non-cancer and cancer subjects can be segregated. The HrC scale/value as per the present disclosure was designed in a manner that the HrC value is double the fold change in the expression of Oct4A analyzed from the blood samples of the test subject as compared to a housekeeping gene or Oct4A analyzed from the blood sample of a healthy subject. For clarity purposes, if the fold change in the expression of Oct4A is X, then the HrC value would be 2 X. Also, the stage of the cancer was deciphered. The non-cancer patients and those with increased inflammation that could lead to cancer initiation (on correlating with patient history) in future also revealed specific range of values. The subjects were identified and distributed on the basis of their HrC score as non-cancer, inflammation, high risk, stage I cancer, stage II cancer, stage III cancer and stage IV cancer (FIG. 1).

Between January to May 2019, total of 1051 patients were screened and recruited for the study. 51 subjects out of 1051 were excluded because of screen failures. There were 534 males and 466 females. The median patient age was 63.0 years for the complete dataset. The mean weight was 69.3 kg and mean height was 161.38. Table 1 summarizes patient demographics for the complete dataset.

TABLE 1

| Demographics of all the subjects included in the study | |
|---|---|
| Patient population | Number of participants |
| Gender | |
| Male | 534 |
| Female | 466 |
| Age (years) | |
| Mean | 61.3 |
| Weight (kg) | |
| Mean | 69.3 |

TABLE 1-continued

| Demographics of all the subjects included in the study | |
|---|---|
| Patient population | Number of participants |
| Height (cm) | |
| Mean | 161.38 |

Out of 500 cancer patients, 431 patients were on treatment ($R_x$) 48 were not subjected to any treatment after diagnosis of cancer ($R_x$ Naïve) and 21 patients had undergone surgical intervention for cancer treatment ($R_0$). Patients with 25 different types of cancers were included in the study as shown in FIG. 2.

Figure 3:
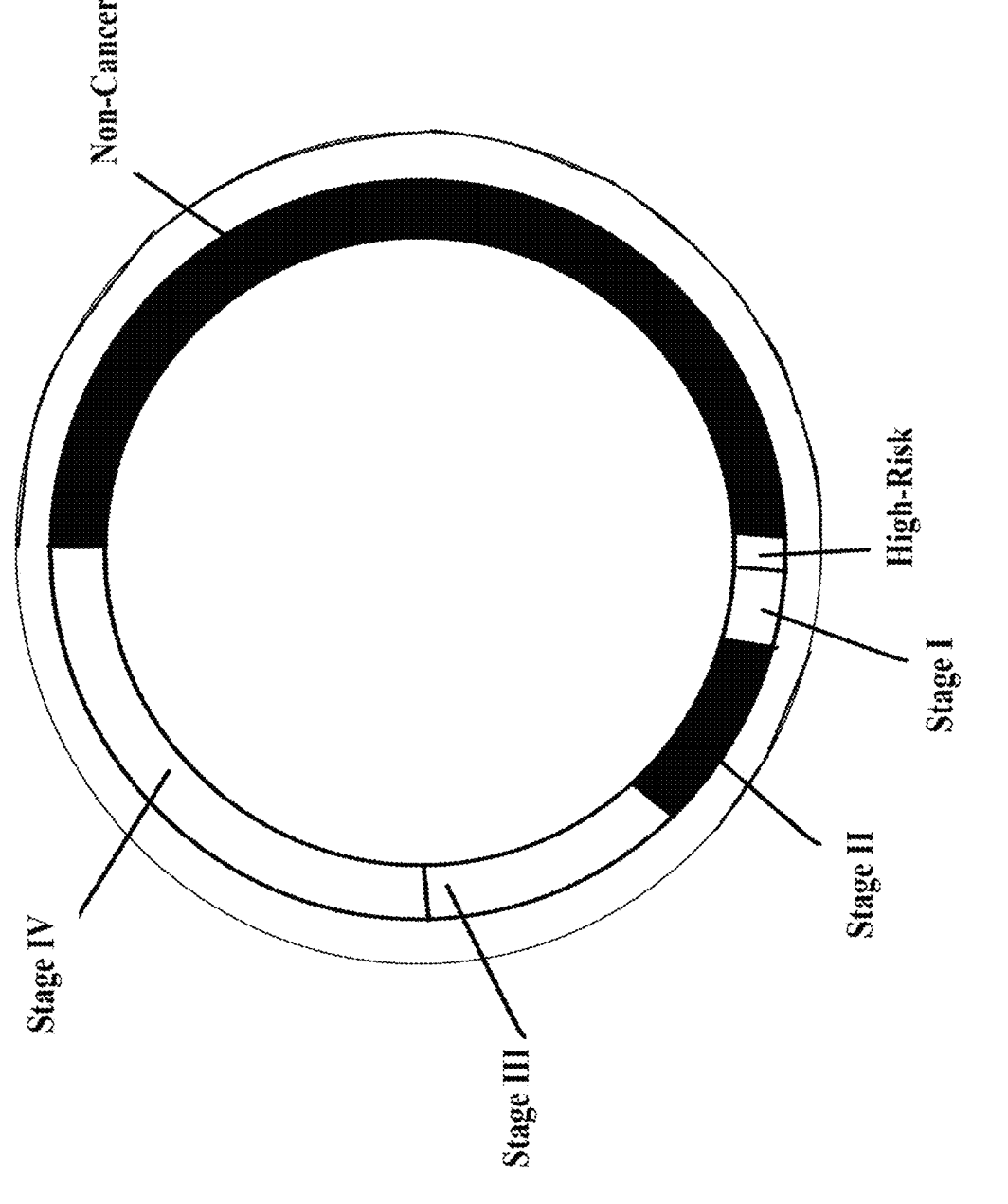
FIG. 3 depicts a pie chart showing distribution of subjects identified as non-cancer, inflammation & high risk, Stage I cancer, stage II cancer, stage III cancer and stage IV cancer on the basis of their HrC score, in accordance with an implementation of the present disclosure.

Out of 1000 samples analyzed for HrC, 498 samples were non-cancerous, 7 were assessed to be in high risk stage, 11 were in stage I cancer, 94 were in stage II cancer, 133 were in stage III cancer, and 257 were in stage IV cancer (FIG. 3).

HrC levels were able to detect presence of several types of solid and liquid cancers. FIGS. 4-8 provides details of the results in all the 1000 study subjects. As evident there was no ambiguity in the HrC values. Table 2 provides details of 10 cases where we could obtain novel results using HrC as a tool to monitor cancer state of patients.

TABLE 2

Details of 10 cases where the results were obtained using HrC as a tool to monitor cancer state of patients.

| Patient details | HrC levels (as per the present disclosure) | Remarks |
|---|---|---|
| 68 years old female with colorectal cancer. patient was subjected to HrC and CTCs analysis | HrC analysis revealed a score of 26.82 indicating stage II cancer whereas ctDNA were not detected in the blood | Several researchers have reported non-reliability of ctDNA for accurate diagnosis of cancer (Shen et al 2018) |
| 55-years-old, female was recruited in cancer group with stage III cervical adenocarcinoma | On the day of surgery, HrC value was 32.11. Four weeks post removal of the tumor surgically, HrC value fell to 9.14 which suggested that the patient was still fell in high risk category and required adjuvant chemotherapy. She underwent four cycles of adjuvant chemotherapy (Day 28 to Day 160) and PET scan was performed at the end showed absence of lesion. The patient was declared cancer- free, and the HrC value showed a reading of 1.9 (Day 167) in alignment with PET scan. | The HrC test successfully aided oncologists to monitor the disease progression and risk of relapse. |
| 74 years old male patient was enrolled with Stage 4 liver cancer | HrC test was performed one day prior to neo- adjuvant chemotherapy and was 49.43 (indicating stage 4 cancer patient). After three cycles of neo-adjuvant chemotherapy, HrC value dropped to 42.01. | HrC test could serve as a reliable marker for oncologists to interpret disease progression and effectiveness of the treatment |
| 68-years-old, 76-Kg male was recruited in non-cancer group. | HrC values were 9.78 which suggested that he was a high risk (pre-cancer individual). Based on HrC values, he was investigated in details and enlargement of prostate was detected with PSA levels 182 ng/ml and blood sugar levels as 210 mg/dL and 170 mg/dL fasting and post prandial respectively. All the other blood test including complete blood count, blood urea nitrogen test, | The subject was experiencing generalized body weakness, acidity, abdominal pain and a weight loss. Patient management was carried out efficiently based on HrC test results |

TABLE 2-continued

Details of 10 cases where the results were obtained using
HrC as a tool to monitor cancer state of patients.

| Patient details | HrC levels (as per the present disclosure) | Remarks |
|---|---|---|
| | serum uric acid, liver function test and lipid test were normal. PET scan showed no signs of lesion across the body. After obtaining patient consent, radical prostatectomy was performed. On the day of surgery (9 weeks post first HrC analysis), HrC value increased to 10.89 from 9.78. Four weeks post prostatectomy, HrC value was reduced to 2.1 which indicated slight organ inflammation. | |
| 47-year-old stage 3 breast cancer patient with a 7.4 cm left breast mass. | HrC value was 36.18 which classified her as Stage III. Surprisingly, CTCs were not detected in blood. | Core biopsy of the mass showed metastatic breast cancer, estrogen receptor (ER) 95% positive, progesterone receptor 85% positive and HER2 negative. ASCO tumor marker guidelines (2007) suggest that measurement of CTCs should not be used for diagnosis or treatment modifications. |
| 65-year-old female with a tumor above ovary | HrC value was 41.28 (Day 0) and cancer antigen 125 (CA-125) was 198.8 along with pain in abdomen (Day 3). Patient underwent surgery (Day 7) for the removal of both ovaries, uterus, and fallopian tube. Immuno-histochemistry analysis (Day 10) of the removed tissue suggested primary site of cancer be the stomach since the tissue was positive for CK-20 & CDX2/SATB2. | The doctors were unable to detect primary site of cancer and it was impacting the course of treatment (Day 30). HrC test was able to accurately detect the primary site of cancer as the appendix by analyzing the expression profile of Day 44. |
| 49-year-old male non-cancer subject | The subject was recruited in Non-cancer group, upon analysis it was found that HrC score was 7.20 indicating "high risk cancer" category. In-depth analysis further revealed that the subject was at the risk of developing oral cancer. The patient was an active user of pan masala and gutkha and regular smoker | HrC test was able to screen subjects for the development of cancer. |
| 78-year-old cancer patient with carcinoma of lung and parenchymal non-cerebral metastasis | The subject was recruited in cancer group and HrC analysis showed value of 46.34 (indicating stage IV cancer) (Day 0). Post two cycles of chemotherapy (Day 36) diagnostic test was conducted again to assess the efficacy of the treatment. The HrC test at Day 36 showed value of 42.38, clearly indicating improvement in the cancer. | HrC test was used to assess the efficacy of the chemotherapy treatment. |
| 52-year-old male non-cancer subject | The subject was recruited in Non-cancer group, upon analysis it was found that HrC score was 7.86 indicating "high risk cancer" category. In-depth analysis further revealed that the subject was at the risk of developing thyroid cancer. Upon further | HrC test was able to detect high risk category and organ which was at the risk of developing cancer. |

TABLE 2-continued

Details of 10 cases where the results were obtained using
HrC as a tool to monitor cancer state of patients.

| Patient details | HrC levels (as per the present disclosure) | Remarks |
|---|---|---|
| | consultation with Oncologist, the subject underwent biopsy which revealed benign hemorrhagic nodule with degenerative changes and had extremely high levels (224 pg/ml) of calcitonin. The subject underwent total thyroidectomy | |
| 68-year-old male patient with liver cancer | HrC value was 40.15 indicative of 4th stage liver cancer. A detailed mutational analysis revealed lymph node metastasis as per TNM classification. Further mutation analysis revealed primary and secondary organs as liver and lung with osseous metastasis. Cholangiocarcinoma was identified as specific type of cancer and further sub-localization was identified using pathway analysis (data not shown). | HrC test was able to accurately detect stage of cancer and primary site of cancer by analyzing the mutation and expression profile. |

Analyzing the Number of VSELs in the Blood of a Subject and its Correlation with a Medical Condition or Cancer in the Subject The VSELs count per unit of blood can be measured to not only distinguish between people with cancer, imminent cancer and non-cancer but also distinguish between stages of cancer. Invasive in-vitro imaging of VSELs is done by routine colorimetric staining using nuclear staining approaches such as hematoxylin, Hoechst 33342 dye etc. once the cells are isolated from a unit of blood. Non-invasive optical microscopy, on the other hand, is a recently developed in-vivo technique that takes advantage of confocal microscopy principles for imaging large cross-sectional areas of blood vessels with sub-micron resolution (thus, identifying, cells of interest in size range of 2-6 µm indicative of VSELs) without staining. One such example is through methods pertaining to electric or ultrasound waves can be utilized. The principle behind the technique is different light scattering coefficients of cellular and subcellular structures when incident on a particular blood vessel detected at a measured depth below the tissue surface. In another implementation, fluorescent-based techniques and image capturing of stained cells in blood flow can also be used though this process may modify the cells and/or result in toxicity.

FIG. 10 depicts the comparison of the number of VSELs present in the blood of a cancer patient versus a healthy individual. The analysis was performed by isolating VSELs from peripheral blood of a fourth stage 65-year old female patient with Chronic Myeloid Leukemia (blood cancer), preparing smears, fixing in 4% paraformaldehyde, staining with Hematoxylin/Eosin and imaging using a microscope. Referring to FIG. 9, the left panel represents the blood sample from a healthy subject, and the right panel represents the blood sample from a healthy subject. As per the analysis of the image, the approximate number of VSELs in the top, middle, and bottom image of the left panel are 25, 22, and 22. On the other hand, the approximate number of VSELs in the top, middle, and bottom image of the right panel are 53, 55, and 52. Therefore, FIG. 9 clearly demonstrates that the increase in number of VSELs can be correlated with the presence of cancer.

As per one implementation of the present disclosure, the quantity of VSELs in the blood can also be analyzed in-vivo. FIG. 11 depicts one of the many modalities which can be used to analyze the number of VSELs in the blood by in-vivo methodology. It is envisaged to develop a Bio-GPS system for cancer detection using fluorescent quantum dot nanoparticles (step 1), that when fused with intermediate adapter proteins (step 2) and VSEL-specific antibodies (step 3) results in quantum dot-adapter protein-VSEL specific antibody fusion molecules (step 4). This solution when injected into blood stream (step 5) results in tagging specifically of VSELs by quantum dots and selective fluorescence emission that can be captured via fluorescent imaging computer tomography (step 6). Thus, in vivo VSEL image analysis can lead to contrast agent injection-mediated identification of VSEL count in normal vs. cancer patients.

The results of the study suggest that it is possible to predict, screen and diagnose cancer from a blood test. The results confirm the potential of HrC test (method as per the present disclosure) for reliable blood-based diagnosis of cancer. The specificity of HrC test was >99% with no false positives or false negatives. HrC test adopts a machine learning based algorithm for multi-analyte data to enable the cancer to be specifically identified. Data on ten interesting cases is provided where HrC analysis helped the clinician (Table 2).

The three criteria for an ideal cancer detection diagnostic tool are: (i) sensitivity, ability to correctly detect the disease accurately (ii) specificity, ability to distinguish healthy, non-cancerous individuals and (iii) localization or classification, ability of test to pinpoint the type of cancer and its tissue of origin. Currently, the most studied blood-based non-invasive tests for cancer detection utilize circulating tumor cells (CTCs), circulating tumor DNA (ctDNA) and exosomes based on identification of mutations and expression of cancer-specific biomarkers (Zhou et al., 2020). Even though CTCs and ctDNA can be considered as an attractive tool for early detection and diagnosis of cancer, several studies have questioned the sensitivity, specificity of these tests for cancer prognosis (Kowalik et al., 2017).

Circulating tumor cells and tumor DNA that slip into blood circulation from dying cancer cells (by necrosis) in patients can be detected, and advanced technologies have been developed to identify even a single molecule of tumor DNA including genetic mutations/DNA methylation patterns in bloodstream (Killock 2018). However, not all early-stage tumors shed DNA and CTCs and hence it is not possible to accurately depict the molecular signature of cancer unless a novel approach is pursued. Moreover, co-morbid inflammatory diseases might shed DNA (Chaudhary and Mittra, 2019) that will conflict with cancer detection for accurate disease diagnosis, thus, compromising both sensitivity and specificity. Cancer stem cells (CSCs) on the other hand are rare and difficult to isolate and may not accurately depict the stages of cancer. Overall, there is a need for a highly, accurate, non-invasive blood-based monitoring system to detect cancer of various stages and sub-types.

Oct4, Nanog and Sox2 are critical stem cell pluripotency markers that are expressed in blood and cancerous tissues (Wang and Herlyn, 2015; Monferrer et al., 2019) and depict the disease prognosis, rate of survival, effect of chemotherapy and other such disease-related parameters. Thus, developing a highly, specific and sensitive prognostic "liquid biopsy" tool will enable clinicians to identify if cancer is present, cancer is imminent as well as the stage of cancer. However, though there are adequate citations, circulating tumor cells and cancer stem cells are present in rare quantities in blood and tissue biopsies and the isolation is cumbersome also. Hence, there is a need to measure Oct4, Nanog and Sox2 levels in normal cells of blood such as hematopoietic stem cells, mesenchymal stem cells etc. In fact, these markers have been tested for in blood samples of all patients in a recent study (Sodja et al 2016), however, correlation with stage of cancer has not been investigated.

The present disclosure discloses a simple method (HrC test) for assessing the molecular profile of cancer (range 0-60) from the blood of a subject. The different range of scores was correlated to different stages of cancer using a third-degree polynomial equation comprising Oct4A, Nanog, and Sox2 gene expression levels and provides information for all types of cancers including whether (i) cancer is present (ii) cancer is imminent (iii) different stage of cancer and (iv) effect of oncotherapy. Further, the method disclosed by the present disclosure also tells whether the subject from which the sample (blood) is analyzed has any other medical condition apart from cancer. The HrC scale links VSEL Oct4A expression with a medical condition based on scoring of 0-2 which is indicative of absence of cancer/inflammation, and 2-6 which relates to presence of inflammatory status indicative of medical conditions such as diabetes, tuberculosis, Alzheimer's disease, dementia, cardiovascular disease, arthritis, etc. The non-cancer patients and those with increased inflammation which could lead to cancer initiation (on correlating with patient history) in future could also be classified based on HrC data. The results of the study suggest that it is possible to predict, screen and diagnose cancer from a blood test. The specificity of HrC test was >99% with no false positives or false negatives. HrC adopts a machine learning based algorithm. Cancer is a fatal, debilitating disease that accounted for >9 million deaths worldwide in 2018 (Bray et al 2018). The disease aetiology is characterized by genetic alterations (Chakravarthi et al 2016) and metabolic changes (Hammoudi et al 2011) that transcend into uncontrollable, abnormal cellular growth, proliferation and metastatic progression (Riggi et al 2018). Late stage cancers often lack an effective treatment option (Chakraborty and Rahman 2012). Currently, the need of the hour is to detect the disease as early as possible, since early stage detection can result in aiding clinicians in identifying suitable interventions to prevent the onset or further progression of the disease, reduce treatment cost, improve patient outcome (disease-free and progression free survival, time in remission, delay relapse) on a case-by-case basis (Schiffman et al 2015). Nearly 70% of all cancers can be prevented if risk is detected at an early stage, thus, emphasizing need for better point-of-care diagnostics (Gandhi et al 2017). Average five-year survival rate at early stage is 75% whereas average five-year survival rate at late stage is merely 16% (Eskiizmir et al 2017).

Current diagnostic methods include PET CT scan, MRI and the gold standard of all methods, the tissue biopsy (Cowling and Loshak 2019). Biopsy is expensive, invasive or painful, causing discomfort and the surgical procedures warrant with undue, resultant side-effects (Do et al 2019). Furthermore, due to inconspicuous anatomical locations, some tumor specimens are difficult to isolate making them inaccessible (Do et al 2019). Also, tissue biopsies might not give accurate information due to tumor heterogeneity in gene expression and mutations. Tissue biopsies may augment risk of metastatic lesions and safety is also a concern, for e.g. related to sampling of angiogenic tumor microenvironments (Do et al 2019). Similarly, imaging methods do not, at times, detect the cancer source, i.e., cancer of unknown primary (CUP) origin (Varadhachary 2007) is relatively frequent leading to inaccurate diagnosis affecting interventional therapies. Colonoscopy, prostate specific antigen, mammography and cervical cytology are limited number of existing screening test for a few number of cancer types (Ilic et al 2018); although their efficacy is questioned (Ilic et al 2018) and several patients do not follow medical guidelines for screening (Ilic et al 2018). Majority of cancer types lack an effective non-invasive early screening option (Curry et al 2003).

The HrC scale was developed and tested on multiple cancer types on the basis of a pilot clinical study conducted with subjects registered with CTRI bearing number CTRI/2018/07/015116. This clinical study was performed to assess the Oct4A fold change expression values of cancer and noncancer subjects. The Oct4A expression of the subjects was correlated with their medical history (PET scan and biopsy reports) and it was observed that Oct4A was manifold upregulated in cancerous blood sample as compared to non-cancer subject. Within cancer patients the expression of Oct4A was highest for stage 4 cancer and lowest for Stage 1. Furthermore, in cancer subjects, stages of cancer were accurately identified on the basis of HrC scale.

The present disclosure discloses a method (HrC test) which involves isolating VSELs from blood and utilizing its associated pluripotency marker Oct4A with path-breaking implications as a diagnostic and prognostic tool with significant advantages over tumor cell-mediated cancer detection systems.

In case of imminent cancer detection, the method can lead to preventative strategies while HrC scale testing after oncotherapy can help determine disease survival rate, effect of treatment and probability of recurrence. Thus, Oct4A from VSELs, an oncogene, is described as the first pluripotent marker that can detect cancer and its stages with 100% sensitivity and specificity as per a trial of 500 non-cancer and 500 cancer patients. Mechanistically, this is primarily due to its constitutive activation in VSELs, defining its pluripotency, and hence the clinical manifestations of a) VSELs initiating cancer endogenously, b) VSELs transformation to cancer stem cells by yet unknown mechanisms, c) cancer stem cells as major drivers of malignancy, as well as invasiveness, migration and motility, d) detection of enriched VSELs in blood and Oct4A overexpression as an exclusive marker of primitive and malignant cell phenotype.

Example of cDNA Analysis of VSELS

In a whole transcriptomic analysis, RNA fragments are converted to cDNA libraries for gene expression and mutational analysis. Thus, a transcriptomic analysis of VSELs from a fourth stage liver cancer patient was conducted and mutations were found in the following genes corresponding to various organ metastasis of cancer (Table 3). As shown herewith, the highest number of gene mutations were obtained for bone lesions, though only 2 of those genes were non-intronic. On the other hand, liver also showed mutations in 2 non-intronic gene out of 3 while lung showed one 5UTR gene mutation as per COSMIC, ICGC databases. Hence, it can be contemplated that the cDNA information of the VSELs enriched from the peripheral blood of a subject can provide information to specifically identify the medical condition. For example, even in cases where the origin of cancer is not identified using the conventional methodologies, the cDNA obtained from VSELs enriched from the peripheral blood can provide information to this effect.

file, with ~68% and ~40% of genes in the top 56 expressing genes corresponding to this bile duct cancer phenotype as well as highest expression levels as compared to other cancer sub-types as per scientific literature, driverdb-v3 and expression atlas databases. Moreover, according to 1 database geneorganizer (based on gene-disease associations disgenet.org), ~30% out of top 60 genes corresponded to lung organ as body part, 32% based on scientific literature with ~20% of top 56 gene corresponding to lung cancer as per lung cancer explorer database. Moreover, 23% of top 56 genes from our dataset were either mutated or differentially expressed in osteosarcoma patients as per scientific literature. Moreover, MUC family of genes may be prognostic markers for osteosarcoma. Thus, in order to overcome the shortcomings associated with the literature, the present disclosure discloses a non-invasive, blood-based diagnostic test to not only detect presence of cancer, but also its stage and primary (liver) as well as secondary and tertiary localizations (lung and bone) based on transcriptomic and mutational analysis.

In the present disclosure, it was found out that the mucinous genes were significantly upregulated in the transcriptome. Also, according to mutational data analysis, both SLC19A1 and SLC46A1 which were significantly mutated are transporters for folic acid and methotrexate (osteosarcoma treatment medication). Similarly, MTR gene was mutated that belongs to methionine metabolism and folic acid pathway, implying defects in folate metabolic pathway

TABLE 3

Mutation profile analysis of 9 genes (obtained from the VSELs enriched from peripheral blood of human subjects as per the present disclosure).

| Gene | VAR CLASS | cDNA Change | AA change | Localization |
|---|---|---|---|---|
| GRIN2C | INFRAME-INS | c.3145__3146insCCCCGGAGC | p.Glu1048__Leu1049insProProGlu | Liver |
| PRICKLE4 | INFRAME-INS | c.863__864insTCT | p.Leu288dup | Liver |
| UNC50 | INTRONIC | c.-4-46T > A | NA | Liver |
| NR1I2 | 5UTR | c.-20dup | NA | Lung |
| PRKDC | FRAMESHIFT-INS-SS-PRX | c.3729dup | p.Arg1244ProfsTer41 | Bone |
| CSMD3 | INTRONIC | c.5605 + 51del | NA | Bone |
| CYFIP2 | INTRONIC | c.208-1815dup | NA | Bone |
| EIF1B | INTRONIC | c.298-33__298-32del | NA | Bone |
| ZCHHC6 | INFRAME-DEL | c.2811__2813del | p.Lys937del | Bone |

As per the present disclosure, transcriptomic analysis of VSELs from a fourth stage liver cancer patient with pulmonary and bone metastases was conducted, wherein the blood sample of said patient was tested for genetic analysis to determine disease type, classification and localization. By utilizing the pluripotency marker Oct4A and a combination of genetic and mathematical technique in the method (HrC test) for diagnosing cancer and its grade, the HrC score obtained was 40.1. Thus, the HrC score of 40.1 corresponds to presence of cancer as well as 4$^{th}$ stage classification.

Further, transcriptomic analysis of the patient's blood sample revealed 102 significant mutations and 57,000 unique mRNA profiles. Out of the 102 mutations, 3 corresponded to liver-specific lesions viz. PRICKLE4, GRIN2C and UNC50, while 5 mutations corresponded to bone lesions (PRKDC, CSMD3, CYFIP2, EIF1B, ZCHHC6), and 1 to lung (NR1I2) using the COSMIC and ICGC mutation databases. The gene expression data for those corresponding to a read-count of >100 was compared to that in existing cancer databases comprising of TCGA dataset for 33 cancer types. Cholangiocarcinoma exhibited the highest expression proin patient. LGR6, a gene implicated in Wnt signaling pathway, was also mutated and so was PRKDC associated with osteoblast turnover according to wikipathways. HOOK3 was mutated, that was associated with bone cells while NR1I2, liver specific gene, linked to xenobiotic metabolism was also mutated. Using linkedomics, the genes were associated with mutations across TCGA cholangiocarcinoma datasets. Interestingly, it was found out from the study conducted in the present disclosure that MUC16 gene expression was associated with >25% mutations in direct linkage with p<0.05 amongst cholangiocarcinoma patients.

To check if expression of genes in the dataset as per the present disclosure, were associated with hepatocellular carcinoma, cholangiocarcinoma and lung cancers, the results of the experiments of the present disclosure were compared with the literature to identify primary, secondary and metastatic cancer sites based on transcriptomic analysis of patient. The results of the present disclosure were cross reference with the results of the scientific literature:

(a) Mucins

The mucins that were expressed at high levels in the test data as per the present disclosure are: MUC16, MUC12, MUC4, MUC6, MUC17 and MUC19. The results of the present disclosure were compared with a scientific literature, wherein MUC16 was detected in $^3$/$_{63}$ samples (48%) while MUC4 was detected in $^{19}$/$_{63}$ patients (30%) in subjects with intrahepatic cholangiocarcinoma-mass forming type. Both genes were associated with poor prognosis in higher expression patients as compared to lower expression patients. Also, no MUC4 or MUC16 was detected in normal tissue samples of patients. Similarly, MUC4 has been reported to have weak staining in normal intrahepatic bile ducts as per another study, but expression in cholangiocarcinoma has been reported. Also, focal expression of MUC6 in cholangiocarcinoma has been reported. In yet another study, MUC4 expression was detected in 10 out of 27 (37%) intrahepatic cholangiocarcinoma patients and was identified as a useful marker for prediction of outcome of cholangiocarcinoma patients. In another research study, MUC4 was found to be overexpressed (1.9 fold) in bile of 27% of 69 biliary tract cancer patients. In a research paper comprising of studies of 249 patients, it was found that high or positive levels of MUC4 was associated with poorer survival of patients with resected cholangiocarcinoma. Further, in yet another study, MUC12 and MUC17 were frequently deleted in up to 64% of cholangiocarcinoma patients ($^{59}$/$_{92}$ samples studied). Lymph node metastasis of cholangiocarcinoma is associated with these MUC12 and MUC17 deletions. Although no MUC12 and MUC17 deletions were observed in the present disclosure, however, an enhanced gene expression of MUC12 and MUC17 was observed, thereby, indicating there may be a correlation of the enhanced gene expression of MUC12 and MUC17 with cholangiocarcinoma.

Furthermore, in a compendium of 73 studies on immunohistochemical analysis of 4126 cholangiocarcinoma patients, MUC4, which was highly expressed in the dataset according to the present disclosure, was identified as associated with an overall survival in resected patients. MUC4 gene amplification may lead to enhanced expression of RNA or protein levels in lung cancer patients. TTN and MUC16 are proteins present in largest quantities in HepG2, a human hepatocellular cell line according to a study. MUC16 is overexpressed in air-pollution exposed lung cancer patients in a city in CHINA as compared to non-cancer subjects living in cleaner air conditions. Thus, in addition to ovarian cancer, MUC16 may be a candidate marker for lung cancer. Moreover, mucins expression may be associated with progression of adenocarcinoma of lung according to a couple of research studies. In one study, in only $^1$/$_{26}$ patients examined, MUC4 and MUC6 expression by immunohistochemistry studies were present in cholangiocarcinoma patient. Although MUC4 is amongst the top 10 genes expressed, however, MUC6 was expressed at lower levels in the dataset of the present disclosure. Intrahepatic cholangiocarcinoma has poor prognosis based on expression of MUC4, MUC12, MUC17 while good prognosis based on MUC6.

Nevertheless, overall from the above observations, it can be concluded that mucin expression i.e., MUC16, MUC4, MUC12, MUC6, MUC17 and MUC19 in the dataset of the present disclosure indicate cholangiocarcinoma over hepatocellular carcinoma since presence of mucins favours cholangiocarcinoma over hepatocellular carcinoma.

(b) Whole Exome Sequencing of Liver Cholangiocarcinoma and Lung Cancer Patients

According to the previous findings in the literature, Copy Number Variation (CNV) Gain was observed in various genes for hepatocarcinoma and intrahepatic cholangiocarcinoma based on whole exome sequencing of tumor tissue samples. CNV gain has been shown to be linearly related to enhanced gene expression. According to the dataset of the present disclosure, 68% out of 56 genes showed CNV gain ≥3 that implies an enhanced gene expression corresponding to cholangiocarcinoma. Moreover, the data represented tissue excisions from right lobe of liver of patient. In contrast, 32% of top 56 genes were significantly altered via percentage frequency gain in gene expression with FDR <0.05 as per one scientific paper on CNV analysis of lung cancer patient totaling up to 100% of 56 genes.

(c) Other Genes of Interest Expressed in the Dataset of the Present Disclosure

KCNQ1OT1 gene is upregulated in hepatocellular carcinoma tissues according to a study as confirmed by GSE dataset which was highly expressed in the present disclosure also. Moreover, KCNQ1OT1 gene was also overexpressed in non-small cell lung cancer patients.

PDE4DIP, another gene, is associated with higher survival at higher expression in lung cancer patients based on 3 lung adenocarcinoma datasets. Also, it is mutated at 3-4% in cholangiocarcinoma and combined hepatocellular-cholangiocarcinoma patients based on a mutation dataset.

According to the present disclosure, the mitochondrial MT-ND5, MT-ND4 and MT-CO1 genes were expressed. As per the findings of one of the studies of the literature, it has been observed that non-synonymous mutations in the aforementioned genes were observed in 9 out of 102 cholangiocarcinoma patients. Further, all three mitochondrial genes are associated with oxidative phosphorylation, defects in which lead to oncogenic activation of cancer.

SYNE1 is a tumor suppressor gene that is overexpressed in hepatocellular carcinoma tissues. In sporadic lung cancer patients, it is frequently methylated leading to gene inactivation, however, as per the present disclosure, higher expression of SYNE1 gene was observed. Further, in lung and pancreatic (potential site) cancers, KRAS mutation is most frequently associated with p53, PKHD1 and SYNE1 genes. GRIN2B is also a tumor suppressor gene that was upregulated as per the study conducted in the present disclosure, however, it was silenced in lung cancer patients. UBR4 is overexpressed in mouse liver tumors and mouse liver cancer cell line (Hepa 1-6). As per the dataset of the present disclosure, it was observed that UBR4 was also overexpressed. It is pertinent note that the downregulation of UBR4 gene is associated with reduced viability and migration of cancer cells. Further, it was observed that SNHG14 was increased in hepatocellular tissues and lung cancer tissue samples as per the present disclosure.

FRAS1 is a liver metastasis gene that is overexpressed and a biomarker in a study of gastric cancer patients. Also, FRAS1 is associated with cell migration and invasion in A549 lung cancer cell line. According to the present disclosure, FRAS1 was also upregulated.

KSR2 gene expression is associated with Ras mediated signalling i.e., MEK/ERK and Myc and MAPK. KSR2 is also associated with AMPK. According to the study conducted in the present disclosure, it was found out that there was an increase in the expression of KSR2 gene.

CACNA1E is significantly upregulated in liver cancer patients, and is a driver cancer gene for lung cancer patients. It was observed that according to the experiment conducted in the present disclosure, CACNA1E gene was overexpressed.

Further, it was observed that NFASC gene that was expressed in the dataset of the present disclosure, has been shown to be upregulated in hepatocellular carcinoma patient tissues as compared to normal tissues and is associated with cholangiocarcinoma. Moreover, NFASC gene is also associated with cancer cell migration in lung cancer patients.

PLXNA4 is upregulated in lung cancer patient tissue samples and in the dataset of the present disclosure.

NF1 is a key tumor suppressor gene in hepatocellular carcinoma patients. NF1 blocks RAS/RAK/MAPK pathways. NF1 loss promotes KRAS-driven lung cancer progression according to literature. In lung cancer patients, NF1 loss leads to glutamine metabolism addiction. COL7A1 has been shown to be upregulated in cholangiocarcinoma patients. SORL1 is upregulated in liver cancer patients and is a liver metastasis gene while GPR98 is a bone, liver, lung metastasis gene. CSMD2 gene expression is increased in intrahepatic cholangiocarcinoma. ACACA is significantly higher in liver cancer as compared to normal tissue samples and in lung tissue samples. BRF1 is increased in hepatocellular carcinoma patients and is associated with shorter survival times. ANK3 is significantly increased in small cell lung cancer patients but decreased in non-small cell lung cancer patients.

MUC16, MUC6, MUC17, MUC4, MUC12, TTN are all associated with osteosarcoma patients. Moreover, MUC family of genes is associated with potential prognostic markers for osteosarcoma. Overall, following genes which were highly expressed in the dataset of the present disclosure were found to be mutated in >50% of osteosarcoma patients: MACF1, OBSCN, NEB, SYNE1, SYNE2, FRAS1, DNAH9.

Therefore, it can be inferred from the above observations that there is a relationship between high gene expression in VSELs and mutational profile in tissues in cancer patients. It was also observed that the following genes showed positive standardized mean difference for tumor vs. normal samples based on a compendium of studies: MUC16, KCNQ1OT1, MUC4, UBR4, CACNA1E, NF1, COL7A1, SORL1, CSMD2, BRF1, LAMA1, MUC6, MUC17 for lung adenocarcinoma and NEB, NF1, COL7A1, SORL1, CSMD2, ACACA, RYR1, UNC80, LAMA1, HIF1AN, MCC for lung squamous cell carcinoma using lung cancer explorer database.

Table 4 provides the expression profile of genes as per various databases and scientific literature for liver, lung and bone in concordance with top 56 genes of transcriptomic data. FIG. 12-14 shows the expression profiles of top 56 genes of transcriptomic data.

TABLE 4

| S.NO. | Localization | Percent Expression |
|---|---|---|
| 1 | Liver | 50 |
| 2 | Lung | 27 |
| 3 | Bone | 23 |

FIG. 12 depicts the expression profiles of top 56 genes (obtained as per blood-based genetic test) across 33 cancer types based on TCGA data using DriverDBv3 database. The highest combination of sum of squares of expression levels is obtained for cholangiocarcinoma, corresponding to primary localization of cancer confirmed by PET-SCAN imaging. The expression profiles correspond to ratio of median gene expression of tumor tissue to media gene expression in normal samples. The data for each expressed gene normalized ratio was combined for each cancer type and graphically presented.

FIG. 13 depicts the expression profiles of top 56 genes (obtained as per blood-based genetic test) across 33 cancer types based on 3 cancer genomic databases. Data was plotted using jvenn. 24 of genes were significantly expressed from top 56 genetic data as per DriverDBv3 database, 21 for Expression Atlas database and 23 for Expression Atlas 1 patient data implying ~41% correspondence. Also, a panel of 9 genes were common between all three databases to be significantly expressed viz. FRAS1, OBSCN, NEB, COL7A1, PHLDB1, HIF1AN, SSPO, NFI and TRAPPC9. Interestingly, 7 genes were significantly mutated in 7 cholangiocarcinoma patients as per one study viz. MUC16, MUC12, MUC4, MUC19, RYR3, OBSCN, TTN.

FIG. 14 shows the expression profiles of top mucin genes and mutations (obtained as per blood-based genetic test) across biopsies of osteosarcoma patients.

Overall, 42% of top 56 genes were expressed as per TCGA cholangiocarcinoma database, 42% corresponds to Expression Atlas while 68% was associated with CNV gains from scientific literature for one patient (right lobe of liver localization (segment IVa)) leading to mean of 50% for cholangiocarcinoma. Similarly, 27% correspond to lung cancer while 23% corresponds to osteosarcoma adding up to 100%, as also shown in Table 4.

Based on scientific literature for whole exome, transcriptome and CNV amplification, it can be observed that there is a 68% probability of top 56 gene expression for cholangiocarcinoma and 32% for lung cancer.

Further, in the present disclosure, the sub-locations of bone tissue were identified based on the below analysis:

Two types of analysis with genemania software was done. The top 3 or top 56 genes expressing from the blood genetic test were mapped to the various mutations and expression analysis of sacrum, acetabulum, C6 vertebrae and scapula as per DISGENET and scientific literature.

Based on the above analysis, it was found out that there was a good genetic interaction between the genetic dataset and the bone sub-locations as shown in Table 5. Table 5 shows the genetic interactions of genes as per various databases and scientific literature for bone tissues in concordance with top 56 genes of transcriptomic data.

TABLE 5

| S.No. | Localization | Genes of Interest |
|---|---|---|
| 1 | Sacrum | FGFR1-4, MDR1, HIF1A, MRP1, SPTBN5, MORN1, VANGL1, RET |
| 2 | Acetabulum | HSPG2, LZTR1, COL2A1, TRPV4 |
| 3 | C6 Vertebrae | MYH3, MYO18B, GDF3, GDF6, MEOX1 |
| 4 | Scapula | SGCG, TBX2, TRPV4, COL2A1, ACTN3 |

It can be contemplated that based on similar genetic interactions for identifying the location sites of bone tissues, a person skilled in the art can identify the potential sites of cancer as pancreas and kidney also.

Therefore, it can be concluded that the present disclosure provides an in-vitro and non-invasive method to identify primary, secondary and metastatic cancer sites based on transcriptomic analysis of patient.

Advantages of the Present Disclosure

The method as disclosed in the present disclosure, is a simple blood or urine-based test and does not involve any invasive techniques. The method provides data equivalent to the information obtained through traditional biopsies, but without the invasive part. Also, a biopsy can only be performed if there is a cue about the tissue that could be damaged or is responsible for an underlying condition. In many cases, the human body might not give the early signals relating to an underlying medical condition because of which by the time the condition arises, the patient could be left with very less time at hand. In essence, the disclosure herein was able to establish the effective diagnostic scope of this non-invasive process to not only prognose and detect cancer earlier than current known technologies but also have the widest scope to detect significant variety of cancers (solid tumors, hematologic malignancies and sarcomas) with a single marker. The ability of this method was also identified to provide mutational and expressions transcriptome data, analytical depth and pathways informational data to a level that is currently possible only through invasive biopsies and that too of multiple organs. In case of the presence of early signs of inflammation or a medical condition, the sequencing of the transcriptome, genome, or exome, obtained from the VSELs can clearly pin-point the medical condition of the subject. Additionally, the sequencing data can also be used to accurately pin-point the type of cancer that is present in the subject.

Further, the present disclosure also includes the scope of a transcriptome gene bank. The transcriptome gene bank is a repository to store genetic material outside the organism in an in-vitro setting for subsequent analysis at a later stage to assess health conditions. As a result, storage of RNA samples (–80° C. or even under liquid nitrogen), that are indicative of mutational and expression profiles of healthy as well as diseased individuals, can provide, at any time point, a dynamic analysis of the genetic alterations. Thus, RNA storage of individuals is of critical importance to detect diseased conditions temporally. VSELs can be readily obtained from the blood samples in a painless, fast, low-cost and non-invasive way and are also indicative of the dynamic tissue-specific gene expression profiles indicative of whole organ biopsy. Thus, the RNA bank storing genetic material of VSELs from a subject's blood sample can potentially provide rich data about the health condition of the individual from a whole body/organ perspective at any stage of the patient's lifetime. This data can be cross-referenced with other commercially available pathology tests to aid the clinicians and doctors in disease diagnosis and possibly suggesting treatment modalities.

REFERENCE

Asai, N. et al. (2013) 'Is emphysema a risk factor for pneumothorax in CT-guided lung biopsy?', *SpringerPlus*, pp. 1-6. doi: 10.1186/2193-1801-2-196.

Bedard, P. L. et al. (2013) 'Tumour heterogeneity in the clinic', *Nature*, pp. 355-364. doi: 10.1038/nature12627.

Bowcock, A. M. and Cookson, W. O. C. M. (2004) 'The genetics of psoriasis, psoriatic arthritis and atopic dermatitis', *Human Molecular Genetics*. doi: 10.1093/hmg/ddh094.

Bray, F. et al. (2018) 'Global cancer statistics 2018: GLOBOCAN estimates of incidence and mortality worldwide for 36 cancers in 185 countries', *CA: A Cancer Journal for Clinicians*, 68(6), pp. 394-424. doi: 10.3322/caac.21492.

Chakraborty, S. and Rahman, T. (2012) 'The difficulties in cancer treatment.', *Ecancermedicalscience*, 6, p. ed16. doi: 10.3332/ecancer.2012.ed16.

Chakravarthi, B. V. S. K., Nepal, S. and Varambally, S. (2016) 'Genomic and Epigenomic Alterations in Cancer',

*American Journal of Pathology*, pp. 1724-1735. doi: 10.1016/j.ajpath.2016.02.023.

Chaudhary, S. and Mittra, I. (2019) 'Cell-free chromatin: A newly described mediator of systemic inflammation', *Journal of Biosciences*. doi: 10.1007/s12038-019-9849-7.

Cleary, S. P. et al. (2013) 'Identification of driver genes in hepatocellular carcinoma by exome sequencing', *Hepatology*, 58(5), pp. 1693-1702. doi: 10.1002/hep.26540.

Cowling, T. and Loshak, H. (2016) *An Overview of Liquid Biopsy for Screening and Early Detection of Cancer, CADTH Issues in Emerging Health Technologies*. Available at: http://www.ncbi.nlm.nih.gov/pubmed/32239883.

Dhingra, R. and Vasan, R. S. (2017) 'Biomarkers in cardiovascular disease: Statistical assessment and section on key novel heart failure biomarkers', *Trends in Cardiovascular Medicine*, pp. 123-133. doi: 10.1016/j.tcm.2016.07.005.

Diehl, F. et al. (2008) 'Circulating mutant DNA to assess tumor dynamics', *Nature Medicine*, 14(9), pp. 985-990. doi: 10.1038/nm.1789.

Ene, R. et al. (2015) 'Synovial inflammation in patients with different stages of knee osteoarthritis', *Romanian Journal of Morphology and Embryology*, 56(1), pp. 169-173.

Eskiizmir, G., Ermertcan, A. T. and Yapici, K. (2017) 'Nanomaterials: Promising structures for the management of oral cancer', in *Nanostructures for Oral Medicine*, pp. 511-544. doi: 10.1016/B978-0-323-47720-8.00018-3.

Francis, R. and Lewis, C. (2018) 'Myocardial biopsy: Techniques and indications', Heart, 104(11), pp. 950-958. doi: 10.1136/heartjnl-2017-311382.

Gandhi, A. K. et al. (2017) 'Burden of preventable cancers in India: Time to strike the cancer epidemic', *Journal of the Egyptian National Cancer Institute*, pp. 11-18. doi: 10.1016/j.jnci.2016.08.002.

Gerlinger, M. et al. (2012) 'Intratumor Heterogeneity and Branched Evolution Revealed by Multiregion Sequencing', *New England Journal of Medicine*, 366(10), pp. 883-892. doi: 10.1056/nejmoa1113205.

Hammoudi, N. et al. (2011) 'Metabolic alterations in cancer cells and therapeutic implications', *Chinese Journal of Cancer*, pp. 508-525. doi: 10.5732/cjc.011.10267.

Hannivoort, R. A., Hernandez-Gea, V. and Friedman, S. L. (2012) 'Genomics and proteomics in liver fibrosis and cirrhosis', *Fibrogenesis and Tissue Repair*. doi: 10.1186/1755-1536-5-1.

Harvey, N. T., Chan, J. and Wood, B. A. (2017) 'Skin biopsy in the diagnosis of neoplastic skin disease', *Australian Family Physician*, 46(5), pp. 289-294.

Hendrickx, D. A. E. et al. (2017) 'Gene expression profiling of multiple sclerosis pathology identifies early patterns of demyelination surrounding chronic active lesions', *Frontiers in Immunology*, 8(December). doi: 10.3389/fimmu.2017.01810.

Hogan, J. J., Mocanu, M. and Berns, J. S. (2016) 'The native kidney biopsy: Update and evidence for best practice', *Clinical Journal of the American Society of Nephrology*, pp. 354-356. doi: 10.2215/CJN.05750515.

Hu, C. et al. (2009) 'PPARG, KCNJ11, CDKAL1, CDKN2A-CDKN2B, IDE-KIF11-HHEX, IGF2BP2 and SLC30A8 are associated with type 2 diabetes in a chinese population', *PLoS ONE*, 4(10). doi: 10.1371/journal.pone.0007643.

Ilic, D. et al. (2018) 'Prostate cancer screening with prostate-specific antigen (PSA) test: A systematic review and meta-analysis', *BMJ (Online)*, 362. doi: 10.1136/bmj.k3519.

Ju, W., Smith, S. and Kretzler, M. (2012) 'Genomic bio-markers for chronic kidney disease', *Translational Research*, pp. 290-302. doi: 10.1016/j.trs1.2012.01.020.

Killock, D. (2018) 'Diagnosis: CancerSEEK and destroy-A blood test for early cancer detection', *Nature Reviews Clinical Oncology*, p. 133. doi: 10.1038/nrcli-nonc.2018.21.

Kim, W. J. and Lee, S. Do (2015) 'Candidate genes for COPD: Current evidence and research', *International Journal of COPD*, pp. 2249-2255. doi: 10.2147/COPD.S80227.

Kowalik, A., Kowalewska, M. and Góźdź, S. (2017) 'Current approaches for avoiding the limitations of circulating tumor cells detection methods—implications for diagnosis and treatment of patients with solid tumors', *Translational Research*, pp. 58-84.e15. doi: 10.1016/j.trs1.2017.04.002.

Kuster, G. M. et al. (2020) 'SARS-CoV2: Should inhibitors of the renin-angiotensin systembe withdrawn in patients with COVID-19?', *European Heart Journal*, pp. 1801-1803. doi: 10.1093/eurheartj/ehaa235.

Li, D. et al. (2015) 'OCT4B modulates OCT4A expression as ceRNA in tumor cells', *Oncology Reports*. doi: 10.3892/or 2015.3862.

Lucchinetti, C. F. et al. (2011) 'Inflammatory Cortical Demyelination in Early Multiple Sclerosis', *New England Journal of Medicine*, 365(23), pp. 2188-2197. doi: 10.1056/nejmoa1100648.

Miller, A. B. (2003) 'Book Review Fulfilling the Potential of Cancer Prevention and Early Detection Edited by Susan J. Curry, Tim Byers, and Maria Hewitt. 542 pp., illustrated. Washington, D.C., National Academies Press, 2003. $59.95. 0-309-08254-4', *New England Journal of Medicine*, 349(18), pp. 1781-1782. doi: 10.1056/nejm200310303491824.

Mlika, M. et al. (2017) 'Liquid biopsy in lung cancer', *Tunisie Medicale*, pp. 965-971.

Monferrer, E. et al. (2019) 'High Oct4 expression: Implications in the pathogenesis of neuroblastic tumours', *BMC Cancer*, 19(1). doi: 10.1186/s12885-018-5219-3.

Riggi, N., Aguet, M. and Stamenkovic, I. (2018) 'Cancer Metastasis: A Reappraisal of Its Underlying Mechanisms and Their Relevance to Treatment', *Annual Review of Pathology: Mechanisms of Disease*, 13, pp. 117-140. doi: 10.1146/annurev-pathol-020117-044127.

Schiffman, J. D., Fisher, P. G. and Gibbs, P. (2015) 'Early Detection of Cancer: Past, Present, and Future', *American Society of Clinical Oncology Educational Book*, (35), pp. 57-65. doi: 10.14694/edbook_am.2015.35.57.

Shaw, P. and Crosby, T. (2008) 'Cancer of unknown primary', in *Practical Clinical Oncology*, pp. 442-448. doi: 10.1017/CBO9780511545375.039.

Shen, Z., Wu, A. and Chen, X. (2017) 'Current detection technologies for circulating tumor cells', *Chemical Society Reviews*, pp. 2038-2056. doi: 10.1039/c6cs00803h.

Sherman, K. E. et al. (2007) 'Liver biopsy in cirrhotic patients', *American Journal of Gastroenterology*, 102(4), pp. 789-793. doi: 10.1111/j.1572-0241.2007.01110.x.

Sodja, E. et al. (2016) 'The prognostic value of whole blood SOX2, NANOG and OCT4 mRNA expression in advanced small-cell lung cancer', *Radiology and Oncology*, 50(2), pp. 188-196. doi: 10.1515/raon-2015-0027.

Temilola, D. O. et al. (2019) 'The Prospect and Challenges to the Flow of Liquid Biopsy in Africa', *Cells*. doi: 10.3390/cells8080862.

Vaduganathan, M. et al. (2020) 'Renin-Angiotensin-Aldosterone System Inhibitors in Patients with Covid-19', *New England Journal of Medicine*, 382(17), pp. 1653-1659. doi: 10.1056/nejmsr2005760.

Wang, Y. J. and Herlyn, M. (2015) 'The emerging roles of Oct4 in tumor-initiating cells', *American Journal of Physiology-Cell Physiology*, 309(11), pp. C709-C718. doi: 10.1152/ajpcell.00212.2015.

Wang, X. and Dai, J. (2010) 'Concise review: Isoforms of OCT4 contribute to the confusing diversity in stem cell biology', *Stem Cells*. doi: 10.1002/stem.419.

Westcott, P. M. K. and To, M. D. (2013) 'The genetics and biology of KRAS in lung cancer', *Chinese Journal of Cancer*, pp. 63-70. doi: 10.5732/cjc.012.10098.

Wong, S. Q. et al. (2014) 'Sequence artefacts in a prospective series of formalin-fixed tumours tested for mutations in hotspot regions by massively parallel sequencing', *BMC Medical Genomics*, 7(1). doi: 10.1186/1755-8794-7-23.

Thong, L. et al. (2016) 'Correlation between gene expression and osteoarthritis progression in human', *International Journal of Molecular Sciences*, 17(7). doi: 10.3390/ijms17071126.

Thou, B. et al. (2020) 'Application of exosomes as liquid biopsy in clinical diagnosis', *Signal Transduction and Targeted Therapy*. doi: 10.1038/s41392-020-00258-9.

I claim:

1. A method for detecting a presence or an absence of cancer in a subject, comprising:

(a) obtaining a whole blood sample from the subject;

(b) contacting the whole blood sample with a neutral buffer and then with a salt solution, followed by performing a first centrifugation at a first speed to obtain a first pellet of cells, wherein the contacting is performed with a first ratio range of 1:1 to 1:20 between the whole blood sample and the neutral buffer, and wherein the contacting is performed with a second ratio in a range of 1:2 to 1:10 between (1) the salt solution and (2) the whole blood sample contacted with the neutral buffer;

(c) performing a second centrifugation at a second speed to obtain a second pellet of cells;

(d) isolating messenger ribonucleic acid (mRNA) from the second pellet of cells;

(e) assaying the isolated mRNA to (i) detect a presence of Oct4A-expressing cells among the second pellet of cells and (ii) determine an expression level of Oct4A;

(f) comparing the determined expression level of Oct4A with a reference expression level; and (g) detecting the presence of cancer in the subject when the determined expression level of Oct4A is increased by a range of at least 5 folds and less than 10 folds as compared to the reference expression level.

2. A method for predicting onset of cancer in a subject, comprising:

(a) obtaining a whole blood sample from the subject;

(b) contacting the whole blood sample with a neutral buffer and then with a salt solution, followed by performing a first centrifugation to obtain a first pellet of cells, wherein the contacting is performed with a first ratio range of 1:1 to 1:20 between the whole blood sample and the neutral buffer, and wherein the contacting is performed with a second ratio in a range of 1:2 to 1:10 between (1) the salt solution and (2) the whole blood sample contacted with the neutral buffer;

(c) performing a second centrifugation at a second speed to obtain a second pellet of cells;

(d) isolating messenger ribonucleic acid (mRNA) from the second pellet of cells;

(e) assaying the isolated mRNA to (i) detect a presence of Oct4A-expressing cells among the second pellet of cells and (ii) determine an expression level of Oct4A;

(f) comparing the determined expression level of Oct4A with a reference expression level; and (g) predicting the onset of cancer in the subject when the determined expression level of Oct4A is increased by a range of at least 3 folds and less than 5 folds as compared to the reference expression level.

3. The method of claim 1, wherein the assaying comprises sequencing the isolated mRNA or derivatives thereof to determine the expression level of Oct4A.

4. The method of claim 2, wherein the assaying comprises sequencing the isolated mRNA or derivatives thereof to determine the expression level of Oct4A.

5. The method of claim 1, wherein (d) further comprises at least one of: (a) guanidinium thiocyanate-phenol-chloroform nucleic acid extraction; (b) cesium chloride gradient centrifugation; (c) cetyltrimethylammonium bromide nucleic acid extraction; (d) alkaline extraction; (e) resin-based extraction; and (f) solid phase nucleic acid extraction.

6. The method of claim 2, wherein (d) further comprises at least one of: (i) guanidinium thiocyanate-phenol-chloroform nucleic acid extraction; (ii) cesium chloride gradient centrifugation; (iii) cetyltrimethylammonium bromide nucleic acid extraction; (iv) alkaline extraction; (v) resin-based extraction; and (vi) solid phase nucleic acid extraction.

7. The method of claim 1, wherein the reference expression level of Oct4A is determined from a whole blood sample of a cancer-free subject.

8. The method of claim 1, wherein the method is independent of invasive techniques.

9. The method of claim 2, wherein (e) further comprises performing nucleic acid sequencing of the isolated mRNA to detect a presence or an absence of a mutation in at least one cancer-related genetic marker.

10. The method of claim 2, wherein the method is independent of invasive techniques.

11. The method of claim 1, wherein the assaying comprises performing quantitative polymerase chain reaction (qPCR).

12. The method of claim 2, wherein the assaying comprises performing qPCR.

13. The method of claim 3, further comprising reverse transcribing the isolated mRNA to produce complementary deoxyribonucleic acid (cDNA), and sequencing the cDNA or derivatives thereof to determine the expression level of Oct4A.

14. The method of claim 4, further comprising reverse transcribing the isolated mRNA to produce complementary deoxyribonucleic acid (cDNA), and sequencing the cDNA or derivatives thereof to determine the expression level of Oct4A.

15. The method of claim 1, wherein the first centrifugation comprises density gradient centrifugation using Ficoll-Hypaque.

16. The method of claim 2, wherein the first centrifugation comprises density gradient centrifugation using Ficoll-Hypaque.

* * * * *

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: SEQ ID NO: 1 depicts the forward primer squence
      for Oct 4a gene

<400> SEQUENCE: 1
agccctcatt tcaccaggcc                                              20

<210> SEQ ID NO 2
<211> LENGTH: 20
<212> TYPE: DNA
<213> ORGANISM: Artificial Sequence
<220> FEATURE:
```

```
<223> OTHER INFORMATION: SEQ ID NO: 2 depicts the reverse primer
      sequence for Oct 4a gene

<400> SEQUENCE: 2
tgggactcct ccgggttttg                                              20

<210> SEQ ID NO 3
<211> LENGTH: 20
<212> TYPE: DNA
<213> ORGANISM: Artificial Sequence
<220> FEATURE:
<223> OTHER INFORMATION: SEQ ID NO: 3 depicts the forward primer
      sequence for LINE 1 family (79 bp)

<400> SEQUENCE: 3
agggacatgg atgaaattgg                                              20

<210> SEQ ID NO 4
<211> LENGTH: 20
<212> TYPE: DNA
<213> ORGANISM: Artificial Sequence
<220> FEATURE:
<223> OTHER INFORMATION: SEQ ID NO: 4 depicts the reverse primer
      sequence for LINE 1 family (79 bp)

<400> SEQUENCE: 4
tgagaatatg cggtgtttgg                                              20

<210> SEQ ID NO 5
<211> LENGTH: 21
<212> TYPE: DNA
<213> ORGANISM: Artificial Sequence
<220> FEATURE:
<223> OTHER INFORMATION: SEQ ID NO: 5 depicts the forward primer
      sequence for LINE 1 family (97 bp)

<400> SEQUENCE: 5
tggcacatat acaccatgga a                                            21

<210> SEQ ID NO 6
<211> LENGTH: 23
<212> TYPE: DNA
<213> ORGANISM: Artificial Sequence
<220> FEATURE:
<223> OTHER INFORMATION: SEQ ID NO: 6 depicts the reverse primer
      sequence for LINE1 family (97 bp)

<400> SEQUENCE: 6
tgagaatgat ggtttccaat ttc                                          23

<210> SEQ ID NO 7
<211> LENGTH: 20
<212> TYPE: DNA
<213> ORGANISM: Artificial Sequence
<220> FEATURE:
<223> OTHER INFORMATION: SEQ ID NO: 7 depicts the forward primer
      sequence for LINE1 family (127 bp)

<400> SEQUENCE: 7
acttggaacc aacccaaatg                                              20

<210> SEQ ID NO 8
<211> LENGTH: 21
<212> TYPE: DNA
<213> ORGANISM: Artificial Sequence
<220> FEATURE:
<223> OTHER INFORMATION: SEQ ID NO: 8 depicts the reverse primer
```

-continued sequence for LINE1 family (127 bp)

<400> SEQUENCE: 8
tcatccatgt ccctacaaag g                                                                    21